(12) United States Patent
Cushing et al.

(10) Patent No.: US 7,176,314 B2
(45) Date of Patent: Feb. 13, 2007

(54) INFLAMMATION MODULATORS

(75) Inventors: Timothy D. Cushing, Pacifica, CA (US); Xiao He, Foster City, CA (US); Marie-Louise Smith, Half Moon Bay, CA (US); Michael R. DeGraffenreid, San Francisco, CA (US); Jay Powers, Pacifica, CA (US); Craig S. Tomooka, San Mateo, CA (US); David L. Clark, Albany, CA (US); Xiaolin Hao, San Francisco, CA (US); Juan C. Jaen, Burlingame, CA (US); Marc Labelle, Burlingame, CA (US); Nigel P. C. Walker, Burlingame, CA (US); Adrian L. Gill, Wilstead (GB); Francisco X. Talamas, Mountain View, CA (US); Sharada Labadie, Sunnyvale, CA (US)

(73) Assignee: Amgen, Inc., South San Francisco, CA (US)

( * ) Notice: Subject to any disclaimer, the term of this patent is extended or adjusted under 35 U.S.C. 154(b) by 375 days.

(21) Appl. No.: 10/314,428

(22) Filed: Dec. 4, 2002

(65) Prior Publication Data

US 2003/0181472 A1 Sep. 25, 2003

Related U.S. Application Data

(60) Provisional application No. 60/337,460, filed on Dec. 5, 2001.

(51) Int. Cl.
*C07D 215/00* (2006.01)
*C09B 25/00* (2006.01)

(52) U.S. Cl. .................. 546/152; 546/155
(58) Field of Classification Search .............. 546/152, 546/155; 514/279
See application file for complete search history.

(56) References Cited

U.S. PATENT DOCUMENTS

| | | | |
|---|---|---|---|
| 3,340,260 A | 9/1967 | Blatter | |
| 3,705,898 A | 12/1972 | Alalmo | |
| 4,433,150 A * | 2/1984 | Champseix et al. | ........ 546/168 |
| 6,184,226 B1 | 2/2001 | Chakravarty | |

FOREIGN PATENT DOCUMENTS

| | | |
|---|---|---|
| DE | 21 06 510 A | 8/1971 |
| DE | 22 22 231 A | 6/1974 |
| DE | 28 26 526 A | 1/1979 |
| EP | 0 579 496 A | 1/1994 |
| WO | WO 99/01441 A | 1/1999 |
| WO | WO 01/00610 A1 | 1/2001 |
| WO | WO 01/30774 A1 | 5/2001 |
| WO | WO 01/58890 A1 | 8/2001 |
| WO | WO 01/68648 A1 | 9/2001 |
| WO | WO 01/83456 A | 11/2001 |
| WO | WO 01/90074 A | 11/2001 |
| WO | WO 02/24679 A1 | 3/2002 |
| WO | WO 02/28837 A1 | 4/2002 |
| WO | WO 02/28860 A2 | 4/2002 |
| WO | WO 02/30353 A2 | 4/2002 |
| WO | WO 02/30423 A1 | 4/2002 |
| WO | WO 02/41843 A2 | 5/2002 |
| WO | WO 02/44153 A1 | 6/2002 |
| WO | WO 02/46171 A2 | 6/2002 |
| WO | WO 02/060386 A2 | 8/2002 |
| WO | WO 02/076985 A1 | 10/2002 |

OTHER PUBLICATIONS

Kulkarni et al. "tynthesis, reactions, mass sprectra and biological evaluation of some new 4-aryloxymethylcarbostyrils", Journal of the Indian Chemical Society, 1996, 73(9), 495-496.*
Pavlova et al., "Synthesis and anti-inflammatory and anagesic activity . . . ", Pharmaceutical Chemistry Journal, 1999, 33(8), 419-420.*
El Bednary et al., Boll. Chim. Farm. 135(11):617-20 (1996); & Database Crossfire Beilstein [Online]; Beilstein Institut zur Forderung der Chemischen Wissenschaften, Frankfurt am Main, DE; retrieved from XFIRE, Accession No. 7798089.
Khazan et al., "Synthesis of substituted 2-(1-methyl-2-imidazolyl)quinolines" J. Heterocyclic Chem. 34:1543-47 (1997).
Lee, S. et al., "Discovery of potent cyclic GMP phosphodiesterase inhibitors. 2-pyridyl-and 2-imidazolylquinazolines possessing cyclic GMP phosphodiesterase and thromboxane synthesis inhibitory activities" J. Med. Chem. 38(18):3547-3557 (1995).
Patterson et al., "A new synthesis of N-substituted-2-alkyl(or aryl)quinazolin-4-amines by amide base-mediated cyclization of carboximidamides derived from 2-(trifluoromethyl)benzeneamine" H. Heterocyclic Chem. 29:703-706 (1992).
Strekowski, L. et al., "Synthesis and quantitative structure-activity relationship analysis of 2-(aryl or heteroaryl)quinolin-4-amines, a new class of anti-HIV-1 agents" J. Med. Chem. 34(5):1739-1746 (1991).
van Muijlwijk-Koezen et al., "Isoquinoline and quinazoline urea analogues as antagonists for the human adenosine $A_3$ receptor" J. Med. Chem. 43(5):2227-2338 (2000).

* cited by examiner

*Primary Examiner*—James O. Wilson
*Assistant Examiner*—Paul V. Ward
(74) *Attorney, Agent, or Firm*—Jones Day

(57) ABSTRACT

Compounds, compositions and methods that are useful in the treatment of inflammatory, immunoregulatory, metabolic and cell proliferative conditions or diseases are provided herein. In particular, the invention provides compounds which modulate the expression and/or function of proteins involved in inflammation, metabolism and cell proliferation. The subject compounds contain quinoline or quinazoline rings.

45 Claims, 7 Drawing Sheets

46

47

48

21

49

50

INFLAMMATION MODULATORS

CROSS-REFERENCES TO RELATED APPLICATIONS

This application claims the benefit of provisional application Ser. No. 60/337,460, filed Dec. 5, 2001, the entire contents of which are incorporated herein by reference.

BACKGROUND OF THE INVENTION

Tumor Necrosis Factor (TNF) and interleukin-1 (IL-1) are cytokines that have been implicated in a wide range of biological processes, including inflammation. The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, diabetes, obesity, bone mass loss, cancer, neurological conditions such as ischemic stroke or closed head injuries, etc.

Cytokines trigger a variety of changes in gene expression in their target cells by binding and activating their respective cognate receptors. Receptor activation sets in motion certain biochemical events, including the activation of otherwise latent transcription factors. Members of the NF-κB Rel family of transcription factors represent some of the most prominent of these transcription factors, having been implicated in the regulation of genes involved in inflammation, cell proliferation, apoptosis, and several other basic cellular functions (Verma et al. *Genes Dev.* 9, 2723 (1995); Baichwal & Baeuerle, *Curr. Biol.* 7, 94 (1997)).

The best studied member of this family of transcription factors is NF-κB, which generally exists in cells as a heterodimer of two proteins: p50 (NF-κB1) and p65 (RelA), although homodimers of these individual components are also possible (Baeuerle and Baltimore, *Cell*, 53, 211 (1988); Baeuerle and Henkel, *Annu. Rev. Immunol.* 12, 141 (1994)). NF-κB, in its inactive form, resides in the cytoplasm of cells. In response to various types of stimuli, such as proinflammatory cytokines (e.g., TNF and IL-1), ultraviolet irradiation and viral infection (Verma, 1995; Baichwal, 1997; Cao et al. *Science*, 271, 1128 (1996),) NF-κB migrates to the nucleus. TNF and IL-1 have been shown to be two key proinflammation agents in a wide variety of pathological conditions, including rheumatoid arthritis, septic shock, inflammatory bowel disease, dermal sensitization disorders, neurological trauma such as stroke or closed-head injuries, etc.

In its inactive state, the NF-κB heterodimer is held in the cytoplasm by association with inhibitory IkB proteins. Recently, the three-dimensional structure of a NF-κB/IkB ternary complex has been solved (Huxford et al. *Cell*, 95, 759 (1998); Jacobs et al. *Cell*, 95, 749 (1998)). When cells are treated with the appropriate stimuli, such as IL-1 or TNF, intracellular signal transduction pathways are activated that lead to the eventual phosphorylation of IkB proteins on two specific residues (serines 32 and 36 in IkBα, serines 19 and 23 in IkB β). Mutation of one or both serine residues renders IkB resistant to cytokine-induced phosphorylation. This signal-induced phosphorylation targets IkB for ubiquitination and proteosome-mediated degradation, allowing nuclear translocation of NF-κB (Thanos and Maniatis, *Cell*, 80, 529 (1995)). The only regulated step in the IkB degradation pathway is the phosphorylation of IWB by IkB kinases (IKK) (Yaron et al. *EMBO J.* 16, 6486 (1997)).

Several intermediate steps in the TNF- and IL-1-activated signaling pathways that result in IkB phosphorylation have been elucidated in recent years. Both pathways appear to merge at the level of the protein kinase NIK (NF-κB-inducing kinase) (Malinin et al. *Nature*, 385, 540 (1997); Song et al. *Proc. Natl. Acad. Sci. USA*, 94, 9792 (1997)). Similarly, the protein kinases MEKK1 and MLK3 have been implicated in the induction of IKK activity (Lee et al. *Proc. Natl. Acad. Sci. USA*. 95, 9319 (1998); Hehner et al. *Mol. Cell. Biol.* 20, 2556 (2000)). While the specific details remain somewhat unclear regarding how these or other intermediate proteins may interact with and/or stimulate IKK activity in cells, significant progress has been made in elucidating the enzymes responsible for IkB phosphorylation. Two IKK enzymes, generally referred to as IKKα and IKK β (Woronicz et al. *Science*, 278, 866 (1997); Zandi et al. *Cell*, 91, 243 (1997)) or IKK-1 and IKK-2 (Mercurio et al. *Science*, 278, 860 (1997)) have been discovered. Both forms of IKK can exist as homodimers and as IKKα/IKK β heterodimers. Another recently discovered component of the IkB kinase complex is a regulatory protein, known as IKK-gamma or NEMO (NF-κB-Essential Modulator) (Rothwarf et al. *Nature*, 395, 297 (1998)). NEMO does not contain a catalytic domain, and thus it appears to have no direct kinase activity and it probably serves a regulatory function. Existing data suggest that the predominant form of IKK in cells is an IKKα/IKK β heterodimer associated with either a dimer or a trimer of NEMO (Rothwarf et al. *Nature* 395, 297 (1998)).

Biochemical and molecular biology experiments have clearly identified IKKα and IKK β as the most likely mediators of TNF- and IL-1-induced IkB phosphorylation and degradation, which results in NF-κB activation and upregulation of families of genes involved in inflammatory processes (Woronicz et al. *Science* (1997); Karin, *Oncogene* 18, 6867 (1999); Karin, *J. Biol. Chem.* 274, 27339 (1999)). IKKα and IKKβ have very similar primary structures, displaying more than 50% overall sequence identity. In the kinase domain, their sequences are 65% identical.

Based on our present understanding of the critical role played by TNF and IL-1 in the wide array of pathological conditions described above, and the involvement of IKKα and IKKβ in the signal transduction of both cytokines, the discovery of compounds that potently and selectively inhibit either of these kinases would result in a major advancement in the therapy of those conditions. In this application we describe a novel type of compounds which displays such desirable activity.

SUMMARY OF THE INVENTION

In one aspect, the present invention provides compounds useful in the treatment of inflammatory, metabolic or malignant conditions, having the formula (I):

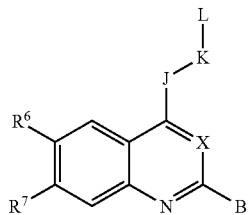

In formula I, X is N or CR$^5$;

J is selected from (C$_1$–C$_4$)alkylene, (C$_2$–C$_4$)alkenylene, (C$_2$–C$_4$)alkynylene, C(=Y), NR$^1$, O, S(O)$_m$, C(=Y)NR$^1$, (C$_1$–C$_4$)alkylene-NR$^1$, (C$_1$–C$_4$)alkylene-O and C(R$^2$)=N;

K is selected from a bond, (C$_1$–C$_4$)alkylene, C(=Y), NR$^1$, O and S(O)$_m$;

L is selected from H, (C$_1$–C$_6$)alkyl, OR$^1$, hetero(C$_1$–C$_6$)alkyl, aryl, heteroaryl, NR$^2$R$^3$, C(=Y)R$^2$, C(=Y)NR$^2$R$^3$, C(=Y)OR$^2$, (C$_1$–C$_4$)alkylene-C(=Y)R$^2$, (C$_1$–C$_4$)alkylene-C(=Y)NR$^2$R$^3$, and (C$_1$–C$_4$)alkylene-C(=Y)OR$^2$;

optionally, J may be combined with K or L to form a 5-, 6-, 7- or 8-membered ring containing from 0 to 3 heteroatoms selected from N, O and S;

optionally, K may be combined with L to form 5-, 6-, 7- or 8-membered ring containing from 0 to 3 heteroatoms selected from N, O and S;

B is a five- or six-membered aromatic ring system containing at least one heteroatom selected from the group consisting of N, O and S;

Y is selected from O, S, NR$^1$, N(CN) and NOR$^1$;

R$^1$, R$^2$ and R$^3$ independently represent H, (C$_1$–C$_{10}$)alkyl, (C$_3$–C$_{10}$)alkenyl, (C$_2$–C$_{10}$)alkynyl, (C$_1$–C$_{10}$)heteroalkyl, (C$_3$–C$_{10}$)cycloalkyl, (C$_3$–C$_{10}$)cycloalkyl-alkyl, (C$_3$–C$_{10}$)cycloheteroalkyl-alkyl, (C$_3$–C$_{10}$)cycloheteroalkyl, aryl, aryl(C$_1$–C$_4$)alkyl, aryl(C$_1$–C$_4$)heteroalkyl, heteroaryl(C$_1$–C$_4$)alkyl, heteroaryl(C$_1$–C$_4$)heteroalkyl or fluoro(C$_1$–C$_6$)alkyl;

optionally, when R$^2$ and R$^3$ are attached to the same nitrogen atom, R$^2$ and R$^3$ may be combined with the nitrogen atom to form a 5-, 6- or 7-membered ring containing from 1 to 3 heteroatoms selected from N, O and S;

R$^5$, R$^6$ and R$^7$ are independently selected from H, halogen, (C$_1$–C$_4$)fluoroalkyl, (C$_1$–C$_6$)alkyl, (C$_2$–C$_6$)alkenyl, (C$_2$–C$_6$)alkynyl, (C$_1$–C$_6$)heteroalkyl, (C$_1$–C$_6$)alkoxy, (C$_1$–C$_6$)thioalkoxy, amino, (C$_1$–C$_6$)alkylamino, di(C$_1$–C$_6$)alkylamino, (C$_3$–C$_{10}$)cycloalkyl, (C$_3$–C$_{10}$)cycloalkyl-alkyl, (C$_3$–C$_{10}$)cycloheteroalkyl, (C$_3$–C$_{10}$)cycloheteroalkyl-alkyl, cyano, cyano-(C$_1$–C$_6$)alkyl, cyano-(C$_2$–C$_6$)alkenyl, nitro, (C$_1$–C$_6$)acyl, (C$_1$–C$_6$)acylamino, (C$_1$–C$_6$)alkoxycarbonyl, (C$_1$–C$_6$)alkoxycarbonyl-(C$_1$–C$_6$)alkyl, CONH$_2$, CO—NH—(C$_1$–C$_6$)alkyl, CO—N[(C$_1$–C$_6$)alkyl]$_2$, SO$_2$NH$_2$, SO$_2$NH—(C$_1$–C$_6$)alkyl, SO$_2$N—[(C$_1$–C$_6$)alkyl]$_2$ and (C$_1$–C$_6$)heteroalkoxy;

optionally, R$^6$ and R$^7$ may be combined to form a new 5- or 6-membered fused ring containing from 0 to 3 heteroatoms selected from N, O and S; and the subscript m is an integer of from 0 to 2;

with the proviso that the compound is other than:

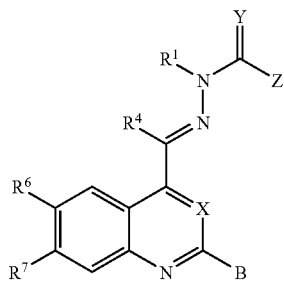

wherein

Z is selected from H, (C$_1$–C$_{10}$)alkyl, (C$_3$–C$_{10}$)cycloalkyl, (C$_3$–C$_{10}$)cycloalkyl-alkyl, (C$_2$–C$_{10}$)alkenyl, (C$_2$–C$_{10}$)alkynyl and NR$^2$R$^3$; and R$^4$ is selected from H, (C$_1$–C$_{10}$)alkyl, (C$_3$–C$_6$)cycloalkyl, (C$_4$–C$_7$)cycloalkyl-alkyl, (C$_2$–C$_6$)alkenyl and (C$_2$–C$_6$)alkynyl.

The present invention also provides compounds having the formula (I):

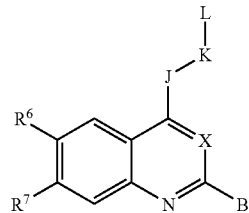

wherein

X is N or CR$^5$;

J is selected from (C$_1$–C$_4$)alkylene, (C$_2$–C$_4$)alkenylene, (C$_2$–C$_4$)alkynylene, C(=Y), NR$^1$, O, S(O)$_m$, C(=Y)NR$^1$, (C$_1$–C$_4$)alkylene-NR$^1$, (C$_1$–C$_4$)alkylene-O and C(R$^2$)N;

K is selected from a bond, (C$_1$–C$_4$)alkylene, C(=Y), O and S(O)$_m$;

L is selected from H, (C$_1$–C$_6$)alkyl, OR$^1$, hetero(C$_1$–C$_6$)alkyl, aryl, heteroaryl, NR$^2$ R$^3$, C(=Y)R$^2$, C(=Y)NR$^2$R$^3$, C(=Y)OR$^2$, (C$_1$–C$_4$)alkylene-C(=Y)R$^2$, (C$^1$–C$_4$)alkylene-C(=Y)NR$^2$R$^3$ and (C$_1$–C$_4$)alkylene-C(=Y)OR$^2$;

optionally, J may be combined with K or L to form a 5-, 6-, 7- or 8-membered ring containing from 0 to 3 heteroatoms selected from N, O and S;

optionally, K may be combined with L to form 5-, 6-, 7- or 8-membered ring containing from 0 to 3 heteroatoms selected from N, O and S;

B is a five- or six-membered aromatic ring system containing at least one heteroatom selected from the group consisting of N, O and S;

Y is selected from O, S, NR$^1$, N(CN) and NOR$^1$;

R$^1$, R$^2$ and R$^3$ are independently selected from H, (C$_1$–C$_{10}$)alkyl, (C$_3$–C$_{10}$)alkenyl, (C$_2$–C$_{10}$)alkynyl, (C$_1$–C$_{10}$)heteroalkyl, (C$_3$–C$_{10}$)cycloalkyl, (C$_3$–C$_{10}$)cycloalkyl-alkyl, (C$_3$–C$_{10}$)cycloheteroalkyl-alkyl, (C$_3$–C$_{10}$)cycloheteroalkyl, aryl, aryl(C$_1$–C$_4$)alkyl, aryl(C$_1$–C$_4$)heteroalkyl, heteroaryl(C$_1$–C$_4$)alkyl, heteroaryl(C$_1$–C$_4$)heteroalkyl and fluoro(C$_1$–C$_6$)alkyl;

optionally, when R$^2$ and R$^3$ are attached to the same nitrogen atom, R$^2$ and R$^3$ may be combined with the nitrogen atom to form a 5-, 6- or 7-membered ring containing from 1 to 3 heteroatoms selected from N, O and S;

$R^5$, $R^6$ and $R^7$ are independently selected from H, halogen, $(C_1–C_4)$fluoroalkyl, $(C_1–C_6)$alkyl, $(C_2–C_6)$alkenyl, $(C_2–C_6)$alkynyl, $(C_1–C_6)$heteroalkyl, $(C_1–C_6)$alkoxy, $(C_1–C_6)$thioalkoxy, amino, $(C_1–C_6)$alkylamino, di$(C_1–C_6)$alkylamino, $(C_3–C_{10})$cycloalkyl, $(C_3–C_{10})$cycloalkyl-alkyl, $(C_3–C_{10})$cycloheteroalkyl, $(C_3–C_{10})$cycloheteroalkyl-alkyl, cyano, cyano-$(C_1–C_6)$alkyl, cyano-$(C_2–C_6)$alkenyl, nitro, $(C_1–C_6)$acyl, $(C_1–C_6)$acylamino, $(C_1–C_6)$alkoxycarbonyl, $(C_1–C_6)$alkoxycarbonyl $(C_1–C_6)$alkyl, $CONH_2$, CO—NH—$(C_1–C_6)$alkyl, CO—N[$(C_1–C_6)$alkyl]$_2$, $SO_2NH_2$, $SO_2$NH—$(C_1–C_6)$alkyl, $SO_2$N—[$(C_1–C_6)$alkyl]$_2$ and $(C_1–C_6)$heteroalkoxy;

optionally, $R^6$ and $R^7$ may be combined to form a new 5- or 6-membered fused ring containing from 0 to 3 heteroatoms selected from N, O and S; and the subscript m is an integer of from 0 to 2.

The present invention also provides compounds having the formula (I):

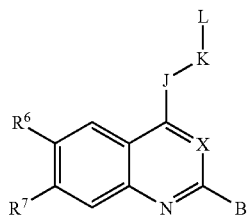

I wherein

X is N or $CR^5$;

J is selected from $(C_1–C_4)$alkylene, $(C_2–C_4)$alkenylene, $(C_2–C_4)$alkynylene, C(=Y), $NR^1$, O, $S(O)_m$, C(=Y)$NR^1$, $(C_1–C_4)$alkylene-$NR^1$, $(C_1–C_4)$alkylene-O and $C(R^2)$=N;

K is selected from a bond, $(C_1–C_4)$alkylene, C(=Y), $NR^1$, O and $S(O)_m$;

L is selected from H, $(C_1–C_6)$alkyl, $OR^1$, hetero$(C_1–C_6)$alkyl, aryl, heteroaryl, $NR^2R^3$, C(=Y)$OR^2$, $(C_1–C_4)$alkylene-C(=Y)$NR^2R^3$, $(C_1–C_4)$alkylene-C(=Y)$R^2$ and $(C_1–C_4)$alkylene-C(=Y)$OR^2$;

optionally, J may be combined with K or L to form a 5-, 6-, 7- or 8-membered ring containing from 0 to 3 heteroatoms selected from N, O and S;

optionally, K may be combined with L to form 5-, 6-, 7- or 8-membered ring containing from 0 to 3 heteroatoms selected from N, O and S;

B is a five- or six-membered aromatic ring system containing at least one heteroatom selected from the group consisting of N, O and S;

Y is selected from O, S, $NR^1$, N(CN) and $NOR^1$;

$R^1$, $R^2$ and $R^3$ are independently selected from H, $(C_1–C_{10})$alkyl, $(C_3–C_{10})$alkenyl, $(C_2–C_{10})$alkynyl, $(C_1–C_{10})$heteroalkyl, $(C_3–C_{10})$cycloalkyl, $(C_3–C_{10})$cycloalkyl-alkyl, $(C_3–C_{10})$cycloheteroalkyl-alkyl, $(C_3–C_{10})$cycloheteroalkyl, aryl, aryl$(C_1–C_4)$alkyl, aryl $(C_1–C_4)$heteroalkyl, heteroaryl$(C_1–C_4)$alkyl, heteroaryl$(C_1–C_4)$heteroalkyl and fluoro$(C_1–C_6)$alkyl;

optionally, when $R^2$ and $R^3$ are attached to the same nitrogen atom, $R^2$ and $R^3$ may be combined with the nitrogen atom to form a 5-, 6- or 7-membered ring containing from 1 to 3 heteroatoms selected from N, O and S;

$R^5$, $R^6$ and $R^7$ are independently selected from H, halogen, $(C_1–C_4)$fluoroalkyl, $(C_1–C_6)$alkyl, $(C_2–C_6)$alkenyl, $(C_2–C_6)$alkynyl, $(C_1–C_6)$heteroalkyl, $(C_1–C_6)$alkoxy, $(C_1–C_6)$thioalkoxy, amino, $(C_1–C_6)$alkylamino, di$(C_1–C_6)$alkyl amino, $(C_3–C_{10})$cycloalkyl, $(C_3–C_{10})$cycloalkyl-alkyl, $(C_3–C_{10})$cycloheteroalkyl, $(C_3–C_{10})$cycloheteroalkyl-alkyl, cyano, cyano-$(C_1–C_6)$alkyl, cyano-$(C_2–C_6)$alkenyl, nitro, $(C_1–C_6)$acyl, $(C_1–C_6)$acylamino, $(C_1–C_6)$alkoxycarbonyl, $(C_1–C_6)$alkoxycarbonyl $(C_1–C_6)$alkyl, $CONH_2$, CO—NH—$(C_1–C_6)$alkyl, CO—N[$(C_1–C_6)$alkyl]$_2$, $SO_2NH_2$, $SO_2$NH—$(C_1–C_6)$alkyl, $SO_2$N—[$(C_1–C_6)$alkyl]$_2$ and $(C_1–C_6)$heteroalkoxy;

optionally, $R^6$ and $R^7$ may be combined to form a new 5- or 6-membered fused ring containing from 0 to 3 heteroatoms selected from N, O and S; and the subscript m is an integer of from 0 to 2.

The present invention further provides compounds having the formula (I):

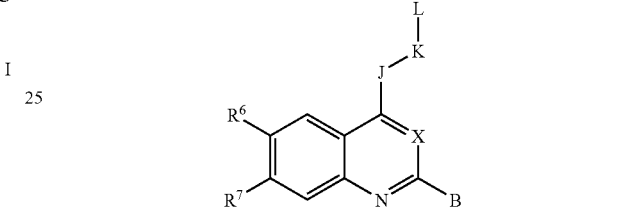

I wherein

X is N or $CR^5$;

J is selected from $(C_1–C_4)$alkylene, $(C_2–C_4)$alkenylene, $(C_2–C_4)$alkynylene, C(=Y), $NR^1$, O, $S(O)_m$, C(=Y)$NR^1$, $(C_1–C_4)$alkylene-$NR^1$ and $(C_1–C_4)$alkylene-O;

K is selected from a bond, $(C_1–C_4)$alkylene, C(=Y), $NR^1$, O and $S(O)_m$;

L is selected from H, $(C_1–C_6)$alkyl, $OR^1$, hetero$(C_1–C_6)$alkyl, aryl, heteroaryl, $NR^2R^3$, C(=Y)$R^2$, C(=Y)$NR^2R^3$, C(=Y)$OR^2$, $(C_1–C_4)$alkylene-C(=Y)$R^2$, $(C_1–C_4)$alkylene-C(=Y)$NR^2R^3$, and $(C_1–C_4)$alkylene-C(=Y)$OR^2$;

optionally, J may be combined with K or L to form a 5-, 6-, 7- or 8-membered ring containing from 0 to 3 heteroatoms selected from N, O and S;

optionally, K may be combined with L to form 5-, 6-, 7- or 8-membered ring containing from 0 to 3 heteroatoms selected from N, O and S;

B is a five- or six-membered aromatic ring system containing at least one heteroatom selected from the group consisting of N, O and S;

Y is selected from O, S, $NR^1$, N(CN) and $NOR^1$;

$R^1$, $R^2$ and $R^3$ are independently selected from H, $(C_1–C_{10})$alkyl, $(C_3–C_{10})$alkenyl, $(C_2–C_{10})$alkynyl, $(C_1–C_{10})$heteroalkyl, $(C_3–C_{10})$cycloalkyl, $(C_3–C_{10})$cycloalkyl-alkyl, $(C_3–C_{10})$cycloheteroalkyl-alkyl, $(C_3–C_{10})$cycloheteroalkyl, aryl, aryl$(C_1–C_4)$alkyl, aryl $(C_1–C_4)$heteroalkyl, heteroaryl$(C_1–C_4)$alkyl, heteroaryl$(C_1–C_4)$heteroalkyl and fluoro$(C_1–C_6)$alkyl;

optionally, when $R^2$ and $R^3$ are attached to the same nitrogen atom, $R^2$ and $R^3$ may be combined with the nitrogen atom to form a 5-, 6- or 7-membered ring containing from 1 to 3 heteroatoms selected from N, O and S;

$R^5$, $R^6$ and $R^7$ are independently selected from H, halogen, $(C_1–C_4)$fluoroalkyl, $(C_1–C_6)$alkyl, $(C_2–C_6)$alkenyl, $(C_2–C_6)$alkynyl, $(C_1–C_6)$heteroalkyl, $(C_1–C_6)$ alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, CONH$_2$, CO—NH—$(C_1-C_6)$alkyl, CO—N[$(C_1-C_6)$alkyl]$_2$, SO$_2$NH$_2$, SO$_2$NH—$(C_1-C_6)$alkyl, SO$_2$N—[$(C_1-C_6)$alkyl]$_2$ and $(C_1-C_6)$heteroalkoxy;

optionally, $R^6$ and $R^7$ may be combined to form a new 5- or 6-membered fused ring containing from 0 to 3 heteroatoms selected from N, O and S; and the subscript m is an integer of from 0 to 2.

Unless otherwise indicated, the compounds provided in the above formula are meant to include pharmaceutically acceptable salts and prodrugs thereof In another aspect, the present invention provides pharmaceutical compositions comprising one or more compounds of formula I in admixture with a pharmaceutically acceptable carrier or excipient.

In another aspect, the present invention provides methods for the treatment of an inflammatory, metabolic or malignant condition, comprising administering to a subject in need of such treatment a compound of formula I.

In yet another aspect, the present invention provides methods for the treatment of a condition or disorder mediated by IKK.

In yet another aspect, the present invention provides methods for the modulation of IKK.

DETAILED DESCRIPTION OF THE INVENTION

Abbreviations and Definitions

Figure 1A:
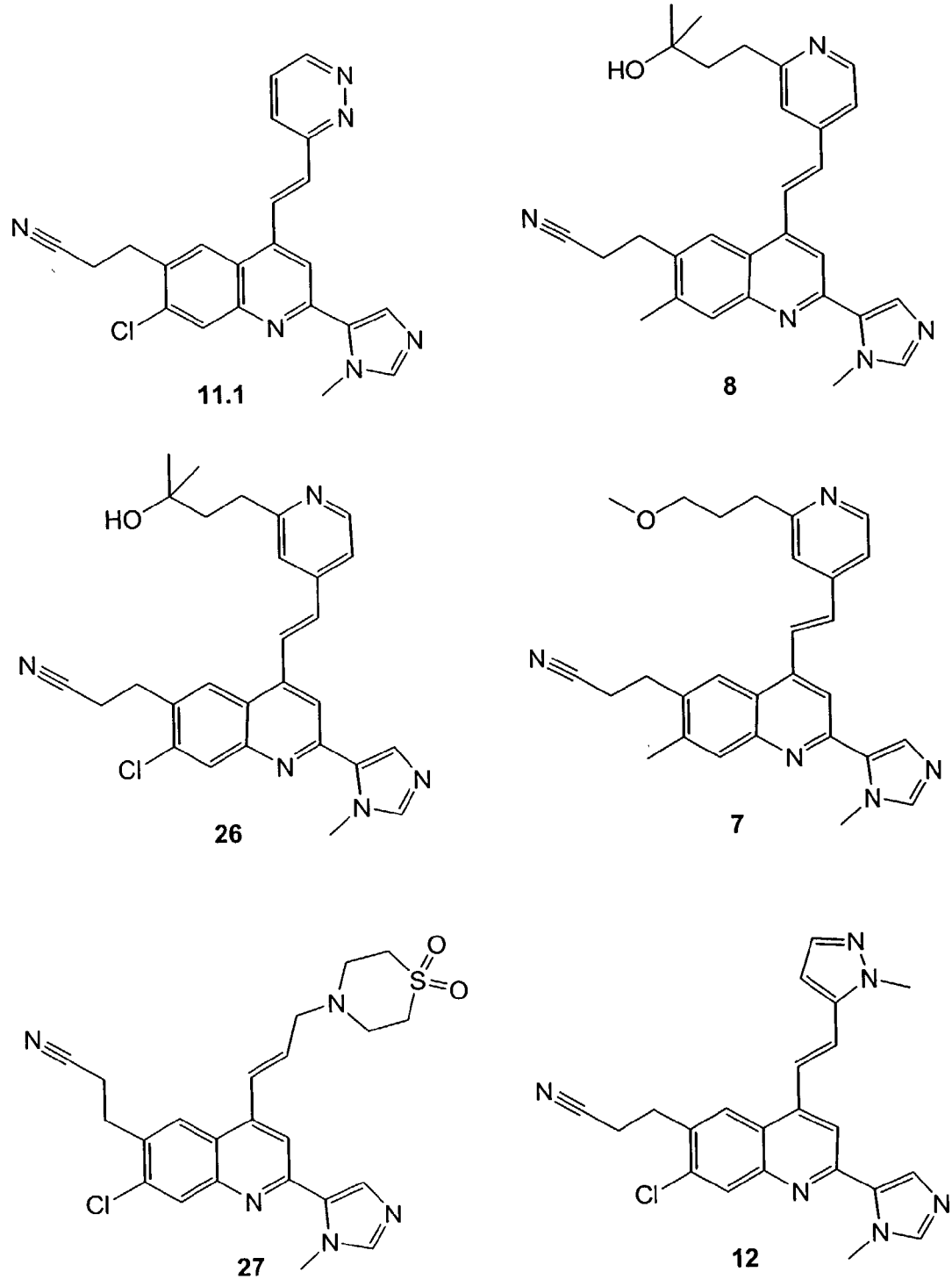
FIG. 1 provides exemplary structures of preferred compounds of the invention.

The abbreviations used herein are conventional, unless otherwise defined.

Unless otherwise stated, the following terms used in the specification and claims have the meanings given below:

"Acyl" means the group —C(O)R', where R' is hydrogen, alkyl, cycloalkyl, cycloalkyl-alkyl, aryl, aryl-alkyl, and variations of these groups in which one or more carbon atoms have been replaced with heteroatoms.

"Alkyl" means a linear saturated monovalent hydrocarbon radical or a branched saturated monovalent hydrocarbon radical having the number of carbon atoms indicated in the prefix. For example, $(C_1-C_6)$alkyl is meant to include methyl, ethyl, n-propyl, 2-propyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms.

"Fluoroalkyl" refers to an alkyl group having the indicated number of carbon atoms, in which some of the attached hydrogen atoms have been replaced with fluorine atoms, in a number ranging from 1 to the maximal number of hydrogen atoms on the alkyl group.

"Alkylene" means a linear saturated divalent hydrocarbon radical or a branched saturated divalent hydrocarbon radical having the number of carbon atoms indicated in the prefix.

For example, $(C_1-C_6)$alkylene is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2-C_6)$alkenyl is meant to include, ethenyl, propenyl, and the like.

"Alkenylene" means a linear divalent hydrocarbon radical or a branched divalent hydrocarbon radical having the number of carbon atoms indicated in the prefix and containing at least one double bond. For example, $(C_2-C_6)$alkenylene is meant to include ethenylene, propenylene, and the like.

"Alkynyl" means a linear monovalent hydrocarbon radical or a branched monovalent hydrocarbon radical containing at least one triple bond and having the number of carbon atoms indicated in the prefix. For example, $(C_2-C_6)$alkynyl is meant to include ethynyl, propynyl, and the like.

"Alkynylene" means a linear divalent hydrocarbon radical or a branched divalent hydrocarbon radical having the number of carbon atoms indicated in the prefix and containing at least one triple bond. For example, $(C_2-C_6)$alkynylene is meant to include ethynylene, propynylene, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —R$^a$C(O)R$^b$ where R$^a$ is an alkylene group as defined above and R$^b$ is an alkoxy group as defined above, e.g., methoxycarbonylethyl, ethoxycarbonylbutyl, and the like.

"Aryl" means a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Aralkyl" means a radical —R$^a$R$^b$ where R$^a$ is an alkylene group (having six or fewer main chain carbon atoms) and R$^b$ is an aryl group as defined herein, e.g., benzyl, phenylethyl, 3-(3-chlorophenyl)-2-methylpentyl, and the like.

"Aralkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group and R$^b$ is an aryl group as defined herein, e.g., 2-hydroxy-2-phenyl-ethyl, 2-hydroxy-1-hydroxymethyl-2-phenyl-ethyl, and the like.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkyl-alkyl" means a radical —$R^aR^b$ where $R^a$ is an alkylene group and $R^b$ is a cycloalkyl group as defined herein, e.g., cyclopropylmethyl, cyclohexylpropyl, 3-cyclohexyl-2-methylpropyl, and the like. The prefix indicating the number of carbon atoms (e.g., $C_4$–$C_{10}$) refers to the total number of carbon atoms from both the cycloalkyl portion and the alkyl portion.

"Haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, —$OR^a$, —$NR^bR^c$, and —$S(O)_nR^d$ (where n is an integer from 0 to 2), with the understanding that the point of attachment of the heteroalkyl radical is through a carbon atom of the heteroalkyl radical. $R^a$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. $R^b$ is hydrogen, alkyl, cycloalkyl, cycloalkyl-alkyl, aryl or aralkyl. $R^c$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. $R^d$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^a$, $R^b$, $R^c$, and $R^d$ can be further substituted by $NH_2$, fluorine, alkylamino, di-alkylamino, OH or alkoxy. Additionally, the prefix indicating the number of carbon atoms (e.g., $C_1$–$C_{10}$) refers to the total number of carbon atoms in the portion of the heteroalkyl group exclusive of the cyano, —$OR^a$, —$NR^bR^c$, or —$S(O)_nR^d$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, alkylthio, amino, acylamino, mono-alkylamino, di-alkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or $(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —$R^aR^b$ where $R^a$ is an alkylene group and $R^b$ is a heteroaryl group as defined herein, e.g., pyridin-3-ylmethyl, 3-(benzofuran-2-yl)propyl, and the like.

"Heteroaralkenyl" means a radical —$R^aR^b$ where $R^a$ is an alkenylene group and $R^b$ is a heteroaryl group as defined herein, e.g., 3-(pyridin-3-yl)propen-2-yl, and the like.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —$(CR'R'')_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —$(CR'R'')_n$—$CONR^aR^b$ (where n is an integer from 0 to 5, R' and R" are independently hydrogen or alkyl, $R^a$ and $R^b$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$–$C_{10}$) refers to the total number of carbon atoms in the portion of the cycloheteroalkyl or heterocyclyl group exclusive of the number of heteroatoms.

"Heterocyclylalkyl" or "cycloheteroalkyl-alkyl" means a radical —$R^aR^b$ where $R^a$ is an alkylene group and $R^b$ is a heterocyclyl group as defined herein, e.g., tetrahydropyran-2-ylmethyl, 4-methylpiperazin-1-ylethyl, 3-piperidinylmethyl, and the like.

"Heteroalkylene" means a linear saturated divalent hydrocarbon radical of one to six carbons or a branched saturated hydrocarbon radical of three to six carbon atoms with one, two or three substituents independently selected from —$OR^a$, $NR^bR^c$, and —$S(O)_nR^d$ (where n is an integer from 0 to 2) where, $R^a$, $R^b$, $R^c$, and $R^d$ are as defined herein for a heteroalkyl radical. Examples include, 2-hydroxyethan-1, 2-diyl, 2-hydroxypropan-1,3-diyl and the like.

"Heterosubstituted cycloalkyl" means a cycloalkyl group wherein one, two, or three hydrogen atoms are replaced by substituents independently selected from the group consisting of cyano, hydroxy, alkoxy, amino, acylamino, mono-alkylamino, di-alkylamino, or —$SO_nR$ (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl). Examples include 4-hydroxycyclohexyl, 2-aminocyclohexyl etc.

"Heteroalkyl substituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkyl substituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR R (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

Each of the above terms (e.g., "alkyl," "heteroalkyl," "aryl", "heteroaryl", etc.) is meant to include both substituted and unsubstituted forms of the indicated radical, unless otherwise indicated. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR'C(O)$_2$R', —NH—CNH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2 m'+1), where m' is the total number of carbon atoms in such radical. R', R" and R'" each independently refer to hydrogen, unsubstituted (C$_1$–C$_8$)alkyl and heteroalkyl, unsubstituted aryl, aryl substituted with 1–3 halogens, alkoxy or thioalkoxy groups, or aryl-(C$_1$–C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Preferably, the alkyl groups will have from 0–3 substituents, more preferably 0, 1, or 2 substituents, unless otherwise specified.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The terms "modulate", "modulation" and the like refer to the ability of a compound to increase or decrease the function and/or expression of IKK, where IKK function may include kinase activity and/or protein-binding. Modulation may occur in vitro or in vivo. Modulation, as described herein, includes the inhibition or activation of IKK function and/or the downregulation or upregulation of IKK expression, either directly or indirectly. A modulator preferably activates IKK function and/or upregulates IKK expression. More preferably, a modulator activates or inhibits IKK function and/or upregulates or downregulates IKK expression. Most preferably, a modulator inhibits IKK function and/or downregulates IKK expression. The ability of a compound to inhibit IKK function can be demonstrated in an enzymatic assay or a cell-based assay (e.g., inhibition of IL-1-stimulated NF-κB activation).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrug" means any compound which releases an active parent drug according to formula I in vivo when such prodrug is administered to a mammalian subject. Prodrugs of a compound of formula I are prepared by modifying functional groups present in the compound of formula I in such a way that the modifications may be cleaved in vivo to release the parent compound. Prodrugs include compounds of formula I wherein a hydroxy, amino, or sulfhydryl group in a compound of formula I is bonded to any group that may be cleaved in vivo to regenerate the free hydroxyl, amino, or sulfhydryl group, respectively A wide variety of prodrug derivatives are known in the art, such as those that rely on hydrolytic cleavage or oxidative activation of the prodrug. Examples of prodrugs include, but are not limited to esters (e.g., acetate, formate, and benzoate derivatives), carbamates (e.g., N,N-dimethylaminocarbonyl) of hydroxy functional groups in compounds of formula I, and the like. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disease includes:

(1) alleviating or abrogating a disease and/or its attendant symptoms, (2) barring a subject from acquiring a disease (3) reducing a subject's risk of acquiring a disease, (4) decreasing the probability or eliminating the possibility that a disease will be contracted, (5) preventing the disease, i.e., causing the clinical symptoms of the disease not to develop in a mammal that may be exposed to or predisposed to the disease but does not yet experience or display symptoms of the disease, (6) inhibiting the disease, i.e., arresting or reducing the development of the disease or its clinical symptoms, or (7) relieving the disease, i.e., causing regression of the disease or its clinical symptoms.

As used herein, the term "IKK-mediated condition or disease" and related terms and phrases refer to a condition or disorder characterized by inappropriate, e.g., less than or greater than normal, IKK activity. Inappropriate IKK functional activity might arise as the result of IKK expression in cells which normally do not express IKK, increased IKK expression (leading to, e.g., inflammatory and immunoregulatory disorders and diseases) or decreased IKK expression. An IKK-mediated condition or disease may be completely or partially mediated by inappropriate IKK functional activity. However, an IKK-mediated condition or disease is one in which modulation of IKK results in some effect on the underlying condition or disorder (e.g., an TKK inhibitor results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "structural isomers" or "constitutional isomers". Isomers that differ in the sequence of bonding of their atoms are termed "positional isomers". For example, compounds of the formula A-C(O)—N($R^1$)—B and compounds of the formula A-N(R$^1$)—C(O)—B, where A and B are independenty (monovalent hydrocarbon radicals, are constitutional isomers. Unless otherwise indicated, the description is intended to include individual positional isomers.

Isomers that differ in the arrangement of their atoms in space are termed "configurational isomers" or "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of March, *Advanced Organic Chemistry*, 4th edition, John Wiley and Sons, New York, 1992).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabled compounds are useful as therapeutic agents, e.g., cancer therapeutic agents, research reagents, e.g., binding assay reagents, and diagnostic agents, e.g., in vivo imaging agents. All isotopic variations of the compounds of the present invention, whether radioactive or not, are intended to be encompassed within the scope of the present invention.

Embodiments of the Invention

Compounds

In one aspect, the present invention provides compounds useful in the treatment of inflammatory, metabolic or malignant conditions, having the formula (I):

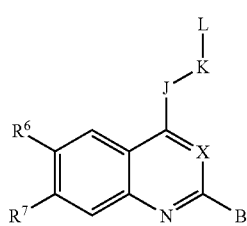

I or a pharmaceutically acceptable salt or prodrug thereof.

In formula I, X represents N or CR$^5$. In one group of embodiments, X is CR$^5$. In preferred embodiments, X is CH. In another group of embodiments, X is N.

is selected from (C$_1$–C$_4$)alkylene, (C$_2$–C$_4$)alkenylene, (C$_2$–C$_4$)alkynylene, C(=Y), NR$^1$, O, S(O)$_m$, C(=Y)NR$^1$, (C$_1$–C$_4$)alkylene-NR$^1$, (C$_1$–C$_4$)alkylene-O and C(R$^2$)=N.

In one group of embodiments, J is (C$_1$–C$_4$)alkylene. In preferred embodiments, J is methylene. In particularly preferred embodiments, J is CH$_2$.

In another group of embodiments, J is ethylene. In preferred embodiments, J is CH$_2$—CH$_2$.

In another group of embodiments, J is (C$_2$–C$_4$)alkenylene. In preferred embodiments, J is ethenylene. In particularly preferred embodiments, J is CH=CH.

In another group of embodiments, J is (C$_2$–C$_4$)alkynylene. In preferred embodiments, J is ethynylene.

In another group of embodiments, J is C(=Y). In preferred embodiments, J is C(O).

In another group of embodiments, J is NR$^1$. In preferred embodiments, J is NH.

In another group of embodiments, J is O.

In another group of embodiments, J is S(O)$_m$. In one group of preferred embodiments, J is SO$_2$. In another group of preferred embodiments, J is S.

In another group of embodiments, J is C(=Y)NR$^1$. In preferred embodiments, J is C(O)NR$^1$. In particularly preferred embodiments, J is C(O)NH.

In another group of embodiments, (C$_1$–C$_4$)alkylene-NR$^1$. In preferred embodiments, J is methylene-NR$^1$. In one group of particularly preferred embodiments, J is CH$_2$—NR$^1$. In more particularly preferred embodiments, J is CH$_2$—NH.

In another group of embodiments, J is (C$_1$–C$_4$)alkylene-OR$^1$. In preferred embodiments, J is methylene-OR$^1$. In particularly preferred embodiments, J is CH$_2$—OR$^1$.

In another group of embodiments, J is C(R$^2$)=N. In preferred embodiments, J is CH=N.

K is selected from a bond, (C$_1$–C$_4$)alkylene, C(=Y), NR$^1$, O and S(O)$_m$. In one group of embodiments, K is a bond.

In another group of embodiments, K is (C$_1$–C$_4$)alkylene. In preferred embodiments, K is methylene. In particularly preferred embodiments, K is CH$_2$.

In another group of embodiments, K is C(=Y). In preferred embodiments, K is C(O).

In another group of embodiments, K is NR$^1$. In preferred embodiments, K is NH.

In another group of embodiments, K is O.

In another group of embodiments, K is S(O)$_m$. In one group of preferred embodiments, K is SO$_2$. In another group of preferred embodiments, K is S.

L is selected from H, (C$_1$–C$_6$)alkyl, OR$^1$, hetero(C$_1$–C$_6$)alkyl, aryl, heteroaryl, NR$^2$R$^3$, C(=Y)R$^2$, C(=y)NR$^2$R$^3$, C(=Y)OR$^2$, (C$_1$–C$_4$)alkylene-C(=Y)R$^2$, (C$^1$–C$_4$)alkylene-C(=Y)NR$^2$R$^3$ and (C$_1$–C$_4$)alkylene-C(=Y)OR$^2$. In one group of embodiments, L is aryl or heteroaryl. In preferred embodiments, L is selected from phenyl, naphthyl, pyrrolyl, pyrazolyl, imidazolyl, pyrazinyl, oxazolyl, isoxazolyl, thiazolyl, furyl, thienyl, pyridyl, pyrimidyl, pyrimidinyl, pyridazinyl, benzothiazolyl, purinyl, benzimidazolyl, indolyl, isoquinolyl, quinoxalinyl and quinolyl.

In another group of embodiments, L is (C$_1$–C$_6$)alkyl.

In another group of embodiments, L is selected from C(=Y)R$^2$, C(=Y)NR$^2$R$^3$ and CO$_2$R$^2$. In preferred embodiments L is C(O)NR$^2$R$^3$. In particularly preferred embodiments, L is C(O)NH$_2$.

Optionally, J may be combined with K or L to form a 5-, 6-, 7- or 8-membered ring containing from 0 to 3 heteroatoms selected from N, O and S.

Optionally, K may be combined with L to form 5-, 6-, 7-or 8-membered ring containing from 0 to 3 heteroatoms selected from N, O and S.

B is a five- or six-membered aromatic ring system containing at least one heteroatom selected from the group consisting of N, O and S. In preferred embodiments, B is selected from 1-methylimidazol-5-yl, 1-(trifluoromethyl) imidazol-5-yl, 5-methylimidazol-1-yl, 5-(trifluoromethyl) imidazol-1-yl, thiazol-5-yl, imidazol-1-yl, 1,3,4-triazol-1-yl, 1,2,4-triazol-4-yl, thienyl, furyl and pyridyl. In particularly preferred embodiments, B is selected from 1-methylimidazol-5-yl, 5-methylimidazol-1-yl, thiazol-5-yl, imidazol-1-yl and 1,3,4-triazol-1-yl.

Y is selected from O, S, $NR^1$, N(CN) and $NOR^1$.

$R^1$, $R^2$ and $R^3$ independently represent H, $(C_1-C_{10})$alkyl, $(C_3-C_{10})$alkenyl, $(C_2-C_{10})$alkynyl, $(C_1-C_{10})$heteroalkyl, $(C_3-C_{10})$cycloalkyl, $(C_3-C_{10})$cycloalkyl-alkyl, $(C_3-C_{10})$cyclohereroalkyl-alkyl, $(C_3-C_{10})$cyclohereroalkyl, aryl, aryl $(C_1-C_4)$alkyl, aryl$(C_1-C_4)$heteroalkyl, heteroaryl$(C_1-C_4)$ alkyl, heteroaryl$(C_1-C_4)$heteroalkyl or fluoro$(C_1-C_6)$alkyl.

Optionally, when $R^2$ and $R^3$ are attached to the same nitrogen atom, $R^2$ and $R^3$ may be combined with the nitrogen atom to form a 5-, 6- or 7-membered ring containing from 1 to 3 heteroatoms selected from N, O and S.

$R^5$, $R^6$ and $R^7$ are independently selected from H, halogen, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$ alkylamino, $(C_3-C_{10})$cycloalkyl, $(C_3-C_{10})$cycloalkyl-alkyl, $(C_3-C_{10})$cyclohereroalkyl, $(C_3-C_{10})$cyclohereroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N$[(C_1-C_6)$alkyl$]_2$, $SO_2NH_2$, $SO_2NH$—$(C_1-C_6)$alkyl, $SO_2N$—$[(C_1-C_6)$alkyl$]_2$ and $(C_1-C_6)$heteroalkoxy.

Optionally, $R^6$ and $R^7$ may be combined to form a new 5- or 6-membered fused ring containing from 0 to 3 heteroatoms selected from N, O and S.

The subscript m is an integer of from 0 to 2.

Compounds having the formula:

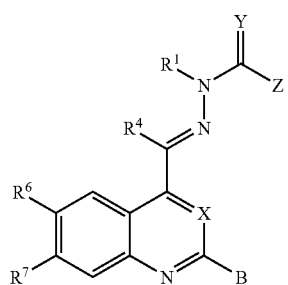

wherein Z is selected from H, $(C_1-C_{10})$alkyl, $(C_3-C_{10})$ cycloalkyl, $(C_3-C_{10})$cycloalkyl-alkyl, $(C_2-C_{10})$alkenyl, $(C_2-C_{10})$alkynyl and $NR^2R^3$ and $R^4$ is selected from H, $(C_1-C_{10})$alkyl, $(C_3-C_6)$cycloalkyl, $(C_4-C_7)$ cycloalkyl-alkyl, $(C_2-C_6)$alkenyl and $(C_2-C_6)$alkynyl are excluded from the present invention.

The invention also provides compounds having the formula (I):

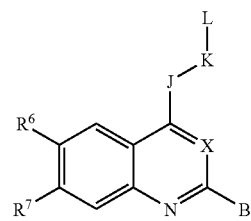

or a pharmaceutically acceptable salt or prodrug thereof, wherein

K is selected from the group consisting of a bond, $(C_1-C_4)$alkylene, C(=Y), $NR^1$, O and $S(O)_m$. The variables X, J, L, B, Y, $R^1$, $R^2$, $R^3$, $R^4$, $R^5$, $R^6$, $R^7$ and m have the meanings and preferred groupings provided above. In one group of embodiments, K is a bond. In another group of embodiments, K is $(C_1-C_4)$alkylene. In preferred embodiments, K is methylene (—$CH_2$—). In another group of embodiments, K is C(=Y). In preferred embodiments, K is C(O). In another group of embodiments, K is $NR^1$. In preferred embodiments, K is NH. In another group of embodiments, K is O. In another group of embodiments, K is $S(O)_m$. In one group of preferred embodiments, K is $SO_2$. In another group of preferred embodiments, K is S.

The invention also provides compounds having the formula (I):

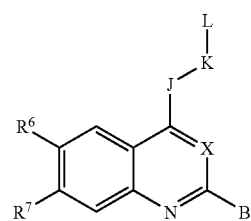

or a pharmaceutically acceptable salt or prodrug thereof, wherein L is selected from the group consisting of H, $(C_1-C_6)$alkyl, $OR^1$, hetero$(C_1-C_6)$alkyl, aryl, heteroaryl, $NR^2R^3$, C(=Y)$OR^2$, $(C_1-C_4)$alkylene-C(=Y)$NR^2R^3$, $(C_1-C_4)$alkylene-C(—Y)$R^2$ and $(C_1-C_4)$alkylene-C(=Y) $OR^2$. The remaining variables have the meanings and preferred groupings provided above. In one group of embodiments, L is aryl or heteroaryl. In preferred embodiments, L is selected from phenyl, naphthyl, pyrrolyl, pyrazolyl, imidazolyl, pyrazinyl, oxazolyl, isoxazolyl, thiazolyl, furyl, thienyl, pyridyl, pyrimidyl, pyrimidinyl, pyridazinyl, benzothiazolyl, purinyl, benzimidazolyl, indolyl, isoquinolyl, quinoxalinyl and quinolyl. In another group of embodiments, L is $(C_1-C_6)$alkyl. In another group of embodiments, L is selected from C(=Y)$R^2$, C(=Y)$NR^2R^3$ and $CO_2R^2$. In preferred embodiments L is C(O)$NR^2R^3$. In particularly preferred embodiments, L is C(O)$NH_2$.

The invention also provides compounds having the formula (I):

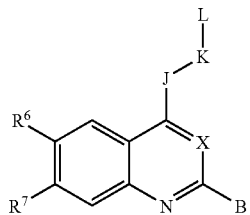

I or a pharmaceutically acceptable salt or prodrug thereof, wherein J is selected from the group consisting of $(C_1-C_4)$ alkylene, $(C_2-C_4)$alkenylene, $(C_2-C_4)$alkynylene, $C(=Y)$, $NR^1$, O, $S(O)_m$, $C(=Y)NR^1$, $(C_1-C_4)$alkylene-$NR^1$ and $(C_1-C_4)$alkylene-O. The remaining variables have the meanings and preferred groupings provided above. In one group of embodiments, J is $(C_1-C_4)$alkylene, more preferably, J is methylene. In another group of embodiments, J is ethylene. In another group of embodiments, J is $(C_2-C_4)$alkenylene, more preferably ethenylene (—CH=CH—). In another group of embodiments, J is $(C_2-C_4)$alkynylene, more preferably ethynylene. In still another group of embodiments, J is $C(=Y)$, more preferably J is $C(O)$. In yet another group of embodiments, J is $NR^1$, more preferably NH. In still another group of embodiments, J is O. In yet another group of embodiments, J is $S(O)_m$. In one group of preferred embodiments, J is $SO_2$. In another group of preferred embodiments, J is S.

In another group of embodiments, J is $C(=Y)NR^1$. In preferred embodiments, J is $C(O)NR^1$.

In particularly preferred embodiments, J is $C(O)NH$. In another group of embodiments, J is $(C_1-C_4)$alkylene-$NR^1$. In preferred embodiments, J is methylene-$NR^1$. In one group of particularly preferred embodiments, J is $CH_2$—$NR^1$. In more particularly preferred embodiments, J is $CH_2$—NH. In another group of embodiments, J is $(C_1-C_4)$alkylene-$OR^1$. In preferred embodiments, J is methylene-$OR^1$. In particularly preferred embodiments, J is $CH_2$—$OR^1$. In another group of embodiments, J is $C(R^2)=N$. In preferred embodiments, J is CH=N.

One group of embodiments has the formula:

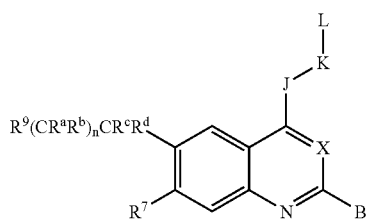

IIa

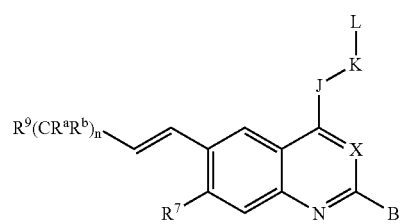

IIb

In formulas IIa and IIb, $R^9$ is selected from CN, $S(O)_p(C_1-C_6)$alkyl and $(C_1-C_6)$alkoxy, wherein the subscript p is an integer of from 0 to 2.

$R^a$, $R^b$, $R^c$ and $R^d$ are independently selected from the group consisting of H, halogen, $(C_1-C_6)$alkyl, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N[$(C_1-C_6)$alkyl]$_2$, $SO_2NH_2$, $SO_2NH$—$(C_1-C_6)$alkyl, $SO_2N$—[$(C_1-C_6)$alkyl]$_2$ and $(C_1-C_6)$heteroalkoxy. In preferred embodiments, $R^a$, $R^b$, $R^c$ and $R^d$ are H.

The subscript n is an integer of from 0 to 3.

Preferred embodiments have the formula:

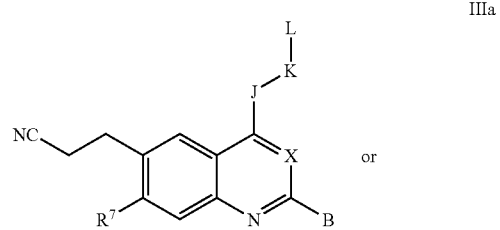

IIIa or

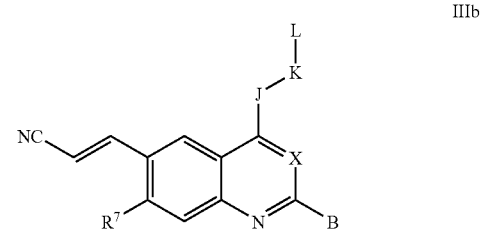

IIIb

Other preferred embodiments have the formula:

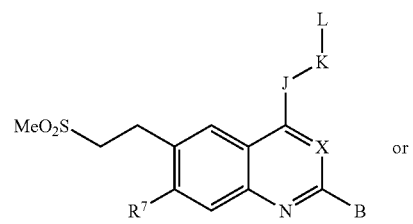

IVa or

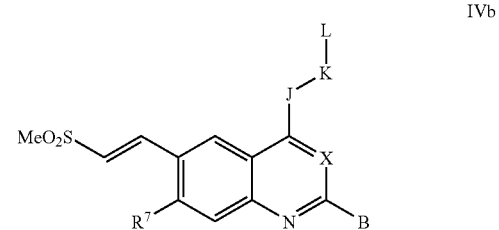

IVb

Still other preferred embodiments have the formula:

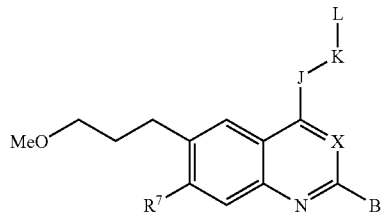
Va

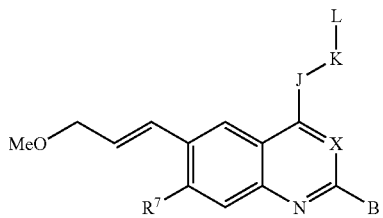
Vb

Particularly preferred embodiments have the formula:

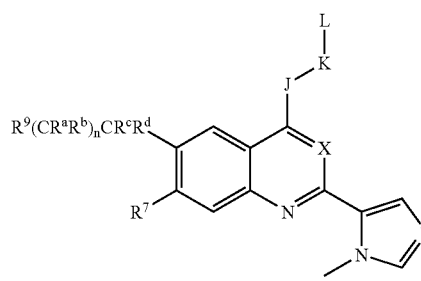
VIa

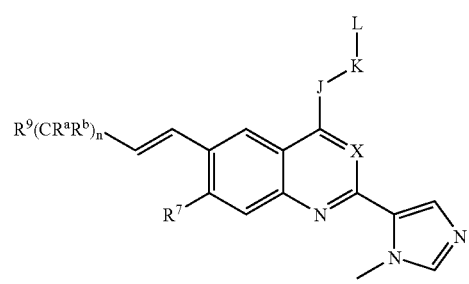
VIb

Other particularly preferred embodiments have the formula:

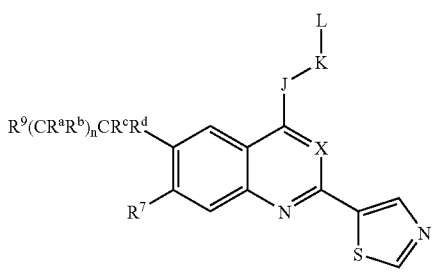
VIIa

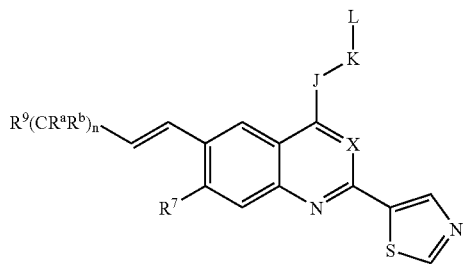
VIIb

Other particularly preferred embodiments have the formula:

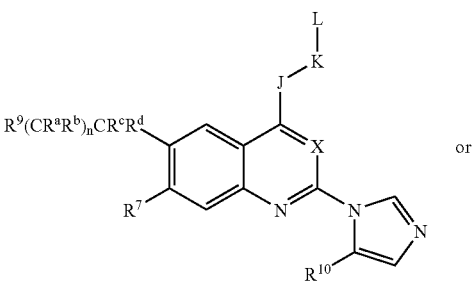
VIIIa

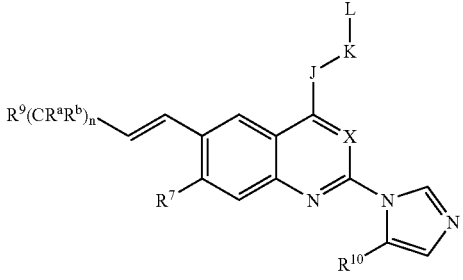
VIIIb

In formulas VIIIa and VIIIb, $R^{10}$ is selected from the group consisting of H, $(C_1-C_4)$alkyl, $(C_1-C_4)$fluoroalkyl, and halogen.

Other particularly preferred embodiments have the formula:

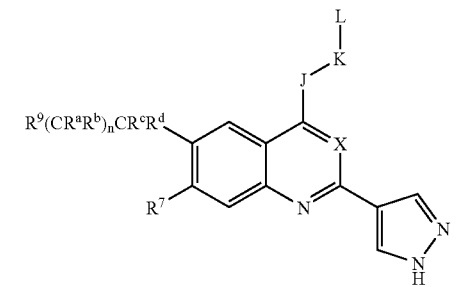
IXa

-continued

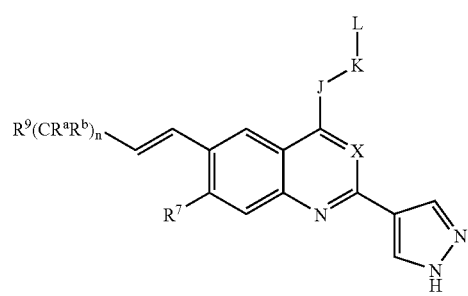

IXb

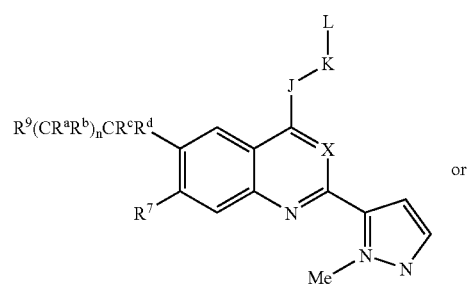

IXc

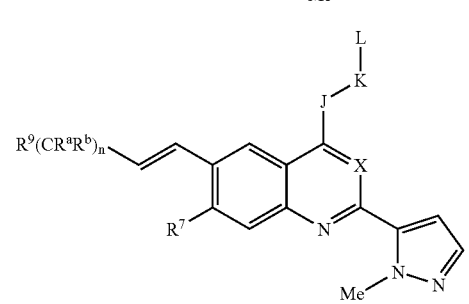

IXd $R^a$, $R^b$, $R^c$ and $R^d$ are each preferably H in the above embodiments.

Another group of embodiments has the formula (X):

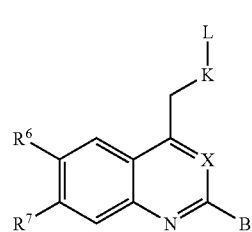

X

Another group of embodiments has the formula (XI):

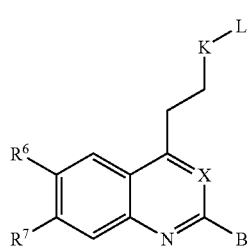

XI

Another group of embodiments has the formula (XII):

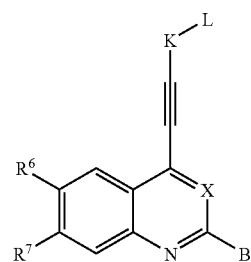

XII

In compounds of formula XII, K is preferably a bond.

Another group of embodiments has the formula (XIII):

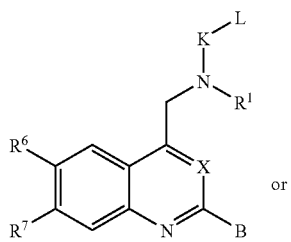

XIII

Another group of embodiments has the formula:

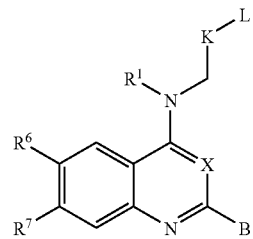

XVIa or

XVIb

Another group of embodiments has the formula (XV):

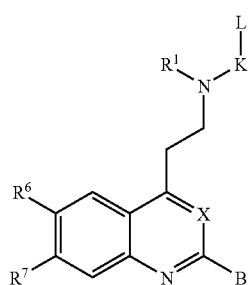

XV

Another group of embodiments has the formula (XVI):

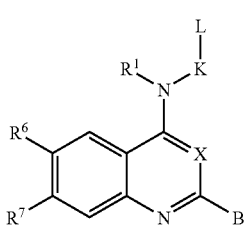

XVI

Another group of embodiments has the formula (XVII):

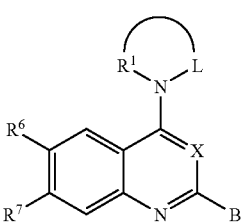

XVII

Another group of embodiments has the formula:

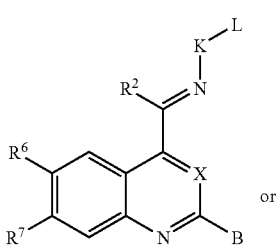

XVIIIa or

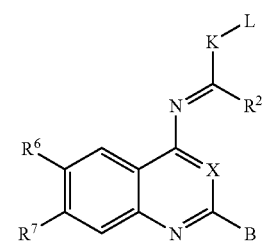

XVIIIb

In compounds of formulas XVIIIa and XVIIIb, R² is preferably H.

Another group of embodiments has the formula (XIX):

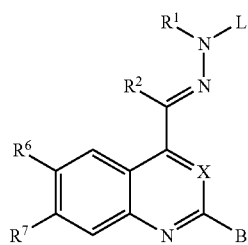

XIX

In compounds of formula XIX, R² is preferably H.

Another group of embodiments has the formula (XX):

XX

Another group of embodiments has the formula:

XXIa or

XXIb

Another group of embodiments has the formula (XXII):

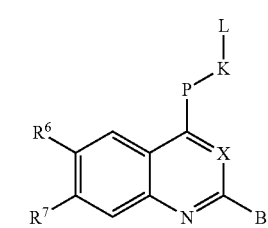

XXII

Another group of embodiments has the formula:

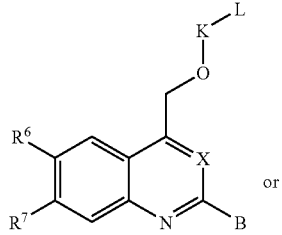

XXIIIa or

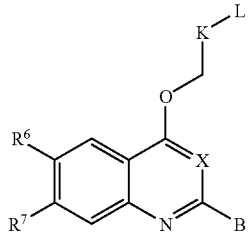

XXIIIb

Another group of embodiments has the formula (XXIV):

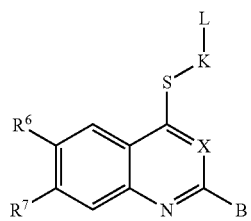

XXIV

Figure 1B:
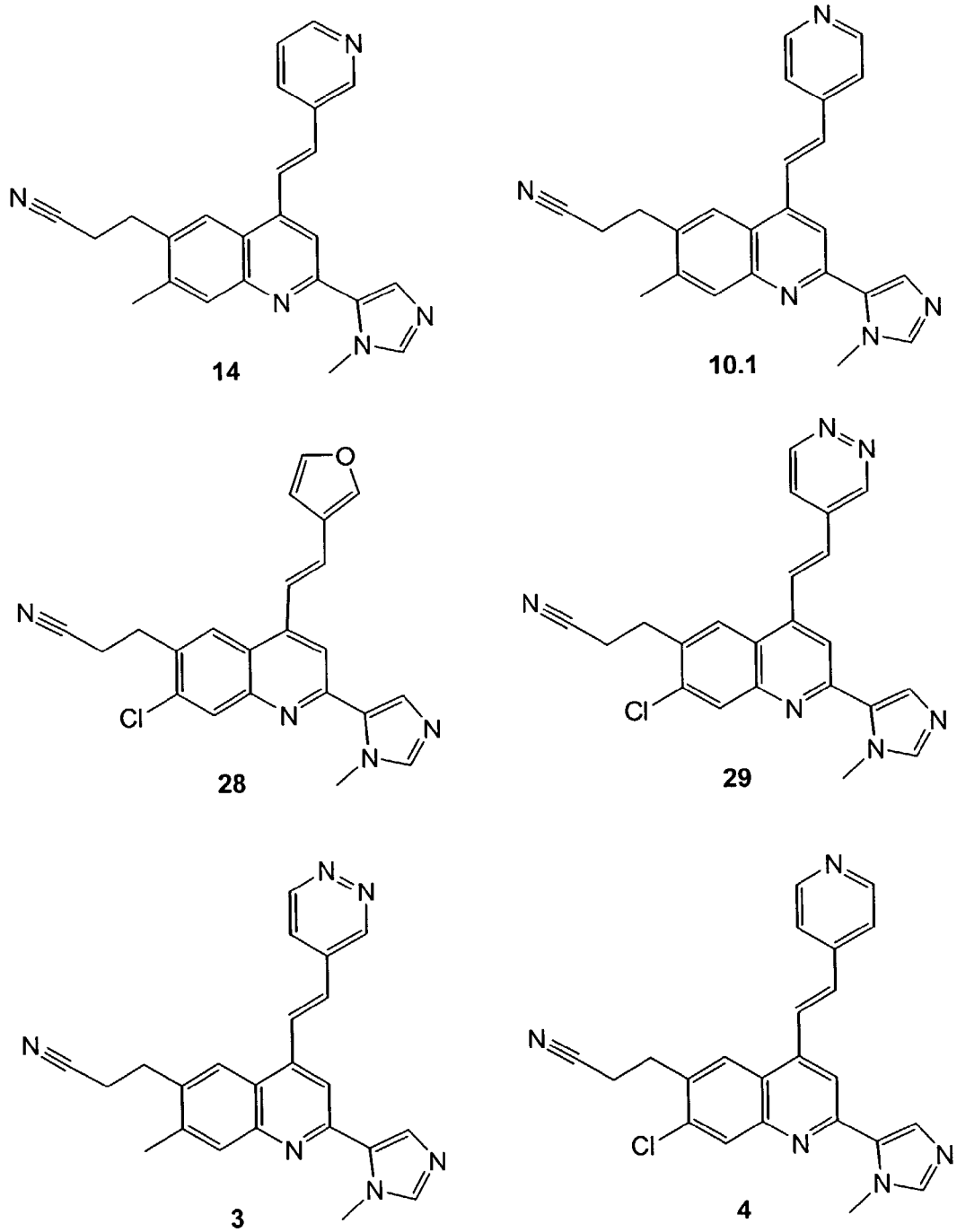
Figure 1C:
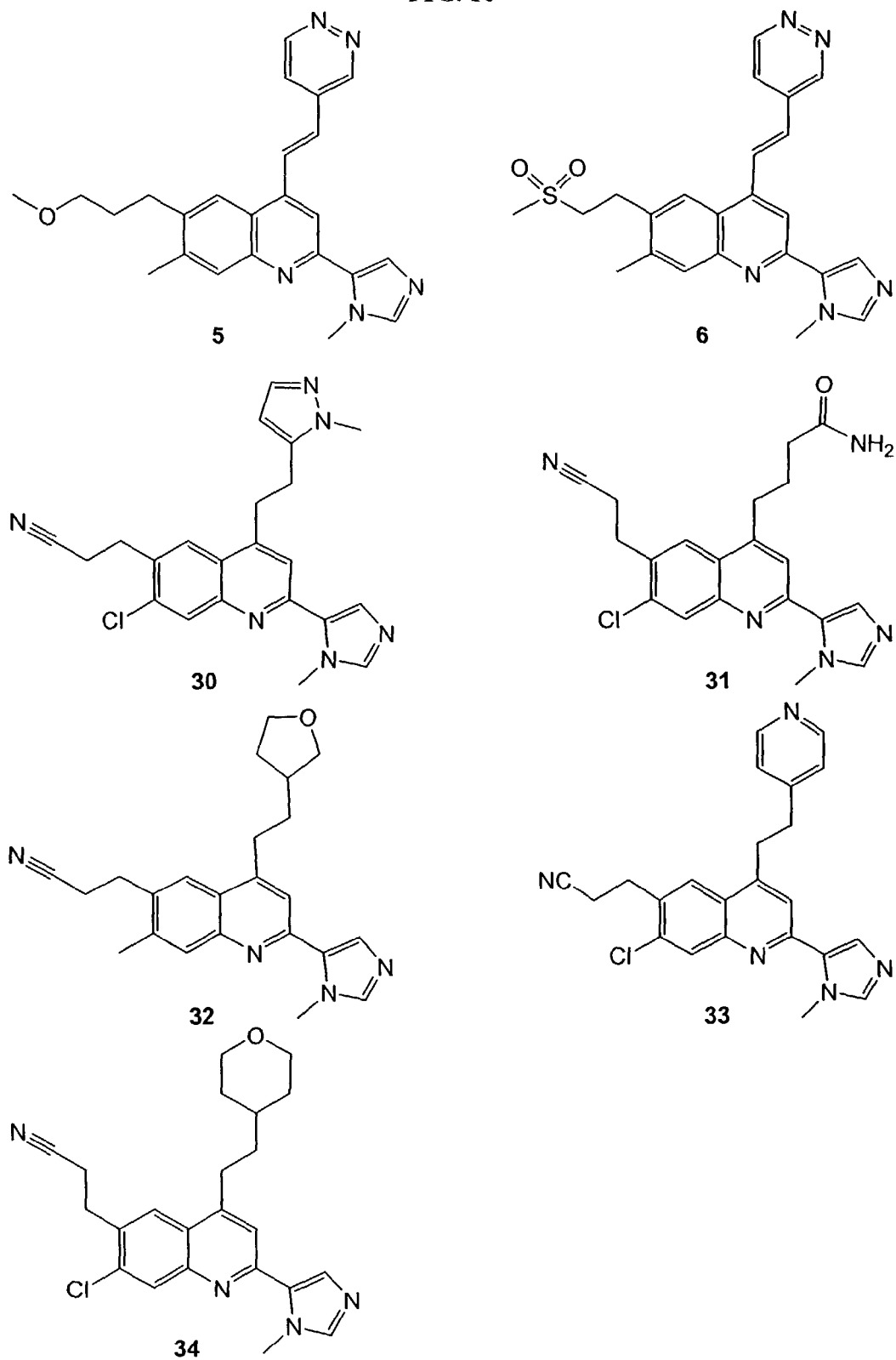
Figure 1D:
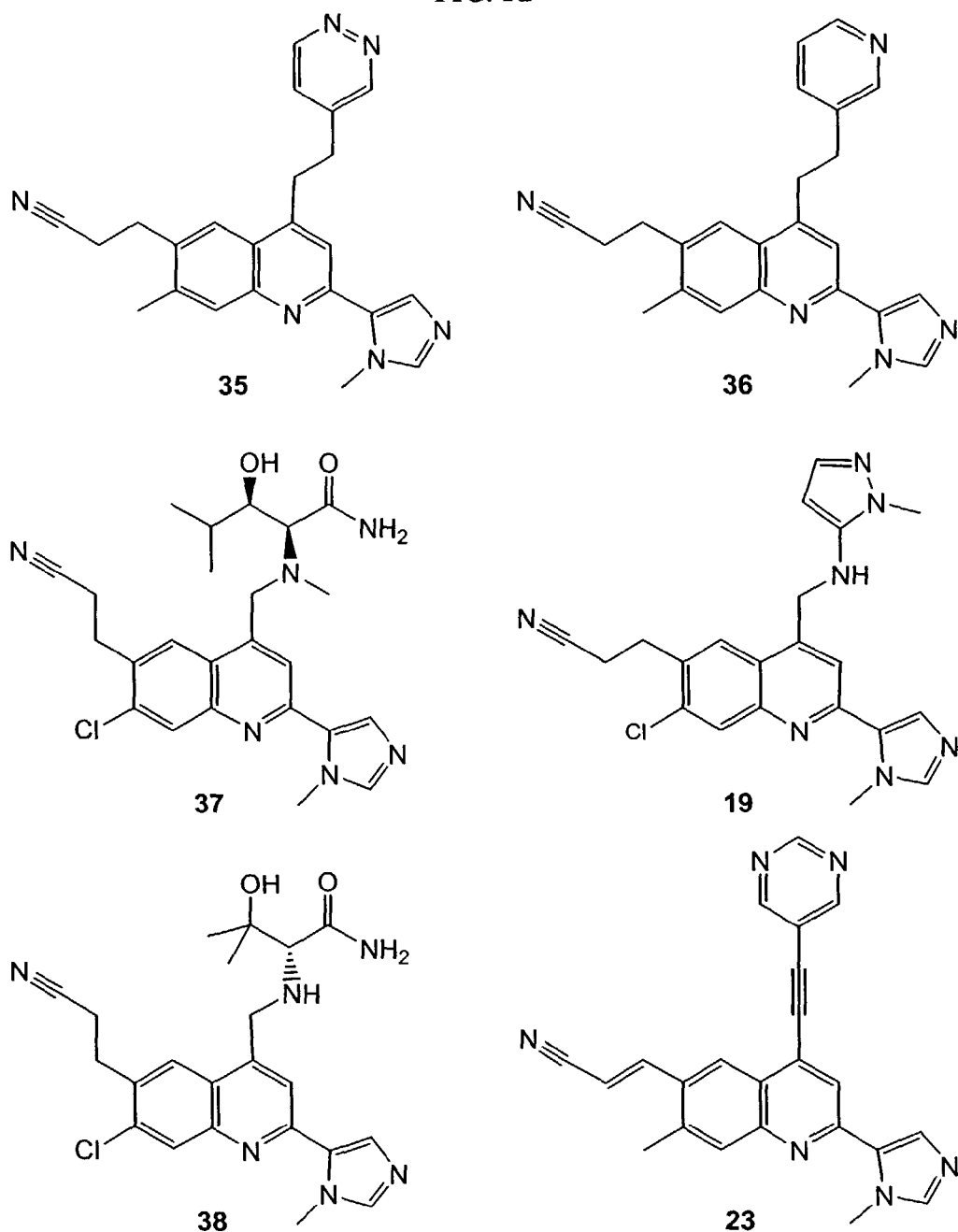
Figure 1E:
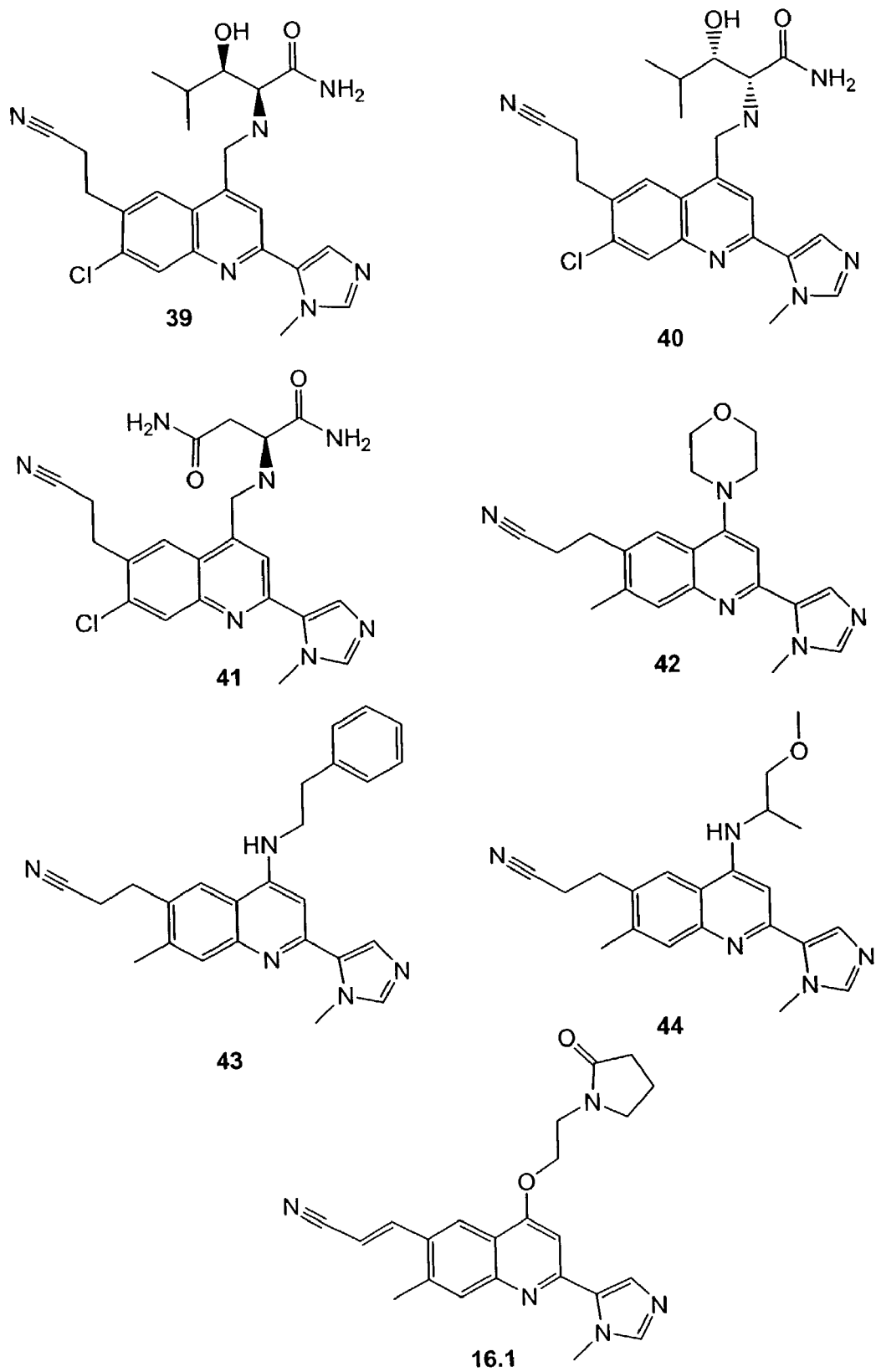
Figure 1F:
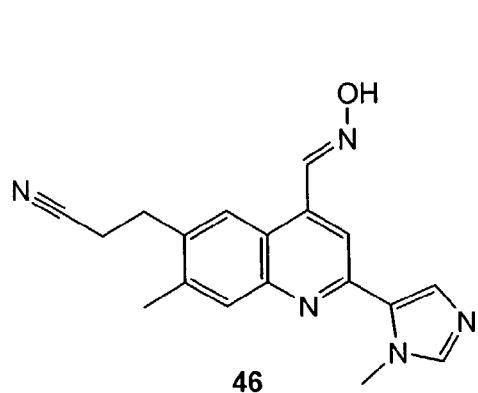
Figure 1F:
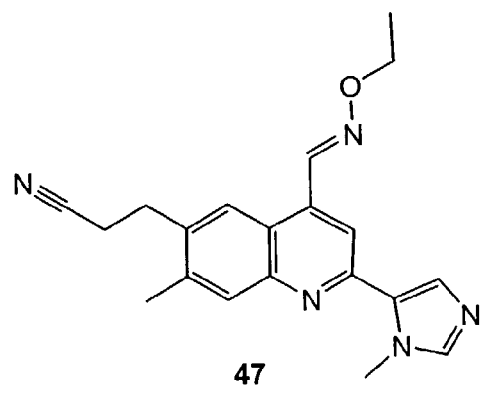
Figure 1F:
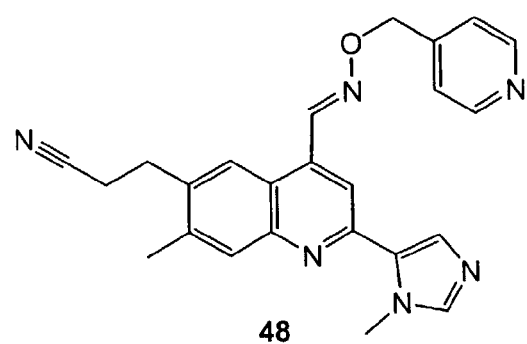
Figure 1F:
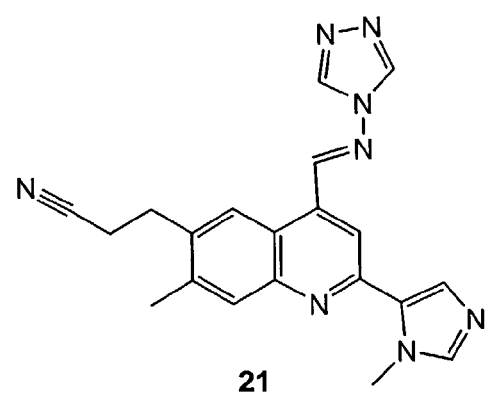
Figure 1F:
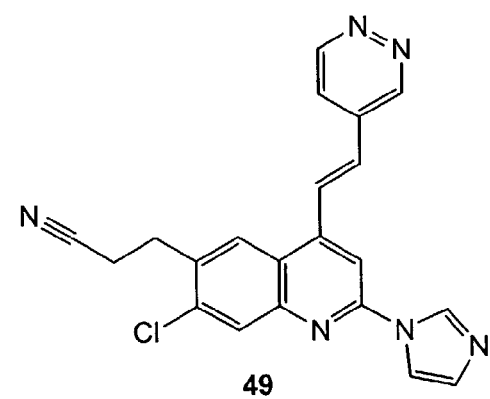
Figure 1F:
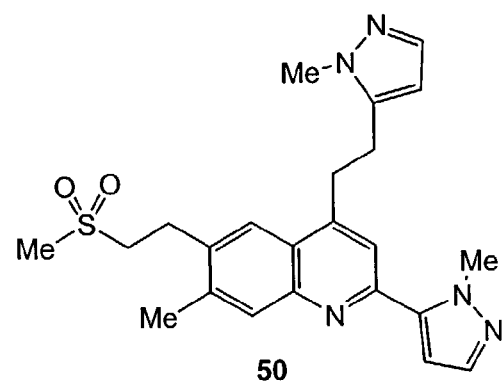
Figure 1G:
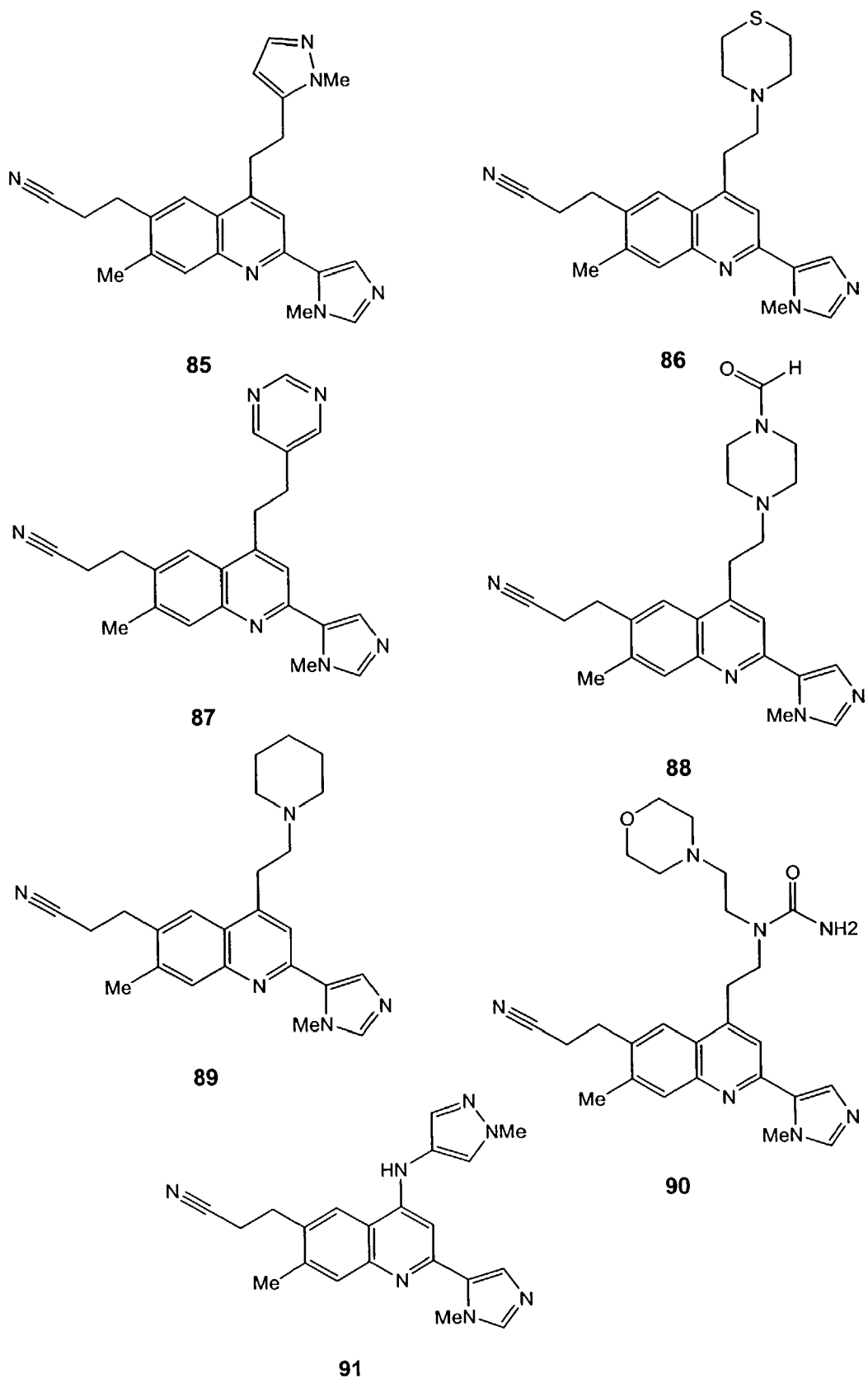

The structures of exemplary compounds of the invention are shown in FIG. 1.

Preparation of Compounds

Schemes 1–10 below provide exemplary synthetic methods for the preparation of the compounds of the present invention. One of skill in the art will understand that additional methods are also useful.

The synthesis of the compounds of the invention can be accomplished generally from an appropriate aldehyde (or ketone) ii. In some cases, the aldehyde (or ketone) may not be fully isolated and/or characterized, but may be synthesized from the corresponding ester or carboxylic acid i (Scheme 1) (or isatin (see, e.g., Scheme 2) or similar compound with the appropriate function group) and utilized directly in a reaction. In some cases, the aldehyde ii may be isolated as a mixture with the corresponding hemiacetal, e.g., if an alcohol such as methanol is used in its purification.

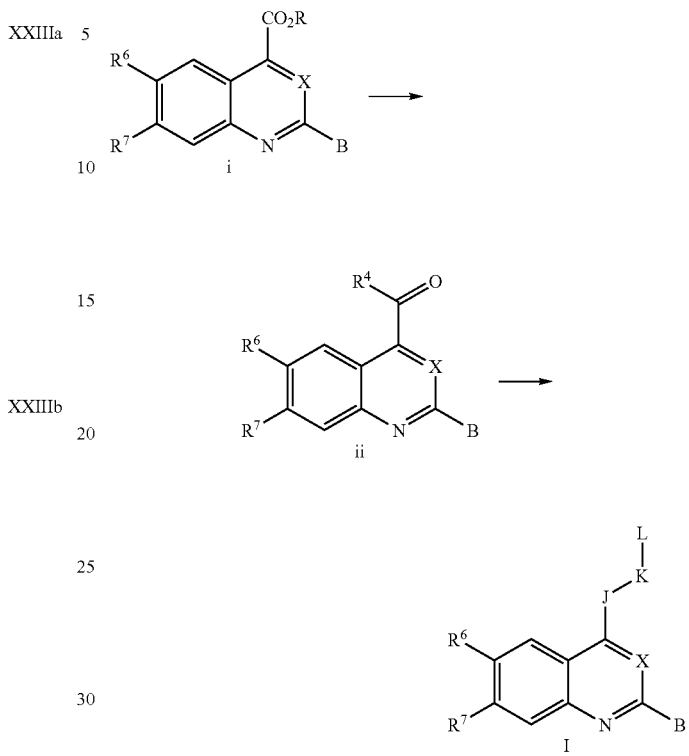

Scheme 1

Esters and acids i can be prepared by a variety of methods generally known to those skilled in the art of organic synthesis. Representative methods for the synthesis of esters i are provided in U.S. patent application Ser. No. 10/004,287, incorporated by reference herein.

Esters i can also be prepared by a variety of methods generally known to those skilled in the art of organic synthesis. Exemplary methods for synthesis of the aldehyde ii, where X is CH, are provided in Scheme 2 below. Isatin can react with a suitable methyl ketone or with malonic acid to afford the quinoline derivative i, after esterification. Conversion to, e.g., the chloride, bromide or triflate followed by nucleophilic displacement with ring B or Pd(0) catalyzed coupling with, for example, an arylboronic acid or arylstannane may also afford the quinoline derivative i.

A number of variably substituted isatins are available from commercial sources. Alternatively, literature methods describe their preparation from the corresponding anilines (or equivalent aromatic amines). For example, substituted isatins can be prepared via a Sandmeyer procedure (see, Garden et al. (1997) *Tetrahedron Lett.* 38(9):1501, and references cited therein); a formanilide method (see, Otto et al. (1996) *Tetrahedron Lett.* 37(52):9381); a Stolle type procedure (see Soll, et al. (1988) *J. Org. Chem.* 53:2844; a Stolle-Becker (oxalyl chloride) procedure (see, Baumgarten et al. (1961) *J. Org. Chem.* 26:1536); α keto amides (see, Fumiyuki et al. (1986) *J. Org. Chem.* 51:415); a Gassman method (see, Gassman et al. (1977) *J. Org. Chem.* 42(8): 1344); ortho-lithiated anilines (see, Hewawasam et al. (1994) *Tetrahedron Lett.* 35:7303; an oxindole route (see, Kraynack et al. (1998) *Tetrahedron Lett.* 39:7679); and via bis(alkylthio)carbenes (see Rigby, and Danca (1999) *Tetrahedron Lett.* 40:689).

Scheme 2

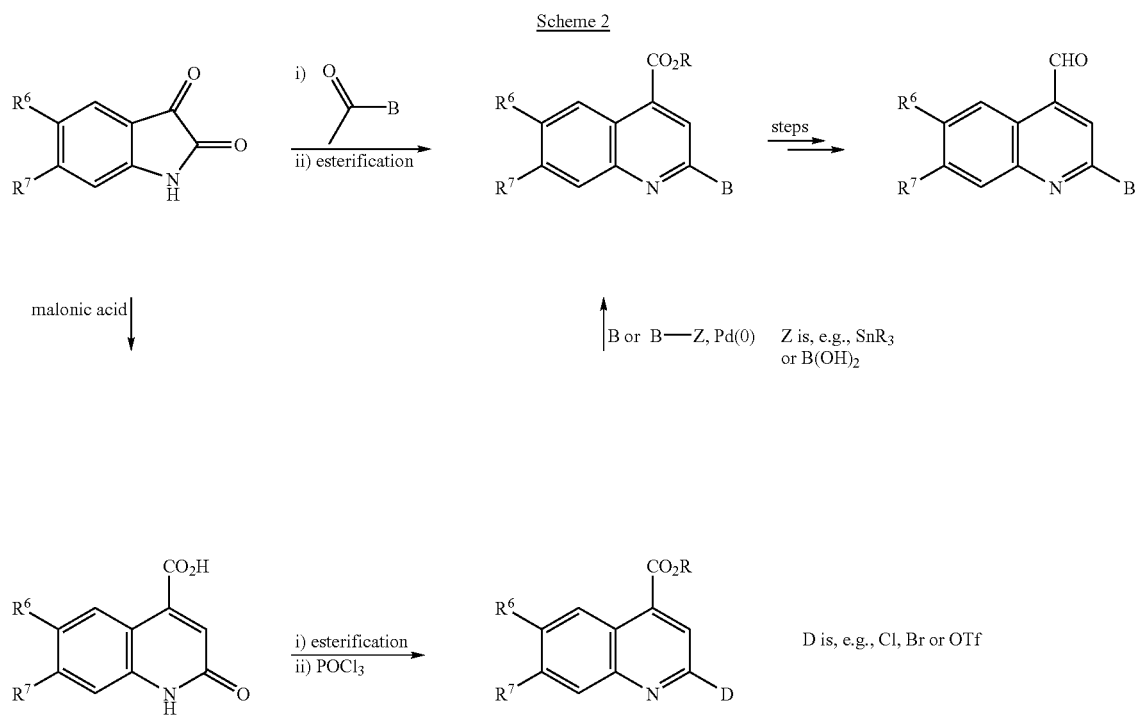

Schemes 3 and 4 illustrate procedures for the conversion of aldehyde ii into compounds of formula XII or XI. 4-Picoline, 2-picoline, 3-methylpyridazine, 2-methylpyridazine or a related compound, represented by Me-K-L in Scheme 3, may be condensed with aldehyde ii to afford a compound of formula XII (Method A), the condensation may be catalyzed by acetic anhydride, or related species, or a Lewis acid such as zinc chloride. Alternatively the anion of the above methylheteroaryl compounds, or similar species with acidic methyl groups, may be formed, for example with PhLi, and reacted with aldehyde ii to afford a compound of formula XII after dehydration. Alternatively, a Wittig (or a related reaction such as the Wadsworth-Emmons reaction of a dialkylphosphonate which will be familiar to those skilled in the art) may be employed (Method C).

The $C_2$ alkenyl tether of XII may be reduced by a variety of general methods familiar to those skilled in the art to afford compounds of formula XI. Representative examples are described, vide infra, and include hydrogenation in the presence of Pd/C or treatment with sodium borohydride or related species (Method B).

Scheme 3

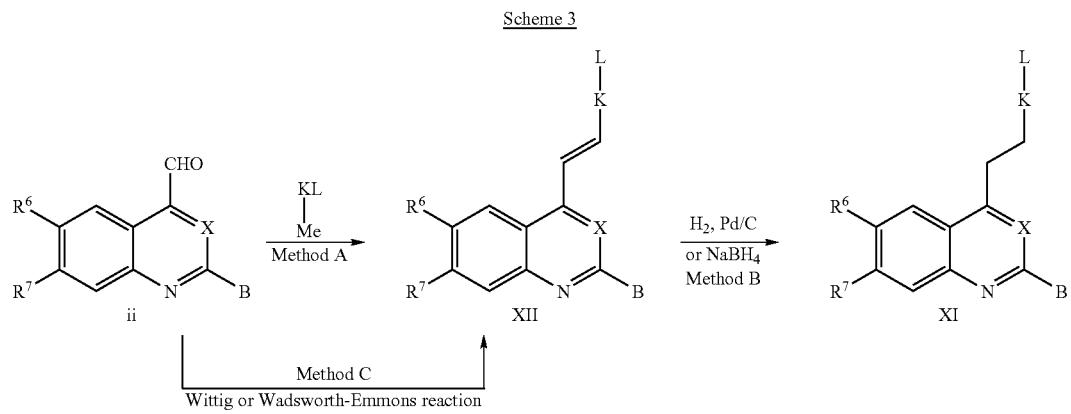

Scheme 4 provides additional non-limiting methods for the preparation of compounds of formula XII. In Methods D and E a Wittig reagent is prepared from iii and reacts with an aldehyde, represented by L-K—CHO in Scheme 4 to form methylene derivative XII. In Method F, derivative v can be condensed with an aldehyde, represented by L-K—CHO. In Method G, Pd(0) coupling of a derivative vi with a suitable partner such as a vinyl boronoic acid or vinylstannane. The preparation of alcohol iii has been described previously; see, e.g., U.S. patent Ser. No. 10/004,287, incorporated by reference herein.

Scheme 5 illustrates the conversion of derivative vii into compounds of formula XVI via displacement of a leaving group D with a nitrogen based nucleophile (Method H) or compounds of formula XXII via displacement of leaving group D with an oxygen based nucleophile (Method I). Alternative methods for the preparation of compounds of formulas XVI and XXII include, but are not restricted to, alkylation of amine viii (Method J) or alkylation of alcohol ix (Method K), respectively, by an alkylating agent D-K-L.

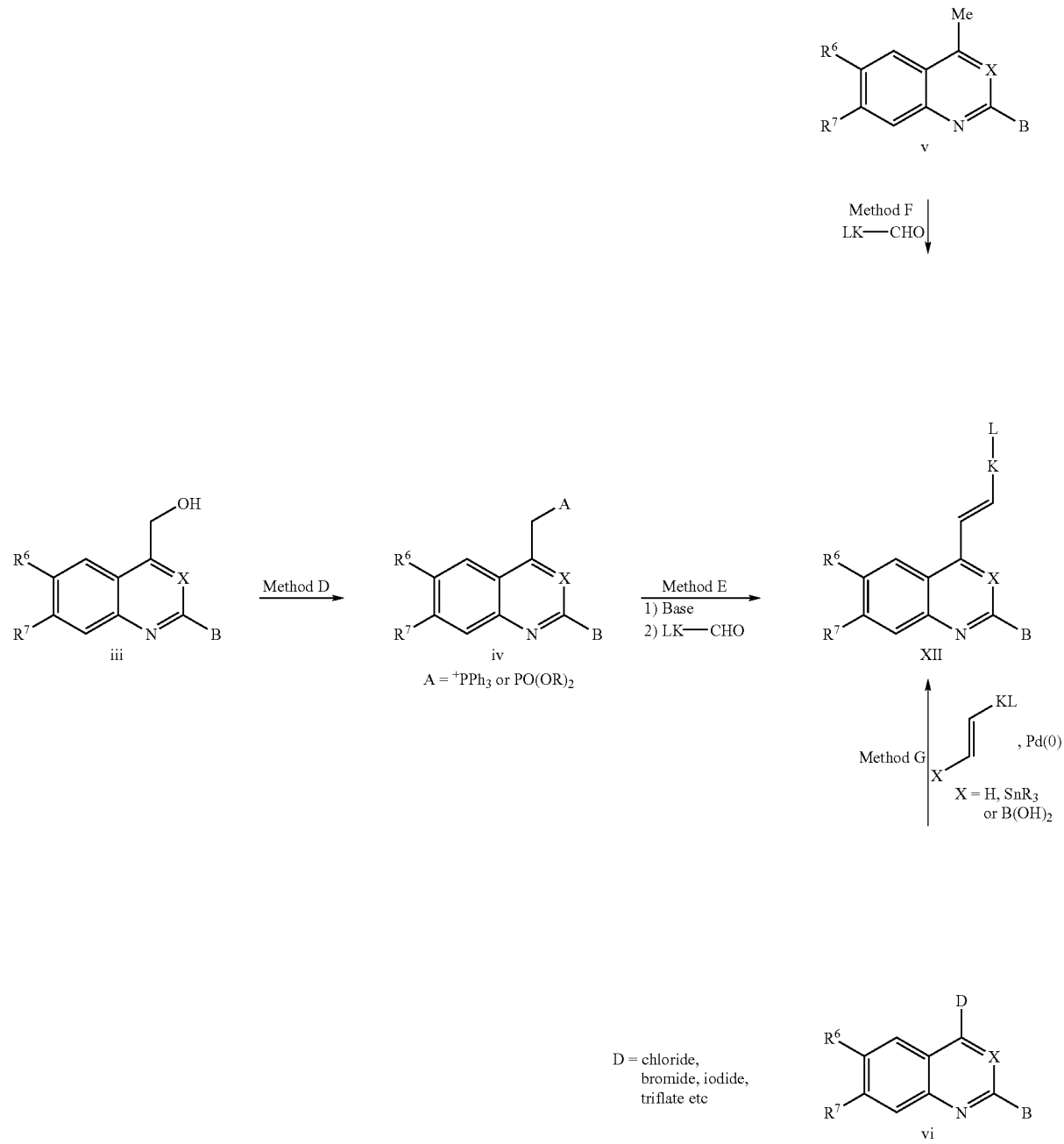

Scheme 5

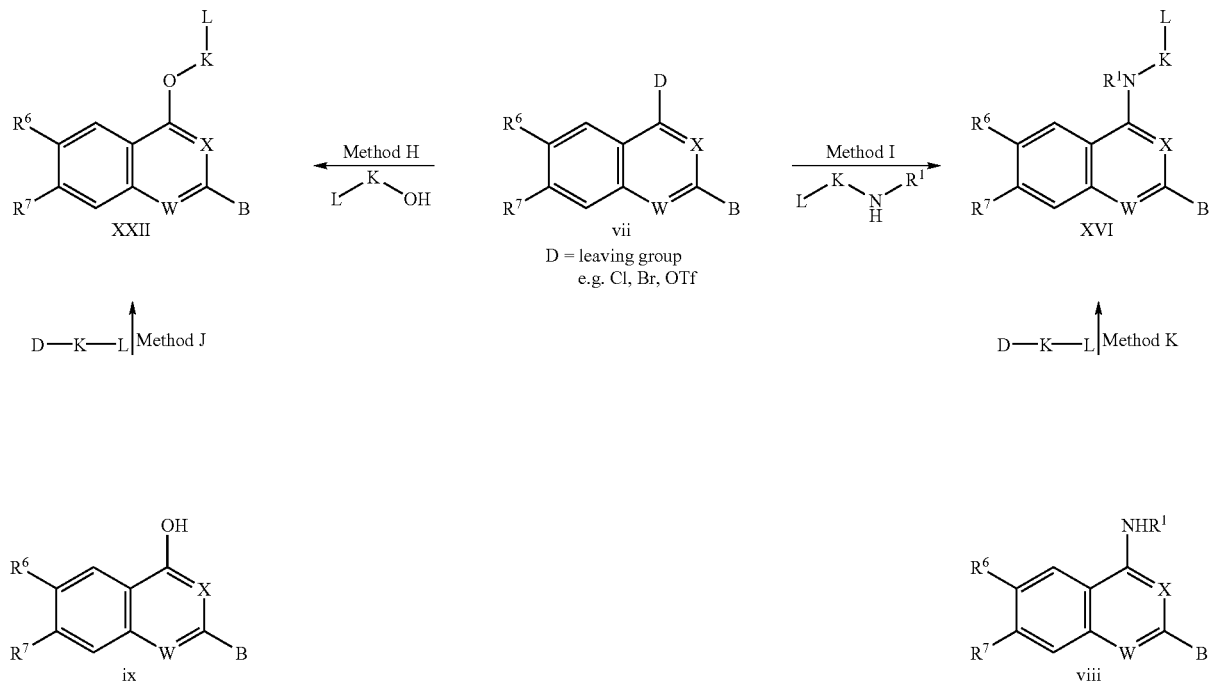

Compounds of formula XIVa may be prepared from the aldehyde ii by reductive amination (Method L), as outlined in Scheme 6.

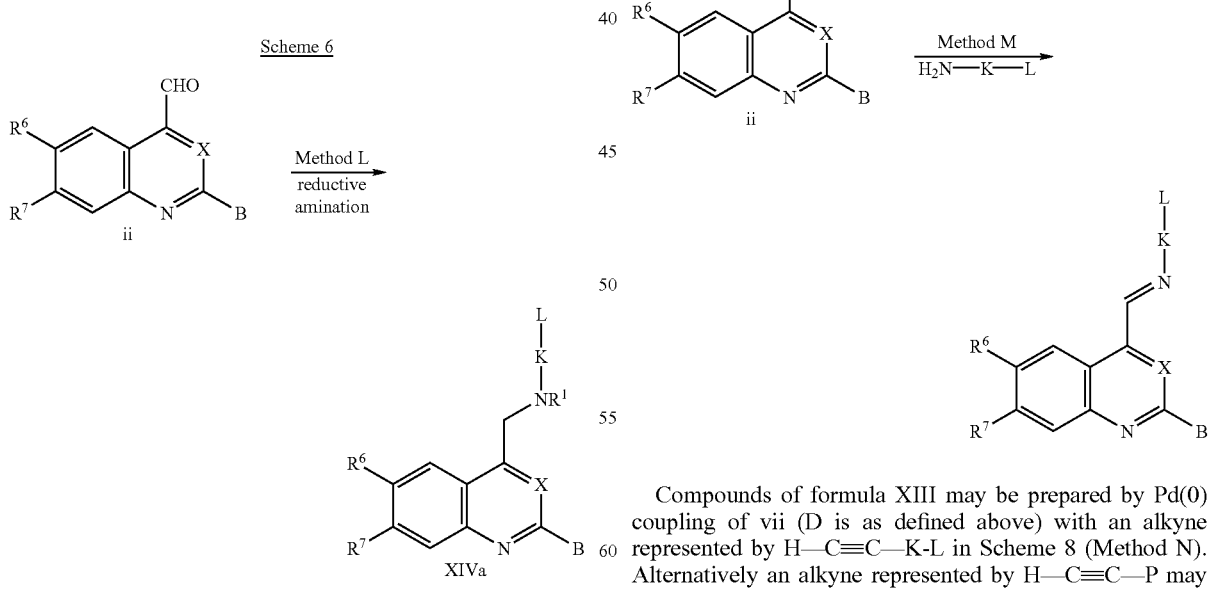

Scheme 7 illustrates the synthesis of compounds of formula XVIIIa, where $R^2$ is H, via condensation of aldehyde ii with an amine, hydrazine or hydroxylamine (Method M).

Compounds of formula XIII may be prepared by Pd(0) coupling of vii (D is as defined above) with an alkyne represented by H—C≡C—K-L in Scheme 8 (Method N). Alternatively an alkyne represented by H—C≡C—P may be utilized to form a compound of formula x via Pd (0) coupling with a suitable coupling partner, such as an aryliodide and the like, as known to those skilled in the art (Methods O and P). Compounds of formula x may also be used as starting materials to prepare compounds of formula XIII by hydrogenation with a suitable catalyst.

Scheme 8

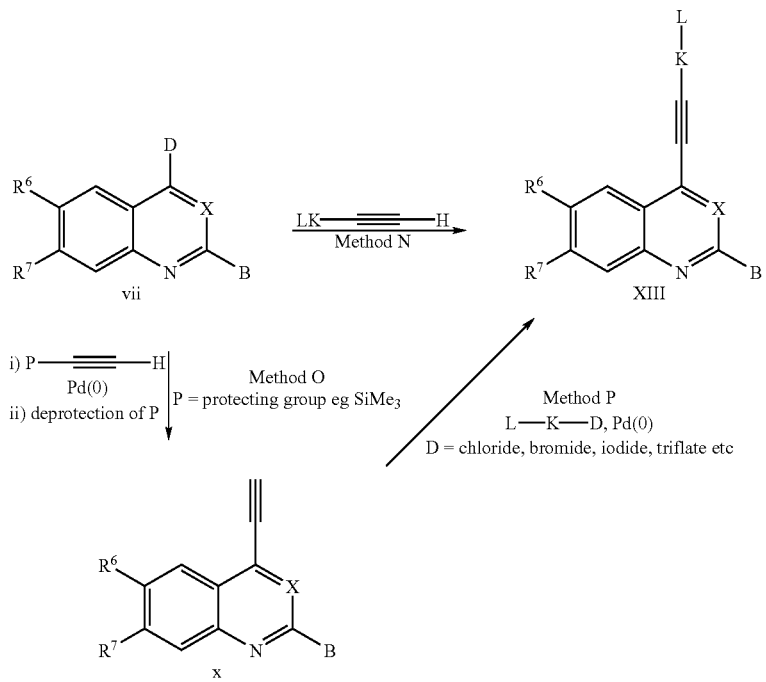

Compounds of the formula XXIa may be prepared from a carboxylic acid derivative xi via the corresponding acid chloride (Method Q); see Scheme 9. Alternatively, compounds of formula XXIa may be prepared by directly coupling from a carboxylic acid derivative xi and a suitable amine, e.g., R¹NH—K-L, in the presence of a coupling reagent, e.g., DCC. Alternative coupling reagents are well known to those skilled in the art.

Scheme 9

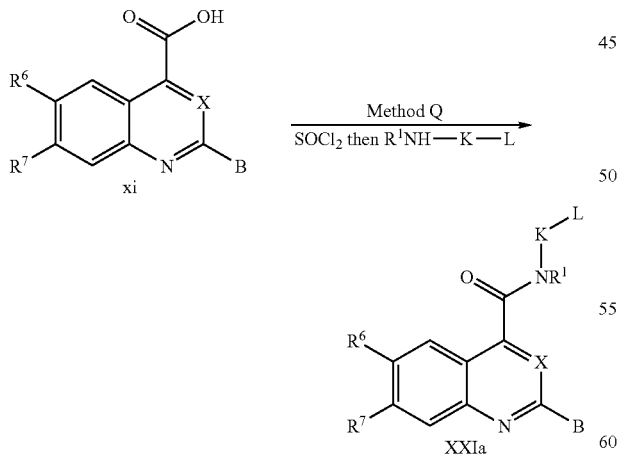

Compounds of formula XXIb may be prepared by reacting an amine derivative xii with a carboxylic acid (represented by L-K—CO₂H in Scheme 10) or an acid chloride (represented by L-K—COCl in Scheme 10 in the presence of a suitable coupling reagent such as DCC (Method S).

Amine xii, where $R^1$ is H, may be prepared from carboxylic acid derivative xi by, for example, reaction with DPPA in the presence of $^t$-BuOH followed by treatment of the resultant carbamate with TFA (Method R).

Scheme 10

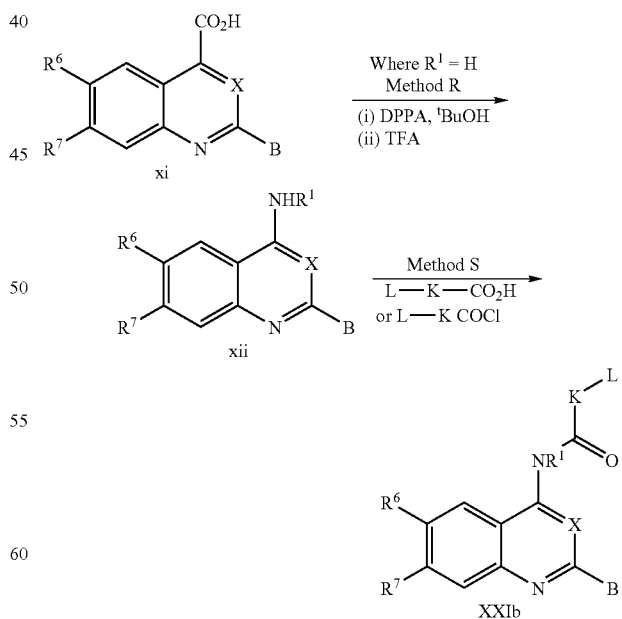

Regarding the molecular structures set forth in Schemes 1–10 above, $R^4$ is hydrogen, $(C_1–C_6)$alkyl, $(C_3–C_6)$cycloalkyl, $(C_4–C_7)$cycloalkyl-alkyl, $(C_2–C_6)$alkenyl or ($C_2$–$C_6$)alkynyl. Moreover, one of skill in the art will readily appreciate that the groups D and A indicate, in a very general sense, a leaving group and a phosphonium or phosphono group, respectively. Each D, and A can be the same or different.

The exemplary methods and the examples described herein are illustrative of the present invention and are not be construed as limiting the scope thereof.

Compositions

In another aspect, the present invention further provides pharmaceutical compositions comprising one or more of the compounds of the invention in admixture with a pharmaceutically acceptable carrier or excipient.

In one embodiment, the invention provides the subject compounds combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc., to form pharmaceutically acceptable compositions.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Still other compositions of the present invention are those that combine two or more of the present compounds in one formulation, or one compound from the present invention with a second antiinflammatory, antiproliferative or antidiabetic agent.

Methods of Use

In yet another aspect, the present invention provides methods of treating IKK-mediated conditions or diseases by administering to a subject having such a disease or condition, a therapeutically effective amount of a compound or composition of the present invention. The "subject" is defined herein to include animals such as mammals, including, but not limited to, primates (e.g., humans), cows, sheep, goats, horses, dogs, cats, rabbits, rats, mice and the like.

Diseases and conditions associated with inflammation, infection and cancer can be treated with the present compounds and compositions. In one group of embodiments, diseases or conditions, including chronic diseases, of humans or other species can be treated with inhibitors of IKK function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; asthma and respiratory allergic diseases such as allergic asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke, ischemic reperfusion injury, traumatic brain injury and closed-head injuries, neurodegenerative diseases, Alzheimer's disease, encephalitis, meningitis, osteoporosis, gout, hepatitis, nephritis, gall bladder disease, sepsis, sarcoidosis, conjunctivitis, otitis, chronic obstructive pulmonary disease, sinusitis and Behcet's syndrome); (5) cell proliferative or neoplastic diseases such as solid tumors, skin cancer, melanoma and lymphoma, and diseases in which angiogenesis and neovascularization play a role; (6) metabolic disorders that are sensitive to inhibition of TNF or IL-1 signaling, such as obesity and complications thereof, type II diabetes, Syndrome X, insulin resistance, hyperglycemia, hyperuricemia, hyperinsulinemia, cachexia, hypercholesterolemia, hyperlipidemia, dyslipidemia, mixed dyslipidemia, hypertriglyceridemia and eating disorders such as anorexia nervosa and bulimia; (7) infectious diseases, e.g., septic shock and bacteremia; and (8) cardiovascular disorders, such as acute heart failure, hypotension, hypertension, angina pectoris, myocardial infarction, cardiomyopathy, congestive heart failure, atherosclerosis, coronary artery disease, restenosis and vascular stenosis.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection or implant), inhalation, nasal, vaginal, rectal, sublingual transdermal or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In the treatment or prevention of conditions mediated by IKK an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory and immunoregulatory disorders and diseases, including asthma and allergic diseases, as well as autoimmune pathologies such as rheumatoid arthritis and atherosclerosis, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin receptor antagonist, such as an interleukin-1 receptor antagonist, an NMDA receptor antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sulindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codiene, hydrocodone, caramiphen, carbetapentane, or dextramethorphan; a diuretic; and a sedating or non-sedating antihistamine. Each of the above agents may be administered, by a route and in an amount commonly used therefor, contemporaneously or sequentially with a compound of the present invention. When a compound of the present invention is used contemporaneously with one or more other drugs, in some cases a pharmaceutical composition containing such other drugs in addition to the compound of the present invention may be preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as methotrexate cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta-adrenergic agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) anti-diabetic agents such as insulin, sulfonylureas, biguamides (metformin), α-glucosidase inhibitors (acarbose) and glitazones (troglitazone, rosiglitazone and pioglitazone); (j) preparations of interferon beta (interferon beta-1.alpha, interferon beta-1.beta.); (k) lubricants or emollients such as petrolatum and lanolin, (1) keratolytic agents, (m) vitamin $D_3$ derivatives (e.g., calcipotriol), (n) anthralin, (o) etretinate and isotretinoin; (p) other compounds such as 5-aminosalicylic acid and prodrugs thereof, antimetabolites such as methotrexate, azathioprine and 6-mercaptopurine, and cytotoxic cancer chemotherapeutic agents; (q) antimicrobial agents such as penicillins (e.g., penicillin G, amoxicillin, nafcillin ampicillin, ticarcillin, negative carbenicillin, cloxacillin, penicillin V), cephalosporins (e.g., cefoxitin, ceforamide polymyxin polymyxin B, colistin), glycopeptides, e.g., vancomycin teicoplanin and ristocetin, biosurfactants (e.g., circulin, EM49, polypeptin, brecistin, cerexin, tridecephin, surfactin, subsporin, mycosubtilisin, bacillomycin) and miscellaneous antibiotics (e.g., capreomycin, bacitracin, gramicidin, gramicidin S, tyrocidine) and (r) agents that directly or indirectly interfere with cytokine signalling, such as soluble TNF receptors, TNF antibodies, soluble IL-1 receptors, IL-1 antibodies, and the like. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases. Electrospray ionization (ESD) mass spectrometry analysis was conducted on a Hewlett-Packard 1100 MSD electrospray mass spectrometer using the HP 1 100 HPLC for sample delivery. Normally the analyte was dissolved in methanol at 0.1 mg/mL and 1 microliter (μL) was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

Example 1

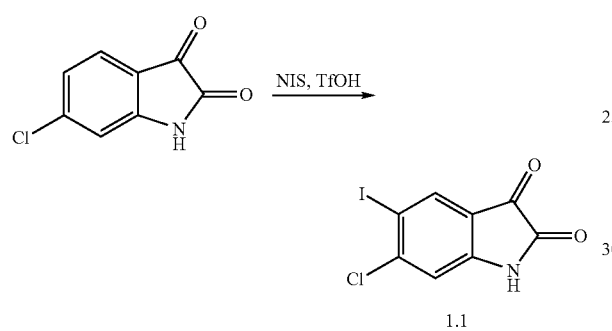

Preparation of 7-Cl, 6-EtCN Aldehyde ii (1a). N-Iodosuccinimide (8.68 g, 38.6 mmol) was added to a stirred mixture of 6-chloro-isatin (6.98 g, 38.6 mmol) and TfOH (120 g) at 0° C. under N$_2$. Ice-bath was removed and stirring at room temperature was continued for 19 h. The mixture was poured to ice-water. The precipitate was collected by filtration, washed with water (until pH~7), and dried to give 6-chloro, 5-iodo-isatine (10.5 g) as a 95% pure ($^1$H NMR, 400 MHz), orange solid: $^1$H NMR (DMSO-d$_6$) 7.10 (s, 1 H), 7.96 (s, 1 H), 11.21 (s, 1 H); ms 305.9 (M−H$^+$).

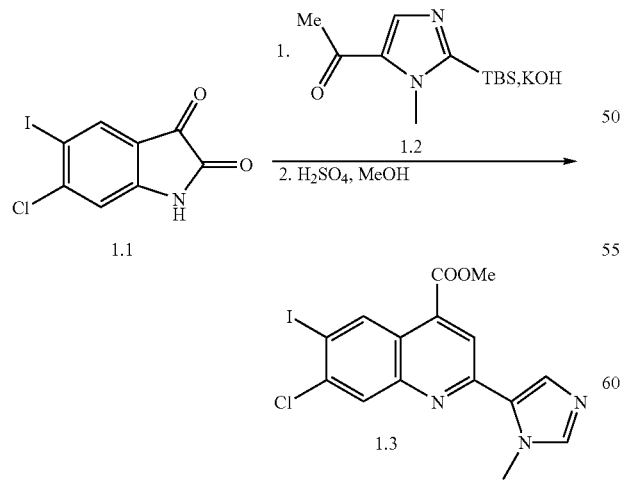

Mixture of 6-chloro, 5-iodo-isatine (26.5 g, 86.3 mmol) and the methylketone 1.2 (22.6 g, 95.0 mmol) (see also, U.S. patent application Ser. No. 10/004,287), in EtOH (150 mL) was treated with KOH (19.4 g, 345 mmol) in water (150 mL). The mixture was heated at 85° C. for 24 h and then cooled to 0° C. 1N HCl (346 mL) was added to the mixture dropwise while a precipitate was formed. The precipitate was collected by filtration, washed with water and dried under vacuum, which gave crude acid (25.2 g): $^1$H NMR (DMSO-d$_6$) δ 4.14 (s, 3 H), 8.10 (s, 1 H), 8.19 (s, 1 H), 8.29 (s, 1 H), 8.30 (s, 1 H), 9.27 (s, 1 H); ms 413.9 (M+H$^+$).

Sulfuric acid (6.0 mL) was added to a stirred suspension of the crude acid (25.2 g) in MeOH (350 mL). The mixture was refluxed for 36 h and then cooled to room temperature. The precipitate was collected by filtration, washed with cold MeOH and dried under vacuum to gave corresponding 7-chloro, 6-iodo methyl ester (17.7 g in two steps), as an off-white solid: $^1$H NMR (DMSO-d$_6$) δ 4.04(s, 3 H), 4.28(s, 3 H), 8.43(s, 1 H), 8.44(s, 1 H), 8.67(s, 1 H), 9.18(s, 1 H), 9.24(s, 1 H); ms 428.0(M+H$^+$).

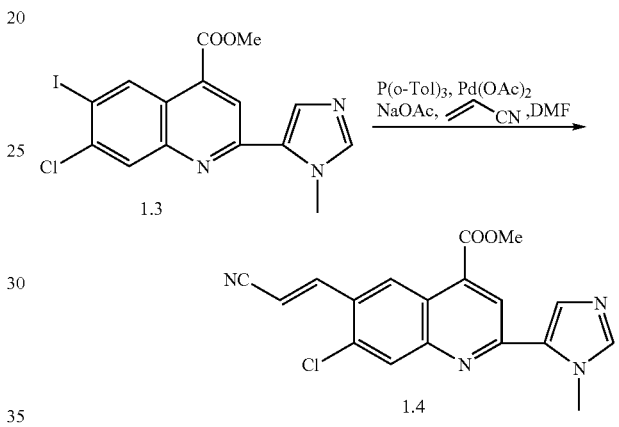

To a mixture of 7-chloro, 6-iodo methyl ester (26.7 g, 62.4 mmol), P(o-tol)$_3$ (3.80 g, 12.5 mmol), NaOAc (11.3 g, 137.3 mmol), and Pd (OAc)$_2$ (1.4 g, 6.2 mmol) in DMF (300 mL), acrylonitrile (20.5 mL, 312 mmol) was added at room temperature under N$_2$. The mixture was heated to 115° C. and stirred for 5 h. The mixture was cooled to room temperature and concentrated. The residue was dissolved in CH$_2$Cl$_2$, washed with saturated aqueous NH$_4$Cl and brine, dried, and concentrated. The concentrated suspension was filtered through a pad of silica gel. The pad was rinsed with 95:5 CH$_2$Cl$_2$-MeOH and the combined filtrates were evaporated. To the residue 1:1 EtOAc-Hex was added. The insoluble material was collected by filtration and washed with 1:1 EtOAc-Hex to gave the desired unsaturated nitrile (13.0 g) as a cis-trans mixture ($^1$H NMR, 400 MHz), solid: $^1$H NMR (DMSO-d$_6$) δ 4.03 (s, 1.2 H), 4.04 (s, 1.8 H), 4.13 (s, 1.8 H) 4.14 (s, 1.2 H), 6.24 (d, J=12 Hz, 0.4 H), 6.63 (d, J=18 Hz, 0.6 H), 7.78 (d, J=12 Hz, 0.4 H), 7.94 (s, 1 H), 7.96 (d, J=18 Hz, 0.6 H), 8.00 (s, 1 H), 8.25 (s, 0.6 H), 8.29 (s, 0,4 H), 8.33 (s, 0.6 H), 8.8.37 (s, 0.4 H), 8.82 (s, 0.6 H), 9.17 (s, 0.4 H); ms 353.1 (M+H$^+$).

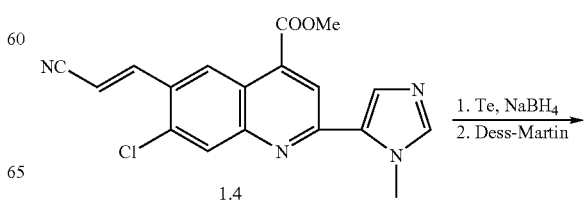

-continued

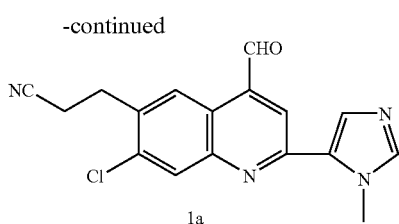

1a

To a suspension of Tellurium (~200 mesh, 4.34 g, 34.0 mmol) in EtOH (150 mL) NaBH$_4$ (3.98 g, 105.4 mmol) was added. The resulting mixture was stirred for 10 min at room temperature. The unsaturated nitrile (6.0 g, 17.0 mmol) in CHCl$_3$ (150 mL) was then added to the stirred reaction mixture in one portion at room temperature. Stirring was continued for 2 h. Second portion of NaBH$_4$ (3.98 g, 105.4 mmol) was added and stirring was continued until reaction was completed (reaction was detected by MS, 10 h in this run). Water (100 mL) was added at 0° C. and the mixture was stirred for 12 h. Black precipitate was filtered out and the precipitate was washed with MeOH. The filtrates were collected and the organic solvents were evaporated. The precipitate in water was collected, washed with water and dried under vacuum.

To the dry precipitate THF (100 mL), CH$_2$Cl$_2$ (100 mL), and Dess-Martin periodinane (10.8 g, 25.5 mmol) were added. The mixture was stirred for 12 h, diluted with CH$_2$Cl$_2$ (100 mL), and poured into saturated aqueous NaHCO$_3$ (100 mL) containing Na$_2$S$_2$O$_3$ (50 g). The mixture was stirred for 30 min. The organic layer was washed with saturated aqueous NaHCO$_3$, water and brine, dried, and evaporated. To the residue 1:1 EtOAc-Hex was added. The insoluble material was collected by filtration and washed with 1:1 EtOAc-Hex to give crude desired yellow solid. The yellow solid was dissolved in hot CH$_2$Cl$_2$ and insoluble precipitate was filtered out (No MeOH was used in this procedure. If methanol is used a mixture of hemiacetal and aldehyde is obtained). The filtrates were evaporated and subjected again to 1:1 EtOAc-Hex. The insoluble yellow solid was collected by filtration to give the desired aldehyde 1 (2.9 g in two steps): $^1$H NMR (DMSO-d$_6$) δ 2.96 (t, 7.2 H), 3.24 (t, 7.2 H), 4.15 (s, 3H), 7.93 (s, 1 H), 7.98 (s, 1 H), 8.23 (s, 1 H), 8.55 (s, 1 H), 8.95 (s, 1 H), 10.47 (s, 1 H); ms 325.1 (M+H$^+$).

Example 2

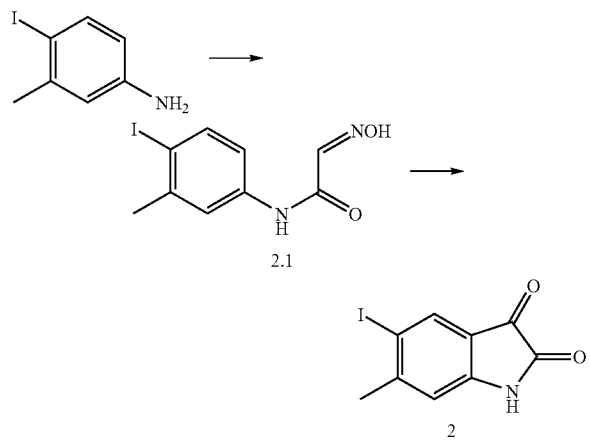

Preparation of 6-Me, 5-I Isatin (2). Chloral hyrdate (17.40 g) is dissolved in water (256 mL) with sodium sulfate (108.75 g). The solution is warmed to 60° C. whereupon hydroxylamine hydrochloride (19.95 g) in water (124 mL) was added. In a separate flask a slurry of 2-iodo 5-amino-toluene (commercially available, Buttpark Ltd, U.K.) in water (139 mL) and CHCl (7.87 mL) was prepared at 80° C. The mixtures were combined and the reaction temperature increased to 95° C. for 20 min. then cooled to room temperature and then at 0° C. for 5 min. The solids were collected by filtration and washed with water (250 mL) and dried under vacuum to afford isonitrosoacetanilide 2.1 as a tan solid. Conc. H$_2$SO$_4$ (75 mL) was warmed to 50° C. and isonitrosoacetanilide 2.1 was added portionwise so that the temperature did not go above 70° C. After the addition the temperature was raised to 80° C. for 10 min. and then the mixture was allowed to cool to ambient temperature and poured onto ice water (10–12× volume). The isatin was filtered and washed with cold water (4×500 mL). The 1:1 isomeric mixture was taken up in 2N NaOH solution (316 mL) and stirred for 2 h then filtered. The filtrate was acidified to approx. pH 6 with acetic acid and refiltered to remove the undesired isatin isomer. The filtrate was acidifed to pH 1 with conc. HCl and filtered and the precipitate (desired isomer 2.7 g) was washed with water and dried by suction. Isatin 2 was converted to the corresponding alde-hyde (3.1) as for isatin 1.1 above.

Example 3

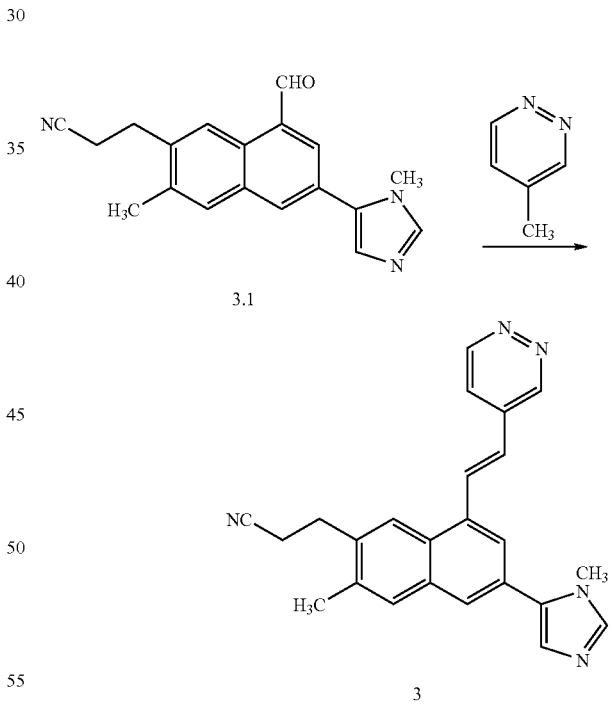

Preparation of Compound 3 by Method A. Aldehyde 3.1 (300 mg, 0.99 mmol.) and 4-methylpyridazine (175 µl, 1.97 mmol.) were combined in a round bottomed flask. The mixture was warmed in a 170° C. oil bath for 30 min. then allowed to, cool to ambient temperature. Flash chromatography (DCM: MeOH 99:1 to 96:4; gradient elution) afforded the product 3 as a yellow solid (120 mg); $^1$H NMR (DMSO-d$_6$) δ 9.72 (s, 1H), 9.33 (d, J=5.5 Hz, 1H), 8.48 (d, J=16 Hz, 1H), 8.34 (s, 1H), 8.22 (s, 1H), 8.00–8.05 (m, 1H), 7.91 (s, 1H), 7.86 (s, 2H), 7.75 (d, J=16 Hz, 1H), 4.16 (s, 3H), 3.17

(t, J=7.5 Hz, 2H), 3.00 (t, J=7.5 Hz, 2H), 2.55 (s, 3H); ESI-MS m/z 381.1 (100, M+H⁺).

Example 4

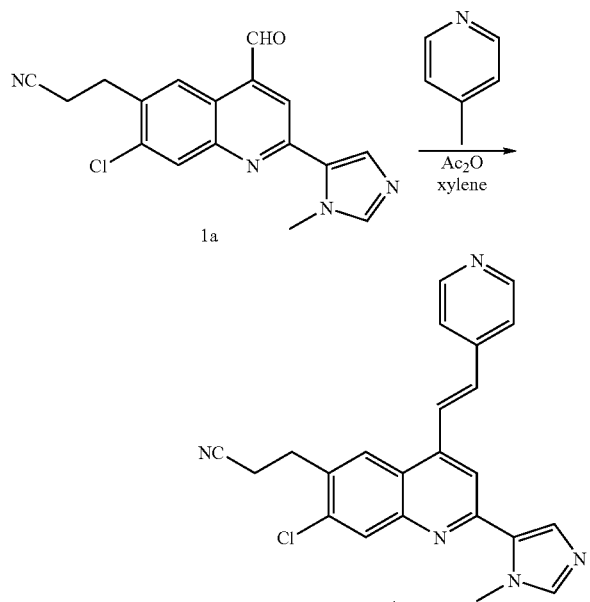

Preparation of Compound 4 by Method A. To a stirred solution of aldehyde 1a (217 mg, 0.67 mmol.) in xylene (3 mL) was added 4-picoline (196 μl, 2.0 mmol.) and acetic anhydride (414 mL, 4.0 mmol.). The mixture was heated at 140° C. for 6 h then cooled to ambient temperature and concentrated in vacuo. Flash chromatography (DCM: MeOH 98:2 to 95:5; gradient elution) afforded the desired trans product 4 (110 mg) as a yellow solid. $^1$H NMR (CDCl$_3$) δ 8.71 (d, J=6 Hz, 2H), 8.14 (s, 1H), 8.06 (s, 1H), 7.89 (d, J=16 Hz, 1H), 7.85 (s, 1H), 7.76 (s, 1H), 7.64 (s, 1H), 7.53 (d, J=6 Hz, 2H), 7.30 (d, J=16 Hz, 1H), 4.21 (s, 3H), 3.31 (t, J=7 Hz, 2H), 2.84 (t, J=7 Hz, 2H); ESI-MS m/z 400.2 (M+H⁺).

Example 5

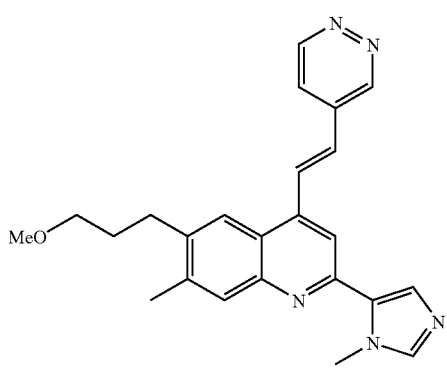

Compound 5 was prepared according to Example 3 using the appropriate aldehyde ii. $^1$H NMR (CDCl$_3$) δ 9.47 (s, 1H), 9.27 (d, J=5.5 Hz, 1H), 8.10 (d, J=16 Hz, 1H), 7.89 (s, 1H), 7.83 (s, 1H), 7.80 (s, 1H) 7.64–7.72 (m, 2H), 7.60 (s, 1H), 7.24 (d, J=16 Hz, 1H), 4.21 (s, 3H), 3.49–3.52 (m, 2H), 3.40 (s, 3H), 2.90–2.96 (m, 2H), 2.56 (s, 3H), 1.95–2.03 (m, 2H).

Example 6

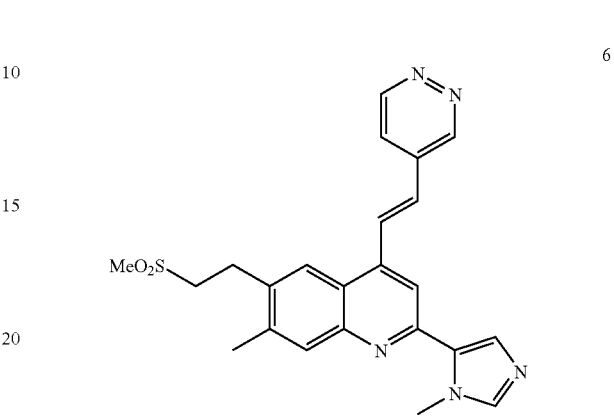

Compound 6 was prepared according to Example 3 using the appropriate aldehyde ii. $^1$H NMR (DMSO-d$_6$) δ 9.72 (s, 1H), 9.33 (d, J=5.5 Hz, 1H), 8.50 (d, J=16 Hz, 1H), 8.34 (s, 1H), 8.22 (s, 1H), 8.02–8.08 (m, 1H), 7.91 (s, 1H), 7.87 (s, 1H), 7.86 (s, 1H), 7.75 (d, J=16 Hz, 1H), 4.16 (s, 3H), 3.49–3.58 (m, 2H), 3.25–3.30 (m, 2H), 3.10 (s, 3H), 2.57 (s, 3H); ESI-MS m/z 434.1 (M+H⁺).

Example 7

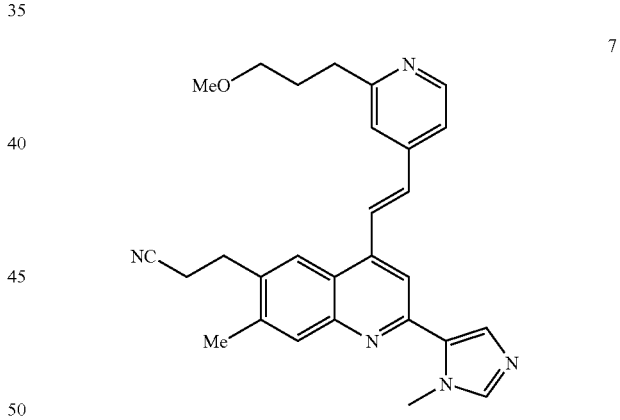

Preparation of Compound 7. 2-(3-methoxypropyl)-4-methylpyridine was prepared in two steps from 2-chloro 4-methylpyridine using standard chemistry. Pd(0) catalyzed coupling of 2-chloro-4-methylpyridine (PdCl$_2$PPh$_3$)$_2$, (0.05 eq.), CuI (0.1 eq.), PPh$_3$, (0.1 eq) Et$_3$N:DMF 1: 1), with methyl propargyl ether (2 eq.) afforded 2-(3-methoxy-prop-1ynyl)-4-methyl-pyridine. Hydrogenation of the alkyne took place using catalytic 10% Pd/C in 1:1 THF:EtOH. Condensation of 2-(3-methoxypropyl)-4-methylpyridine with aldehyde 3.1 was carried out as in Example 3. $^1$H NMR (CDCl$_3$) δ 8.60 (d, 1H, J=5 Hz), 7.92–7.80 (m, 3H), 7.79 (s, 1H), 7.69 (s, 1 H), 7.61 (s, 1 H), 7.38 (s, 1 H), 7.35 (d, 1H, J=5 Hz), 7.34 (d, 1H, J=16 Hz), 4.19 (s, 3H), 3.48 (t, 2 H, J=6.5 Hz), 3.37 (s, 3 H), 3.20 (t, 2H, J=7.5 Hz), 2.94 (t, 2H, J=7.5 Hz), 2.73 (t, 2 H, J=7.5 Hz), 2.56 (s, 3H), 2.09 (q, 2 H, J=6.5 Hz); ESI-MS m/z 452.2 (100, M+1).

Example 8

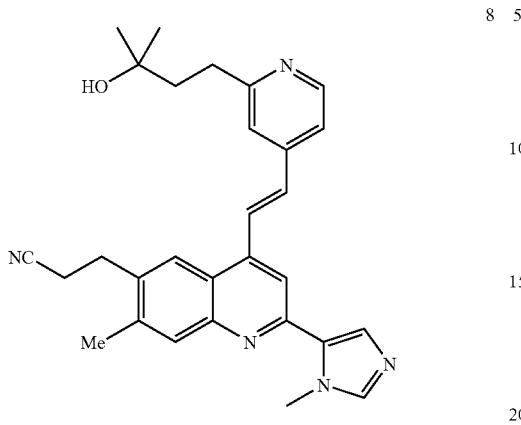

8

Preparation of Compound 8. 4-methyl-4-(4-methyl-pyridin-2-yl)butan-2-ol was prepared in two steps from 2-chloro 4-methylpyridine using standard chemistry. Pd(0) catalyzed coupling of 2-chloro-4-methylpyridine (PdCl$_2$PPh$_3$)$_2$, (0.05 eq.), CuI (0.1 eq.), PPh$_3$, (0.1 eq) Et$_3$N:DMF 1:1), with 2-methyl-3-butyn-2-ol (2 eq.) afforded 2-methyl-4-(4-methyl-pyridin-2-yl)-but-3-yn-2-ol. Hydrogenation of the alkyne took place using catalytic 10% Pd/C in 1:1 THF: EtOH. Condensation of 4-methyl-4-(4-methyl-pyridin-2-yl)butan-2-ol with aldehyde 3.1 was carried out as in Example 3. $^1$H NMR (CDCl$_3$) δ 8.55 (d, 1 H, J=5 Hz), 7.93–7.88 (m, 3 H), 7.78 (s, 1 H), 7.67 (s, 1 H), 7.59 (s, 1 H), 7.41 (s, 1 H), 7.35 (d, 1 H, J=5 Hz), 7.24 (d, 1 H, J=16 Hz), 4.19 (s, 3 H), 3.19 (t, 2 H, J=7.2 Hz), 3.04 (t, 2 H, J=7.5 Hz), 2.74 (t, 2 H, J=7.5 Hz), 1.99 (t, 2 H, J=7.5 Hz), 1.33 (s, 6 H); ESI-MS m/z 468.2 (100, M+1).

Example 9

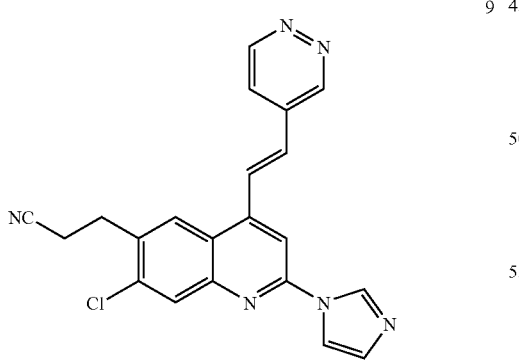

9

Preparation of Compound 9. Compound 9 was prepared according to Example 3 using the appropriate aldehyde ii. $^1$H NMR (CDCl$_3$) δ 9.48 (s, 1H), 9.32 (d, J=5.5 Hz, 1H), 8.55 (s, 1H), 8.19 (s, 1H), 8.12 (s, 1H), 8.08 (d, J=16 Hz, 1H), 7.88 (s, 1H), 7.69–7.65 (m, 2H), 7.33 (d, J=16 Hz, 1H), 7.30 (s, 1H), 3.33 (t, J=7 Hz, 2H), 2.86 (t, J=7 Hz, 2H); ESI-MS m/z 387.1 (M+H$^+$).

Example 10

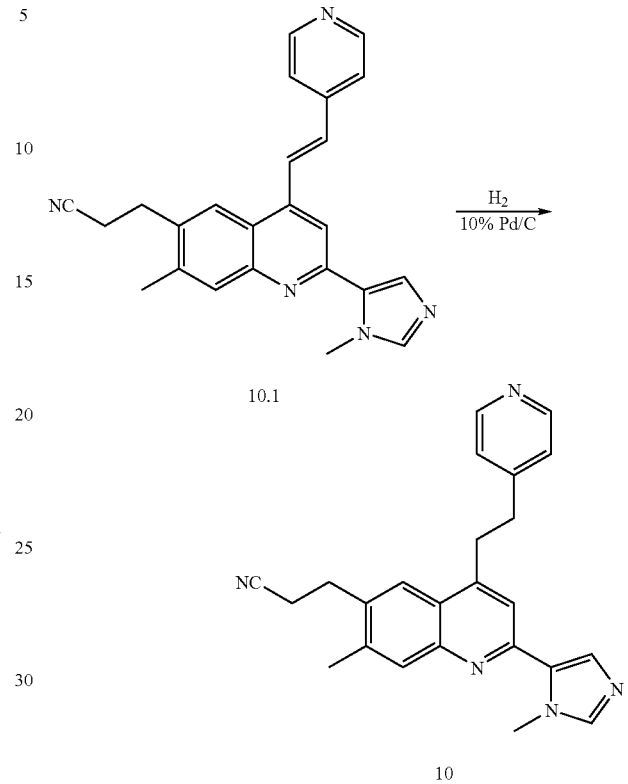

10.1

10

Preparation of Compound 10 by Method B. A mixture of compounds 10.1 (prepared by Method B above) (50 mg, 0.13 mmol.) and 10% Pd/C (20 mg) in THF:MeOH 9:1 (20 mL) was stirred overnight under an atmosphere of hydrogen. The mixture was then filtered through Celite and concentrated in vacuo. Flash chromatography (DCM:MeOH 98:2 to 94:6; gradient elution) afforded the desired product as an off white solid (48 mg); $^1$H NMR (CDCl$_3$) δ 8.55 (d, J=6 Hz, 2H), 7.90 (s, 1H), 7.79 (s, 1H), 7.58 (s, 1H), 7.56 (s, 1H), 7.43 (s, 1H), 7.19 (d, J=6 Hz, 2H), 4.19 (s, 3H), 3.40 (t, J=7 Hz, 2H), 3.10–3.19 (m, 4H), 2.73 (t, J=7 Hz, 2H), 2.55 (s, 3H).

Example 11

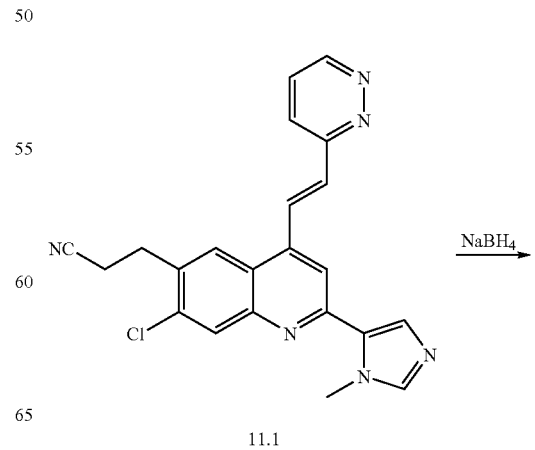

11.1

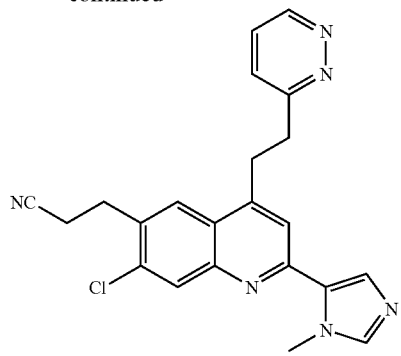

11

Preparation of Compound 11 by Method B. To a stirred solution of pyridazine 11.1 (120 mg, 0.30 mmol.) in dichloromethane-methanol 1:1 (6 mL) was added sodium borohydride (57 mg, 1.5 mmol.) and the mixture stirred at ambient temperature for 4 h. 5 mL of a 15% aqueous NaOH solution was added and the mixture stirred for 1 h then diluted with dichloromethane (20 mL). The organics were collected, dried (Na$_2$SO$_4$), filtered and concentrated in vacuo to afford a yellow solid. Flash chromatography (DCM: MeOH 98:2 to 93:7; gradient elution) afforded the desired product as a white solid (63 mg). $^1$H NMR (CDCl$_3$) δ 9.10 (d, J=5 Hz, 1H), 8.11 (s, 1H), 8.03 (s, 1H), 7.60 (s, 1H), 7.53 (s, 1H), 7.38 (dd, J=5 Hz, J=8.5 Hz, 1H), 7.26–7.31 (m, 2H), 4.18 (s, 3H), 3.67 (t, J=8 Hz, 2H), 3.46 (t, J=8 Hz, 2H), 3.29 (t, J=7 Hz, 2H), 2.82 (t, J=7 Hz, 2H)); ESI-MS m/z 403.3 (M+H$^+$).

Example 12

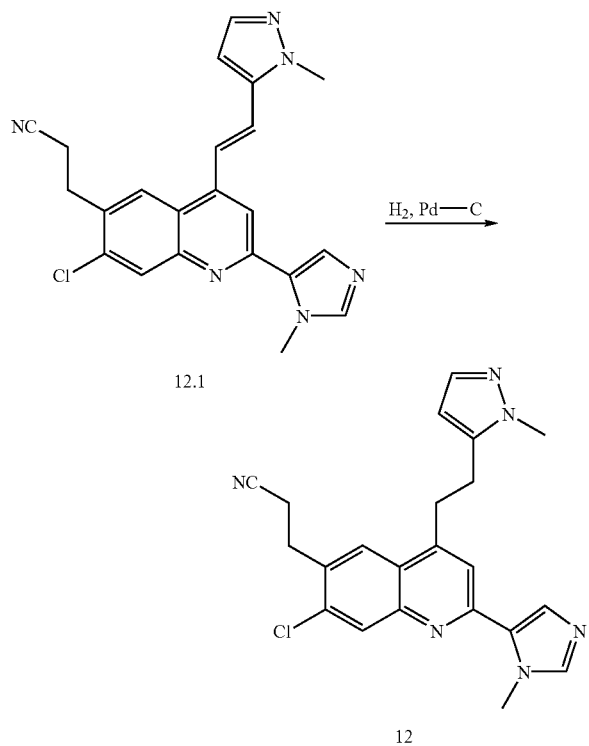

Preparation of Pyrazole 12 by Method B. To a suspension of the pyrazole analog 12.1 (40.0 mg, 0.10 mmol) in McOH (10 mL) 20 mg of 10% Pd/C (Aldrich, 20,569–9) was added and a hydrogen balloon (ca. 1.5 L) was charged on the reaction mixture. Stirring at room temperature in an atmosphere of hydrogen was continued for 24 h. The mixture was filtrated and rinsed with CH$_2$Cl$_2$-MeOH (1:1) (5 mL×3). The filtrates were concentrated. Flash chromatography of the residue over silica gel, using 4:5:1:0.05 hexane-EtOAc-MeOH-NH$_4$OH, gave the desired saturated pyrazole analog 12 (17.0 mg) as a pure solid: $^1$H NMR (CD$_3$OD) δ 2.90 (t, J=6.8 Hz, 2 H), 3.19 (t, J=7.0 Hz, 2 H), 3.35 (t, J=6.8 Hz, 2 H), 3.48 (t, J=7.0 Hz, 2 H), 3.61 (s, 3 H), 4.18 (s, 3 H), 6.17 (s, 1 H), 7.34 (s, 1 H), 7.64 (s, 1 H), 7.65 (s, 1 H), 7.79 (s, 1 H), 8.09 (s, 1 H), 8.11 (s, 1H); ESI-MS m/z 405.1(M+H$^+$).

Example 13

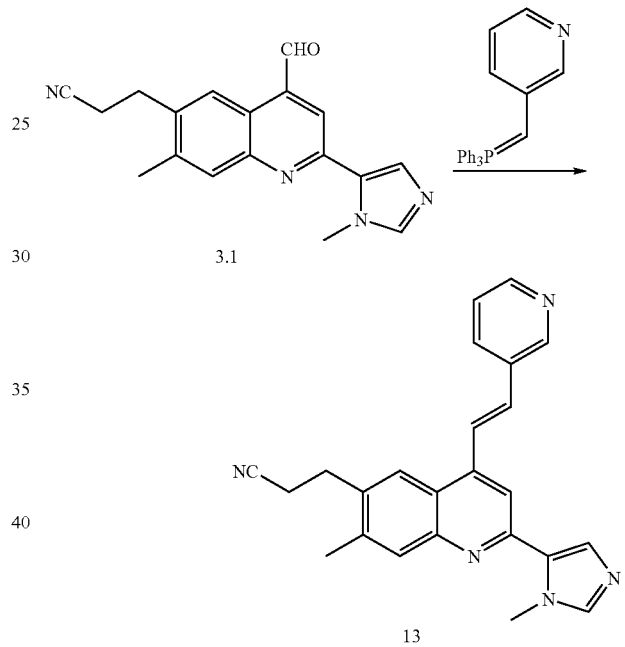

Preparation of Compound 13 by Method C. Sodium hydride (105 mg of a 60% dispersion in oil) under an atmosphere of nitrogen was washed with hexane (2×5 mL). DMSO (4 mL) was added and the mixture stirred at 70° C. for 20 min. then allowed to cool to ambient temperature. DMSO (4 mL) was added followed by triphenyl(pyridin-3-ylmethyl)phosphonium chloride (1.04 g, 2.6 mmol., prepared as G. Bold et al., PCT/EP00/02726) was added portionwise over 2 min. and the black-yellow solution stirred for 10 min. A second flask was prepared with aldehyde 3.1 (400 mg, 0.08 mmol.) in DMSO (2 mL) under nitrogen. The preformed Wittig reagent was added dropwise to the aldehyde solution and the mixture stirred for 90 min. then poured into water (10 mL). The aqueous mixture was extracted with dichloromethane (3×20 mL) and the organics combined, dried (Na$_2$SO$_4$), filtered and concentrated in vacuo. Flash chromatography (DCM:MeOH 99.5:0.5 to 96:4 gave the cis isomer (106 mg) and trans isomer (140 mg). $^1$H NMR (CDCl$_3$) (for trans isomer) 8.88 (d, J=2 Hz, 1H), 8.61 (dd, J=2 Hz, J=5 Hz, 1H), 7.99 (dt, J=8 Hz, J=2 Hz, 1H), 7.94 (s, 1H), 7.90 (s, 1H), 7.79 (d, J=16 Hz, 1H), 7.79 (s 1H), 7.69 (s, 1H), 7.59 (s, 1H), 7.40 (dd, J=15 Hz, J=5 Hz, J=8 Hz, 1H), 7.33 (d, J=16 Hz, 1H), 4.20 (s, 3H), 3.19 (t, J=7.5 Hz, 2H), 2.74 (J=7.5 Hz), 2.56 (s, 3H); ESI-MS m/z 379.1 (M+H$^+$).

Example 14

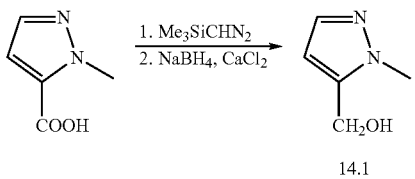

14.1

Preparation of Compound 14 by Method C. (Trimethylsilyl)diazomethane (2.0 M in hexane, 26.8 mL, 53.6 mmol) was added to a stirred solution of 1-methylpyrazole-5-carboxylic acid (4.5 g, 35.7 mmol) in CH$_2$Cl$_2$ (50 mL) at room temperature. Stirring was continued for 1 h and the mixture was concentrated. The residue was dissolved in 1:1 THF-EtOH (250 mL). To the solution, CaCl$_2$ (~30+80 mesh, 3.96 g, 35.7 mmol) and NaBH$_4$ (2.7 g, 71.4 mmol) was added at 0° C. Cold bath was removed and stirring was continued for 1.5 h. The mixture was quenched with saturated aqueous NH$_4$Cl (2 mL), filtered through a pad (2.5×3 cm) of flash chromatography silica gel, and the pad was rinsed with CH$_2$Cl$_2$ (ca. 100 mL). The combined filtrates were concentrated and dried under vacuum. The dried crude alcohol (3.0 g) was directly used for next step.

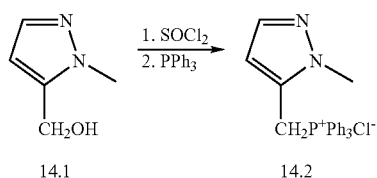

14.1    14.2

SOCl$_2$ (2.6 mL, 35.7 mmol) was added dropwise to a solution of the crude alcohol 14.1 (3.0 g, 26.8 mmol) in CH$_2$Cl$_2$ at 0° C. Cold bath was removed and stirring was continued for 12 h. The reaction mixture was concentrated. To the residue EtOAc was added and the insoluble residue was well distributed by ultrasonication. The residue was collected by filtration. Washing with EtOAc gave crude desired chloride 14.2 (1.12 g). A mixture of crude chloride (1.12 g, 8.48 mmol) and PPh$_3$ (2.22 g, 8.48 mmol) in Toluene (30 mL) was refluxed for 2.5 h. The mixture solution was allowed to cool to room temperature and concentrated. To the residue hexane was added and the insoluble residue was well distributed by ultrasonication. The residue was collected by filtration. Washing with hexane gave crude desired phosphonium salt (810 mg); ESI-MS m/z 357.2 (M$^+$–Cl).

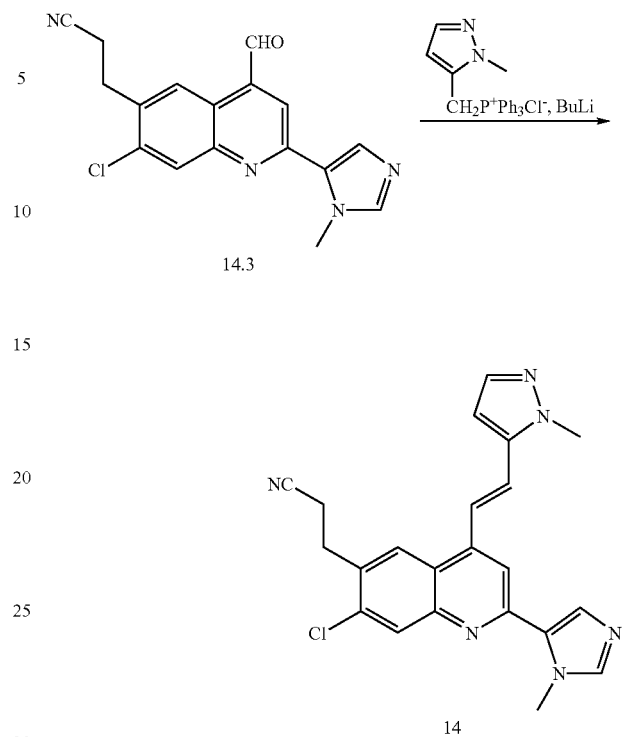

n-BuLi (2.5 M in hexane, 0.91 mL, 2.27 mmol) was added dropwise to a stirred and cooled (0° C.) solution of the phosphonium salt 14.2 (810 mg, 2.06 mmol) in THF (20 mL), and stirring at 0° C. was continued for 20 min. A suspension of 7-chloro, 6-cyanoethyl 4-quinolinecarbaldehyde 14.3 (0.70 g, 2.06 mmol) in THF (10 mL) was added in one portion to the above phosphorus ylide solution. The mixture was stirred at room temperature for 3 h. The reaction was quenched with saturated aqueous NH$_4$Cl (10 mL), and the mixture was extracted with CH$_2$Cl$_2$ (3×20 mL). The combined organic extracts were washed with water (10 mL), brine (10 mL), dried and evaporated. Flash chromatography of the residue over silica gel, using 5:95 MeOH—CH$_2$Cl$_2$, and re-crystallization in MeOH, gave the desired trans unsaturated pyrazole analog (230 mg) as a pure solid: $^1$H NMR (CDCl$_3$) δ 2.82 (t, J=7.0 Hz, 2 H), 3.29 (t, J=7.0 Hz, 2 H), 4.02 (s, 3 H), 4.21 (s, 3 H), 6.70 (s, 1 H), 7.22 (d, J=16 Hz, 1 H), 7.53 (s, 1 H), 7.60 (d, J=16 Hz, 1 H), 7.67 (s, 1 H), 7.75 (s, 1 H), 7.80 (s, 1 H), 8.03 (s, 1 H), 8.13 (s, 1 H); ESI-MS m/z 403.0 (M+H$^+$).

Example 15

Preparation of Compound 15 by Methods H and I. Chloride 15.2 where R$^6$ is CH═CHCN or CH$_2$CH$_2$CN and R$^7$=Me and B=1-methylimidazol-5-yl may be prepared in three steps from aniline 15.4, as indicated below. Aniline 15.1 is treated with and POCl$_3$ to afford dichloride 15.2. Conversion to the vinylcyano compound 15.3 by Pd(0) coupling with acrylonitrile is followed by conversion to 15.4 by coupling with 1-methyl-5-tributylstannyl imidazole. Nucleophilic aromatic substitution of the 4-chloro with either an amine or alcohol may be followed by reduction of R$^6$ is CH═CHCN to R$^6$ is CH$_2$CH$_2$CN.

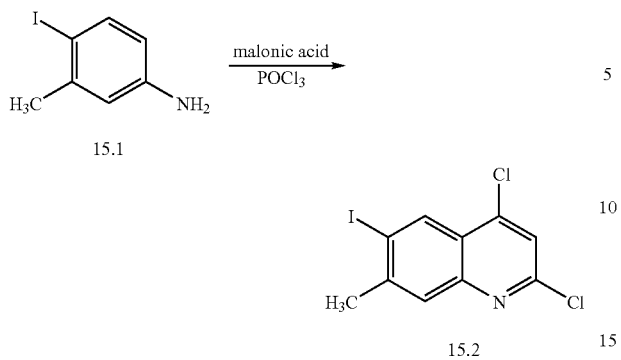

A mixture of malonic acid (163.4 g, 1.575 mol) and 4-iodo-3-methylaniline (349.6 g, 1.500 mol) in phosphorous oxychloride (980 mL, 10.50 mol) was warmed to a gentle reflux temperature in a 105° C. oil bath for 3 h. The viscous solution was allowed to cool to room temperature and slowly poured onto approximately 12 L of loosely packed crushed ice and allowed to stir for 12 h. Methylene chloride (4 L) and water (1 L) were added to the mixture and the aqueous phase of the resulting solution was extracted with DCM (3×1 L), and the organics combined, dried (MgSO$_4$), filtered, and concentrated in vacuo. Absorbing the material onto silica gel followed by flash chromatography (hexane: diethyl ether 99:1 to 97:3; gradient elution) afforded the desired product as a white solid. Additional chromatography was applied to impure fractions containing the desired product (hexane:diethyl ether 99:1 to 97:3; gradient elution) to provide the desired product (58.0 g total) as a white solid; $^1$H NMR (CDCl$_3$) δ 8.78 (s, 1H), 7.79 (s, 1H), 7.39 (s, 1H), 2.60 (s, 3H); ESI-MS m/z 336.9 (M+H$^+$).

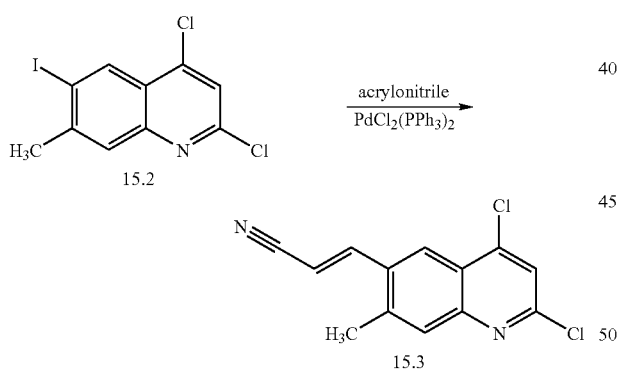

A mixture of compounds 15.2 (51.3 g, 152 mmol), PdCl$_2$(PPh$_3$)$_2$ (5.33 g, 3.00 mmol), Hunig's base (32.0 mL, 182 mmol), and acrylonitrile (53.0 mL, 761 mmol) in DMF (380 mL) was heated in a 120° C. oil bath for 2 h. The solution was allowed to cool to room temperature and was poured into water (4.5 L). After stirring for 2 h, the mixture was filtered and the resulting red solid was absorbed onto silica gel and flash chromatography (hexane:DCM 40:60 to 0:100; gradient elution) afforded the desired product (5:2 trans:cis isomers) as an off-white solid (32.0 g). $^1$H NMR (CDCl$_3$) δ (for trans isomer) 8.26 (s, 1H), 7.88 (s, 1H), 7.78 (d, J=16.5 Hz, 1H), 7.51 (s, 1H), 6.05 (d, J=16.5 Hz, 1H), 2.61 (s, 3H); (for cis isomer) 8.81 (s, 1H), 7.92 (s, 1H), 7.53 (s, 1H), 7.51 (d, J=11.8 Hz, 1H), 5.76 (d, J=11.8 Hz, 1H), 2.56 (s, 3H); ESI-MS m/z 263.0 (M+H$^+$).

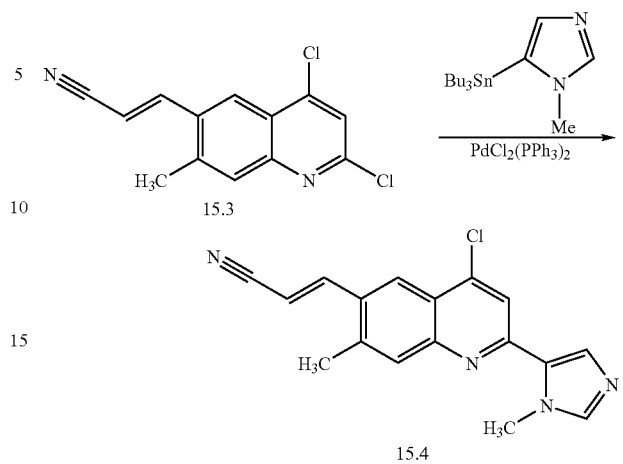

A mixture of compound 15.3 (10.78 g, 41.0 mmol), Pd(PPh$_3$)$_4$ (3.31 g, 2.87 mmol), CuI (0.781 g, 4.10 mmol), and 1-methyl-5-tributylstannylimidazole (15.9 g, 43.0 mmol, Gaare et al., Acta Chem. Scand. 1993, 47 (1), 57–62) in DMF (400 mL) was heated in a 60° C. oil bath for 3 h. The resulting solution was allowed to cool to room temperature, poured into water (1.0 L), and allowed to stir for 1 h. The mixture was then filtered through celite and the resulting cake was dissolved in 10% MeOH/DCM (1 L) concentrated in vacuo. Flash chromatography (DCM:MeOH 5:95 to 60:40; gradient elution) followed by washing the resulting product with hexane (3×300 mL) afforded the desired product as an off-white solid (10.1 g); $^1$H NMR (DMSO-d$_6$) δ 8.35 (s, 1H), 8.18 (s, 1H), 8.00 (d, J=16.6 Hz, 1H), 7.97 (br s, 1H), 7.92 (s, 1H), 7.90 (br s, 1H), 6.65 (d, J=16.5 Hz, 1H), 4.13 (s, 3H), 2.60 (s, 3H); ESI-MS m/z 309.1 (M+H$^+$).

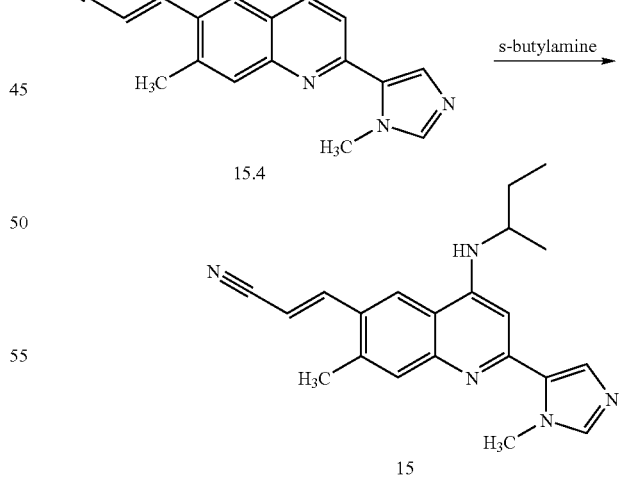

A mixture of compound 15.4 (154 mg, 0.50 mmol) and sec-butylamine (5 mL) in a sealed tube was heated in a 120° C. oil bath for 24 h. The mixture was then concentrated in vacuo. Flash chromatography (DCM:MeOH 98:2 to 90:10; gradient elution) afforded an impure sample of the desired product. Additional flash chromatography (EtOAc:MeOH 98:2 to 90:10; gradient elution) afforded the desired product as a yellow solid (25 mg); $^1$H NMR (CD$_3$OD) δ 8.44 (s, 1H), 7.98 (s, 1H), 7.78 (d, J=16.5 Hz, 1H), 7.73 (s, 1H), 7.58 (s, 1H), 7.43 (s, 1H), 6.31 (d, J=16.5 Hz, 1H), 3.99 (s, 3H), 3.65 (m, 1H), 2.48 (s, 3H), 2.02 (m, 2H), 1.29 (d, J=6.6 Hz, 3H), 1.03 (t, J=6.6 Hz, 3H); ESI-MS m/z 346.2 (M+H$^+$).

Example 16

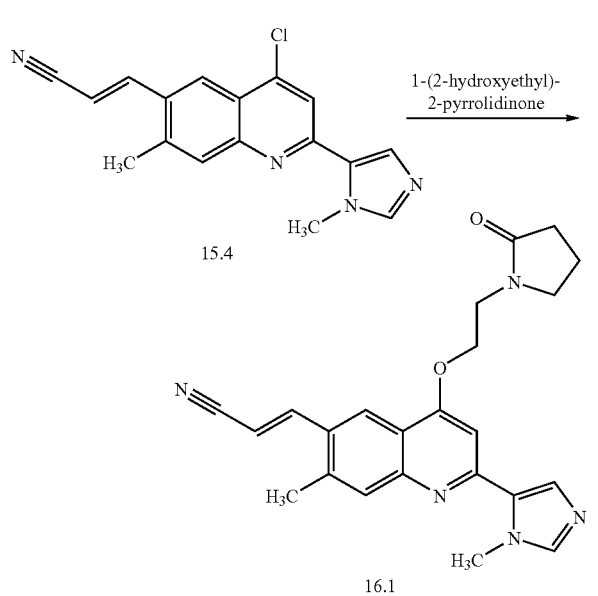

15.4

1-(2-hydroxyethyl)-2-pyrrolidinone 16.1

A mixture of compound 15.4 (154 mg, 0.50 mmol), 1-(2-hydroxyethyl)-2-pyrrolidinone (0.57 mL, 5.0 mmol) and sodium hydride (100 mg of a 60% dispersion in oil, 2.5 mmol) in chlorobenzene (3.0 mL) was heated in a 70° C. oil bath for 2 h. After allowing the solution to cool to room temperature, saturated aqueous NaHCO$_3$ (10 mL) and DCM (10 mL) were added. The aqueous solution was extracted with DCM (5 mL) and the organics combined, dried (Na$_2$SO$_4$), filtered and concentrated in vacuo. Flash chromatography (DCM:MeOH 98:2 to 90:10; gradient elution) afforded the desired product as an off-white solid (80 mg); $^1$H NMR (DMSO-d$_6$) δ 8.34 (s, 1H), 7.96 (d, J=16.6 Hz, 1H), 7.87 (s, 1H), 7.79 (s, 1H), 7.76 (s, 1H), 7.34 (s, 1H), 6.43 (d, J=16.5 Hz, 1H), 4.70 (t, J=5.5 Hz, 2H), 4.44 (t, J=5.4 Hz, 2H), 4.11 (s, 3H), 3.75 (t, J=8.2 Hz, 2H), 2.56 (s, 3H), 2.19 (t, J=8.3 Hz, 2H), 1.92 (m, 2H); ESI-MS m/z 402.2 (M+H$^+$).

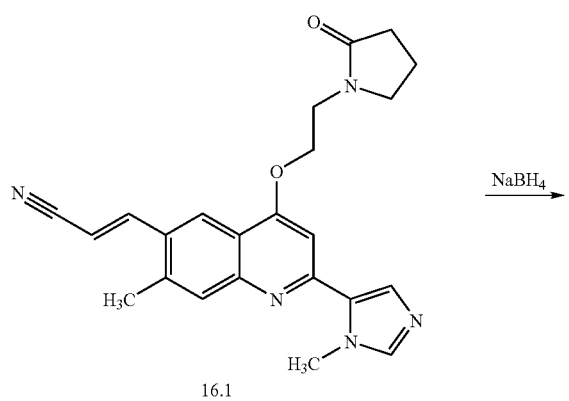

16.1

NaBH$_4$

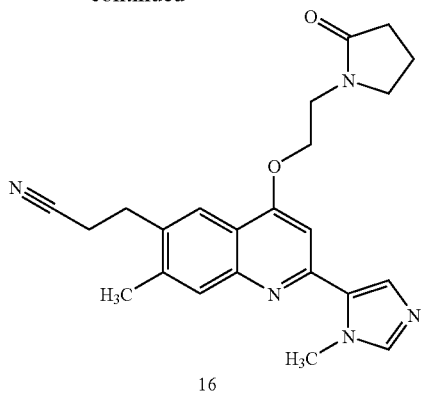

16

A mixture of compound 16.1 (42 mg, 0.10 mmol) and NaBH$_4$ (0.40 g, 10.6 mmol) in MeOH:DCE 1:1 (5 mL) was heated in a 60° C. oil bath for 3 days. The mixture was then allowed to cool to room temperature and saturated aqueous NaHCO$_3$ (10 mL) and EtOAc (10 mL) was added. The aqueous solution was extracted with EtOAc (10 mL) and the organics combined, dried (Na$_2$SO$_4$), filtered and concentrated in vacuo. Flash chromatography (DCM:MeOH 95:5 to 90:10; gradient elution) afforded the desired product as an off-white solid (12 mg); $^1$H NMR (CD$_3$OD) δ 9.03 (s, 1H), 8.25 (s, 1H), 8.10 (s, 1H), 7.89 (s, 1H), 7.34 (s, 1H), 4.50 (t, J=5.1 Hz, 2H), 4.35 (s, 3H), 3.90 (t, J=5.1 Hz, 2H), 3.70 (t, J=7.0 Hz, 2H), 3.19 (t, J=7.0 Hz, 2H), 2.91 (t, J=7.0 Hz, 2H), 2.57 (s, 3H), 2.43 (t, J=8.3 Hz, 2H), 2.07 (quin, J=7.8, 2H); ESI-MS m/z 404.2 (M+H$^+$).

Example 17

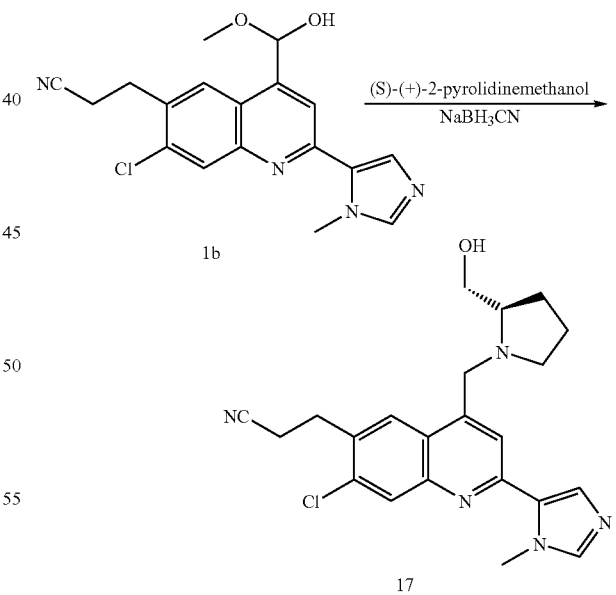

1b (S)-(+)-2-pyrrolidinemethanol
NaBH$_3$CN

17

Preparation of Compound 17 by Method L. To a stirred solution of the hemiacetal 1b (80 mg, 0.225 mmol) (NB: the corresponding aldehyde (1a) may be isolated as a hemiacetal (1b) or mixture of hemiacetal and aldehyde if an alcohol such as methanol is utilized in purification) in 20:1 EtOH: HOAc (25 mL) was added (S)-(+)-2-pyrrolidinemethanol (33 μl, 0.334 mmol), and sodiumcyanoborohydride (100 mg, 1.5 mmol). The resulting solution was allowed to stir overnight at room temperature. The solvent was removed under reduced pressure. Flash chromatography of the residue (DCM:MeOH 98:2 to 90:10; gradient elution) gave the desired product as a yellow solid (17.8 mg); $^1$H NMR (CD$_3$OD) δ 8.40 (s, 1H), 8.09 (s, 1H), 7.91. (s, 1H), 7.82 (s, 1H), 7.75 (s, 1H), 4.80 (d, J=14 Hz, 1H), 4.19 (s, 3H), 4.02 (d, J=14 Hz, 1H), 3.76 (m, 2H), 3.28 (d, 3H), 3.08 (m, 1H), 2.95 (m, 3H), 2.62 (q, 1H), 2.09 (m, 1H), 1.82 (m, 3H).

Example 18

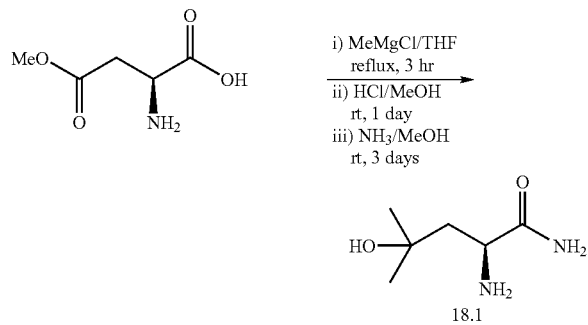

Preparation of Compound 18 by Method L. L-Asp(OMe)-OH (1 g, 6.8 mmol) was suspended in 78 mL of THF at 0° C. under a nitrogen atmosphere. 7 mL of 3 M methyl magnesium chloride (21 mmol) was then added dropwise. The reaction mixture was heated at reflux for 3 h and then cooled to 0° C. 20 mL of 1 N ethereal HCl and 5 mL of methanol were added and the mixture was stirred and allowed to warm to room temperature. The mixture was evaporated in vacuo. The residue was dissolved in 6 mL of methanol, cooled to 5° C. (ice bath), and treated with a solution of 10 g of anhydrous hydrogen chloride gas in 5 mL of methanol. The mixture was stirred at room temperature overnight and evaporated in vacuo. The residue was dissolved in 15 mL of methanol, cooled to −78° C., and treated with a solution of 11 g of ammonia in 5 mL of methanol. The mixture was stirred and allowed to warm to room temperature. Stirring was continued at room temperature for 3 days, and the mixture was evaporated in vacuo. The crude material was purified by flash chromatography on a silica gel column using chloroform:methanol (2:1) as eluent. The major fractions were combined and concentrated to give the desired product (0.54 g) as a white solid; $^1$H NMR (400 MHz, D)MSO) δ 4.37 (d, 1H), J=4.5 Hz), 3.89 (dd, 1H), 1.75 (dd, 1H), 1.24 (s, 1H), 0.97 (s, 1H); ESI m/z (M+Na$^+$).

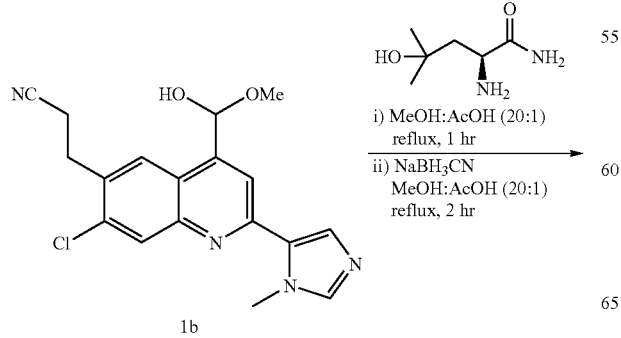

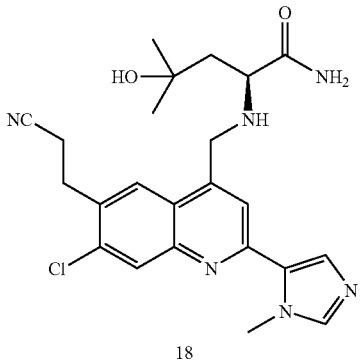

A solution of aldehyde 1a (0.1 g, 0.28 mmol) and (S)-2-amino-4-hydroxy-4-methylpentanoic acid amide (18.1) (0.48 g, 3.31 mmol) in 8 mL of methanol-acetic acid (20:1) was heated at reflux. After 1 h a solution of sodium cyanoborohydride (2.0 equiv) in 6 mL of methanol:acetic acid (20:1) was added dropwise. The reaction mixture was heated at reflux for 3 h and then cooled to room temperature. 10 mL of H$_2$O was added and then stirred for 10 min. The mixture was extracted with CH$_2$Cl$_2$ (4×30 mL), dried (Na$_2$SO$_4$), filtered, and the solvent evaporated. The crude material was purified by flash chromatography on a silica gel column using 50% methylene chloride:methanol:ammonium hydroxide (89:9:1) in methylene chloride as eluent. The major fractions were combined and concentrated to give the desired product (12 mg) as a pale yellow solid; $^1$H NMR (400 MHz, DMSO) 8.19 s, 1H), 8.11 (s, 1H), 7.95 (s, 1H), 7.87 (s, 1H), 7.82 (d, J=1 Hz, 1H), 7.48 (s, 1H), 7.15 (s, 1H), 4.20–4.03 (m, 5H), 3.23 (m, 2H), 2.98 (m, 2H), 1.12 (s, 6H); ESI-MS m/z 455.3 (M+H$^+$).

Example 19

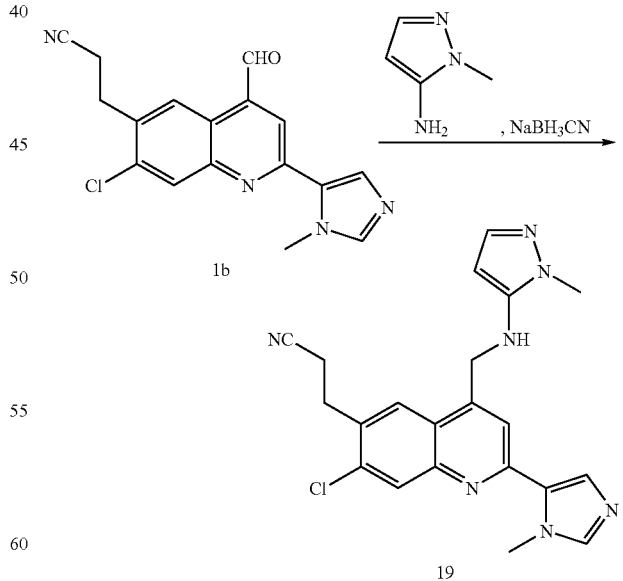

Preparation of Compound 19 by Method L. To a mixture of 7-chloro, 6-cyanoethyl 4-quinolinecarbaldehyde (1a) (100 mg, 0.28 mmol), 1-methyl-5-amino pyrazole (162 mg, 1.67 mmol) and NaBH$_3$CN (17.6 mg, 0.28 mmol) in MeOH (5 mL) HOAc (3 drops) was added. The mixture was refluxed for 30 min. The solution was allowed to cool to room temperature and concentrated. Flash chromatography of the residue over silica gel, using 4:5:1:0.1 hexane-EtOAc-MeOH—NH$_4$OH, gave the desired amino pyrazole analog (19.5 mg) as a pure solid. $^1$H NMR (CDCl$_3$) δ 2.79 (t, J=7.0 Hz, 2 H), 3.25 (t, J=7.0 Hz, 2 H), 3.30 (br s, 1 H), 3.70 (s, 3 H), 4.11 (s, 2 H), 4.17 (s, 3 H), 7.15 (s, 1 H), 7.27 (s, 1 H), 7.49 (s, 1 H), 7.59 (s, 1 H), 7.60 (s, 1 H), 7.98 (s, 1 H), 8.10 (s, 1H); ESI-MS m/z 406.1 (M+H$^+$).

Example 20

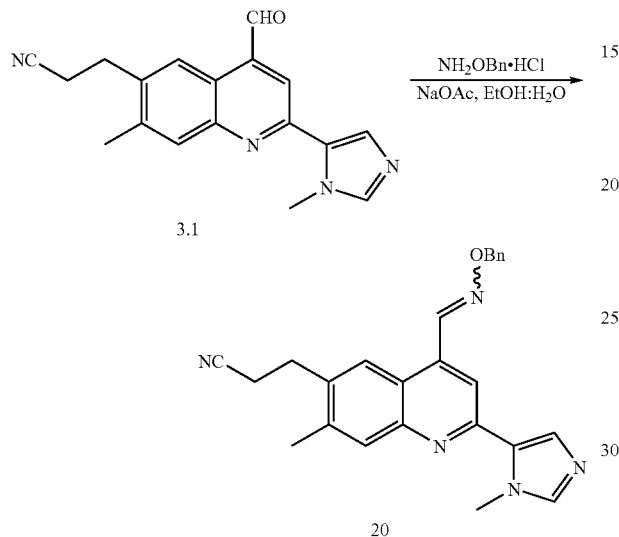

Preparation of Compound 20 by Method M. To a stirred solution of aldehyde 3.1 in ethanol (4 mL) and H$_2$O (1 mL) was added sodium acetate and o-benzylhydroxyamine hydrochloride. The mixture was heated at 50° C. for 2 h then concentrated in vacuo. Flash chromatography of the residue (DCM:MeOH:NH$_4$OH 100:1.5:1) gave the desired product (54 mg) as a yellow solid and as a 1:3 mixture of cis and trans isomers. $^1$H NMR (CDCl$_3$) δ 8.63 (s, 1H), 8.20 (s, 1H), 7.26–7.99 (m, 8H), 5.35 (3H, trans isomer), 5.24 (3H, cis isomer), 4.20 (s, 3H trans isomer), 4.19 (s, 3H cis isomer), 3.06–3.10 (m, 2H), 2.58–2.52 (m, 5H); ESI-MS m/z 410.1 (M+H$^+$).

Example 21

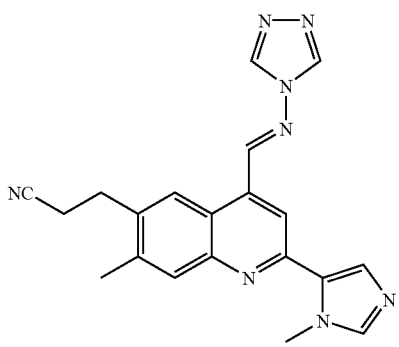

Preparation of Compound 21 by Method M. Compound 21 was prepared according to Example 20 using aldehyde 3.1. $^1$H (DMSO, d-6) δ 9.69 (s, 1 H), 9.38 (s, 1 H), 8.61 (s, 1 H), 8.24 (s, 1 H), 7.91 (s, 1 H), 7.87 (s, 1 H), 7.77 (s, 1 H), 4.18 (s, 3H), 3.17 (t, 2H, J=7 Hz), 3.00 (t, 2 H, J=7 Hz), 2.57 (s, 3H); ESI-MS m/z 371.2 (M+H$^+$)

Example 22

Preparation of Compound 22 as 4.1 by Method M. Compound 22 was prepared according to Example 20 using aldehyde 3.1. $^1$H (DMSO, d-6) δ 8.48 (s, 1 H), 8.23 (s, 1 H), 7.99 (s, 1 H), 7.82 (s, 2 H), 7.63 (s, 1 H), 4.16 (s, 3 H), 3.80–3.90 (m, 2 H), 3.38 (m, 2 H), 3.10 (t, 2 H, J=7 Hz), 2.94 (t, 2 H, J=7 Hz), 2.50 (s, 3 H); ESI-MS m/z 389.2 (M+H$^+$)

Example 23

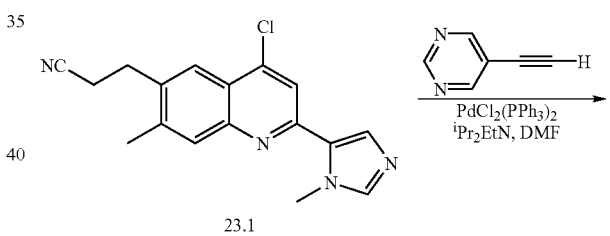

Preparation of Compound 23 by Method N. To a stirred solution of chloroquinoline 23.1 (150 mg, 0. 48 mmol.) and PdCl$_2$(PPh$_3$)$_2$ (17 mg) in DMF (5 mL) and $^i$Pr$_2$EtN (5 mL) was added pyrimidine 23.2 (151 mg, 1.4 mmol. (Eckert et al., *Monatschchem.*, 129, 1035 (1988)). The mixture was heated at 100° C. for 2 h then at 130° C. for 3 h then cooled and concentrated in vacuo and the residue taken up in dichloromethane-water. The organics were collected, dried ($Na_2SO_4$), filtered and concentrated. Flash chromatography (DCM to DCM: MeOH 94:6; gradient elution) afforded the product as a cis/trans mixture; ESI-MS m/z 377.3 (M+H$^+$).

Example 24

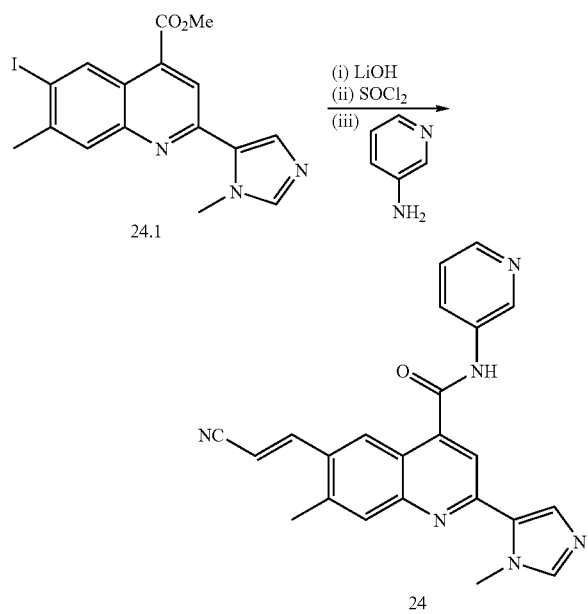

Preparation of Compound 24 by Method Q. A stirred solution of iodoester 24.1 (1 g, 2.5 mmol.) in 10 mL 33% KOH was heated to 90° C. for 18 h. The mixture was cooled to ambient temperature and acidified to pH 4 with glacial acetic acid. The solution was filtered to yield 500 mg of the carboxylic acid as a brown solid. A stirred solution of the acid (500 mg, 1.27 mmol.) in 5 mL thionyl chloride (69 mmol.) was heated to reflux for 18 h. The mixture cooled to ambient temperature and concentrated in vacuo to yield the acid chloride as a yellow solid. To a stirred solution of acid chloride (200 mg, 0.49 mmol.) in 10 mL dichloromethane was added DIPEA (49 mL, 0.49 mmol) followed by 3-amino pyridine (46 mg, 0.49 mmol). The mixture stirred 2 h. at ambient temperature, and was then concentrated in vacuo to yield 150 mg of the amide as a yellow solid. To a stirred solution of iodoamide (150 mg, 0.32 mmol.) in 10 mL dry N,N-dimethylformamide under an atmosphere of nitrogen was added acrylonitrile (106.mL, 1.6.mmol), $Pd(PPh_3)_2Cl_2$ (11 mg, 0.016.mmol.) and DIPEA (50 mL, 0.384 mmol.). The mixture was heated to 140° C. for 18 h. The mixture was cooled to RT and concentrated in vacuo to yield a dark oil which was purified over 25 mL silica with a solvent gradient of zero to five percent methanol in dichloromethane, yielding 22 mg of the expected final product as a yellow solid. $^1H$ (DMSO, d-6) δ 8.67 (s, 1H), 8.52 (d, 1H, J=7 Hz), 8.49 (s, 1H), 8.38 (d, 1 H, J=5 Hz), 7.91 (s, 1 H), 7.89 (s, 1 H), 7.75 (d, 1 H, J=16 Hz), 7.73 (s, 1 H), 7.60 (s, 1H), 7.35–7.45 (m,1 H), 6.05 (d, 1H, J=16 Hz), 4.11 (s, 3 H), 2.59 (s, 1 H).

Example 25

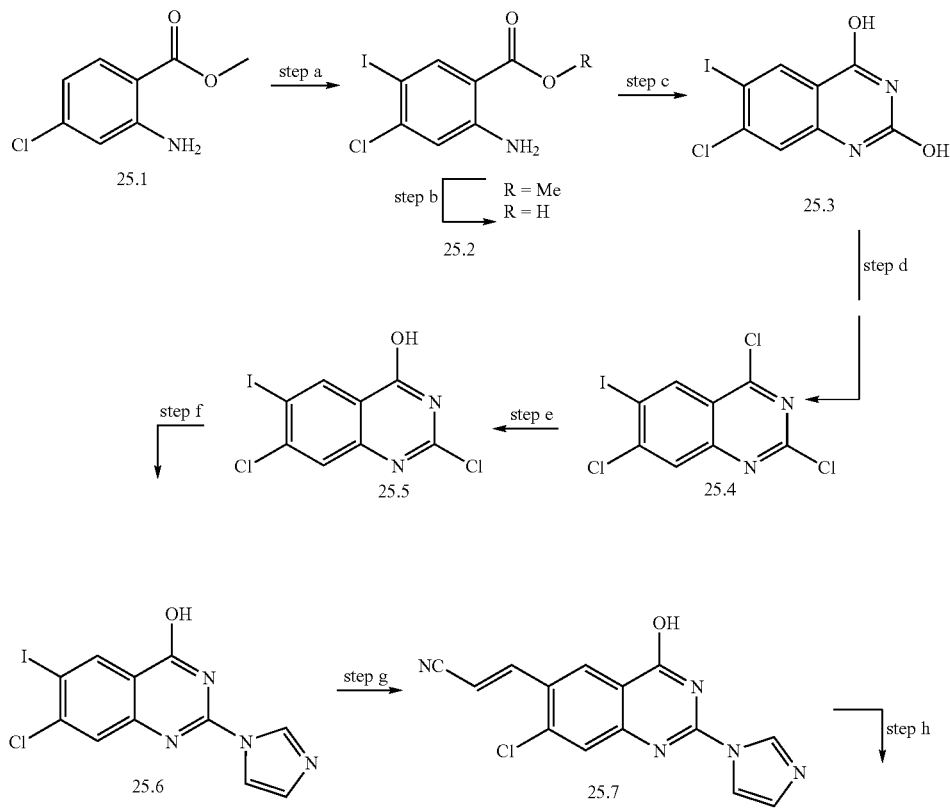

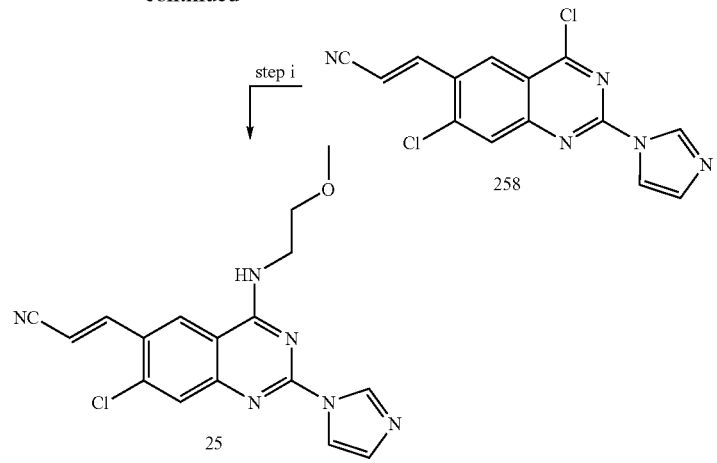

Preparation of Compound 25

(a) Methyl 2-amino-4-chloro-5-iodobenzoate (25.1). A solution of 49.5 g of methyl 2-amino-4-chlorobenzoate (267 mmol, 1.0 equiv) in 1 L acetic acid was cooled to 0° C. followed by the addition of 60 g N-iodosuccinimide. The solution was allowed to stir at 0° C. for 30 min, followed by removal of the cooling bath. The solution was allowed to warm to rt with stirring overnight. The slurry was then poured into 4 L water and the resulting slurry was stirred for 30 min. The suspension was then filtered and washed 3×H$_2$O. The solid was then diluted with 1 L CH$_2$Cl$_2$ and washed twice with water, once with sat. NaHCO$_3$, and once with 1.0 M Na$_2$S$_2$O$_3$. The resulting solution was dried (Na$_2$SO$_4$) and concentrated under reduced pressure. Purification by flash chromatography (SiO$_2$, 1:1 CH$_2$Cl$_2$:Hexanes) followed by trituration with 1:1 CH$_2$Cl$_2$:Hexanes gave the product as a white crystalline solid 69.24 g (222 mmol). $^1$H NMR (CDCl$_3$, 400 MHz) δ 8.27 (s, 1H), 7.28 (s, 1H), 6.84 (s, 1H), 3.95 (s, 3H); MS: ESI(+) m/z 312.0 (M+H$^+$).

(b) 2-Amino-4-chloro-5-iodobenzoic acid (25.2). Methyl 2-amino-4-chloro-5-iodobenzoate (25.1) (44.10 g, 141.8 mmol, 1.0 equiv) was suspended in 250 mL of a 10/3/3 mixture of MeOH/H$_2$O/THF followed by the addition of 6.10 g lithium hydroxide (254.7 mmol, 1.8 equiv). The solution was heated to 53° C., allowed to stir for 2 h, and then allowed to cool to rt. The volatiles were then removed under reduced pressure and the pH of the remaining aqueous solution was adjusted to 6.5 with 1.0 N HCl. The solution was then extracted 2×Et$_2$O and the organics were dried (MgSO$_4$) and concentrated under reduced pressure to give 42.08 g (141.5 mmol) of the product as a white solid.

(c) 7-Chloro-6-iodoquinazolindione (25.3). 2-Amino-4-chloro-5-iodobenzoic acid (25.2) (42.08 g, 141.5 mmol, 1.0 equiv) was dissolved in 880 mL THF followed by the sequential addition of 330 mL H$_2$O, 11.53 g KOCN (212 mmol, 1.5 equiv), and 10 mL acetic acid. After stirring for 30 min another 11.53 g (212 mmol, 1.5 equiv) KOCN was added. The solution was allowed to stir for an additional 17 h, followed by the addition of another portion of KOCN (11.53 g, 1.5 equiv). Following stirring for 3 h, sodium hydroxide (189 g) was added over a period of 1 h. The solution was allowed to stir for an additional 21 h, at which point the volatiles were removed under reduced pressure. The white suspension was diluted with 1.0 N HCl, and then further diluted with 4.0 N HCl to pH 1.0. The resulting white solid was removed by filtration. The solid was then triturated (3×Et$_2$O), filtered, and dried under vacuum for 12 h to give 32.92 g (102 mmol) of the product as an off white solid.

(d) 2,4,7-Trichloro-6-iodoquinazoline (25.4). 7-Chloro-6-iodoquinazolindione (25.3) (32.92 g, 101 mmol, 1.0 equiv) was suspended in 200 mL phosphorousoxychloride and heated to 80° C. The suspension was stirred for 30.5 h, followed by the addition of 35 mL N,N-dimethylaniline. After stirring for an additional 18 h, the hot solution was poured onto water ice. When the ice had melted the brown solid was removed via filtration. The solid was washed 2×H$_2$O and allowed to dry. Purification via flash chromatography (SiO$_2$, 50–75% CH$_2$Cl$_2$/hexanes) gave the product as a light yellow solid 23.72 g (66.0 mmol).

(e) 2,7-Dichloro-6-iodo-4-quinazolinone (25.5). 2,4,7-Trichloro-6-iodoquinazoline (25.4) (23.72 g, 65.74 mmol, 1.0 equiv) was dissolved in 275 mL EtOH and the solution was cooled to 0° C. followed by the addition of a solution of 8 g NaOAc in 160 mL 1:1 AcOH:H$_2$O. The solution was stirred at rt for 20 h, and was then heated to 40° C. After stirring for an additional 24 h the solution was cooled to 0° C. and the white solid was filtered off and washed 2×H$_2$O. The aqueous solution was extracted 1×CH$_2$Cl$_2$ (800 mL) and dried (Na$_2$SO$_4$). The white solid was combined with the CH$_2$Cl$_2$ and the resulting solution was concentrated under reduced pressure to give the product as a white solid 20.59 g (60.4 mmol).

(f) 7-Chloro-2-(imidazol-1-yl)-6-iodo-4-quinazolinone (25.6). 2,7-Dichloro-6-iodo-4-quinazolinone (25.5) (4.77 g, 14.02 mmol, 1.0 equiv) was combined with 2.86 g imidazole (42.06 mmol, 3.0 equiv) and 1.15 gNaOAc (14.02 mmol, 1.0 equiv) in 80 mL EtOH. The resulting suspension was heated to 80° C. overnight. The solution was then removed from the hot bath and diluted with 1 N HCl. The solution was then extracted (3×CHCl$_3$), washed (1×1 N HCl), dried (MgSO$_4$), and concentrated under reduced pressure. Purification via flash chromatography (SiO$_2$, 5% MeOH/CH$_2$Cl$_2$-20% MeOH/THF) gave 4.13 g of the product (11.1 mmol) as a tan solid. $^1$H NMR (DMSO-d$_6$, 400 MHz) δ 13.7 (broad s, 1 H), 8.62 (s, 1 H), 8.50 (s, 1 H), 7.98 (s, 1 H), 7.79 (s, 1 H), 7.17 (s, 1 H); MS: ESI(−) m/z 371.0 (M−H).

(g) 7-Chloro-2-(imidazol-1-yl)-6-(2-cyanoethylene-1-yl)-4-quinazolinone (25.7). 7-Chloro-2-(imidazol-1-yl)-6-iodo-4-quinazolinone (25.6) (4.13 g, 11.1 mmol, 1.0 equiv) was combined with 1.0 g bistriphenylphosphinepalladium chloride (1.42 mmol, 0.13 equiv) in 30 mL DMF followed by the addition of 2.32 mL Hunig's base (13.32 mmol, 1.2 equiv).

The DMF solution was purged via bubbling nitrogen gas through the solution for 10 min, followed by the addition of 3.68 mL acrylonitrile (55.0 mmol, 5.0 equiv). The solution was then placed in an 80° C. bath. After stirring for 60 min, the temperature was raised to 120° C. over a period of 30 min. After heating at 120° C. for an additional 5 h, the solution was removed from the heat bath, and the DMF was removed under reduced pressure. The resulting solid was triturated with hexanes and 1:3 hexanes:$CH_2Cl_2$. The solid was then suspended in 3 N HCl and stirred rapidly for 3 h. The solid was then filtered, washed 2×$H_2O$, and dried under vacuum to give 2.23 g of the product as a mixture of cis and trans alkene isomers (7.5 mmol).

(h) 4,7-Dichloro-2-(imidazol-1-yl)-6-(2-cyanoethylene-1-yl)quinazoline (25.8). 937 mg of 7-chloro-2-(imidazol-1-yl)-6-(2-cyanoethylene-1-yl)-4-quinazolinone (25.7) (3.15 mmol, 1.0 equiv) was suspended in 30 mL $POCl_3$ and the slurry was heated to 80° C. After 15 h the solution was removed from heat and the majority of the $POCl_3$ was removed under reduced pressure. The flask was then filled with ice. After the ice had melted the resulting aqueous suspension was extracted 3×5% MeOH/$CH_2Cl_2$, dried ($Na_2SO_4$), and concentrated under reduced pressure. Purification by flash chromatography ($SiO_2$, 0–10% MeOH/$CH_2Cl_2$) gave the product as a red solid (823 mg, 2.6 mmol).

(i) E-7-Chloro-6-(2-cyanoethylene-1-yl)-2-(imidazol-1-yl)$_4$-(2methoxyethyl-1-amino)quinazoline (25.9). 4,7-Dichloro-2-(imidazol-1-yl)-6-(2-cyanoethylene-1-yl) quinazoline (25.8) (30 mg, 0.0952 mmol, 1.0 equiv) was suspended in 3.0 mL EtOH followed by the addition of four small drops of 2-methoxyethylamine. The reaction was allowed to stir for 30 min, diluted with 0.1 N HCl, and extracted 3×$CHCl_3$. The solution was dried ($Na_2SO_4$), and concentrated under reduced pressure. Purification by flash chromatography ($SiO_2$, 5% MeOH/$CH_2Cl_2$) gave the product as a red solid 21 mg (0.059 mmol). $^1$H NMR (DMSO-$d_6$, 400 MHz) δ 9.0 (m, 1 H), 8.84 (s, 1 H), 8.62 (s, 1 H), 7.95 (s, 1 H), 7.89 (d, J=16.5 Hz, 1 H), 7.79 (s, 1 H), 7.11 (s, 1 H), 6.47 (d, J=16.5 Hz, 1 H), 3.85 (m, 2 H), 3.65 (m, 2 H), 3.31 (s, 3 H).

Example 26

The compounds below were prepared according to the described methods above and provided the indicated physical data, consistent with the assigned structure.

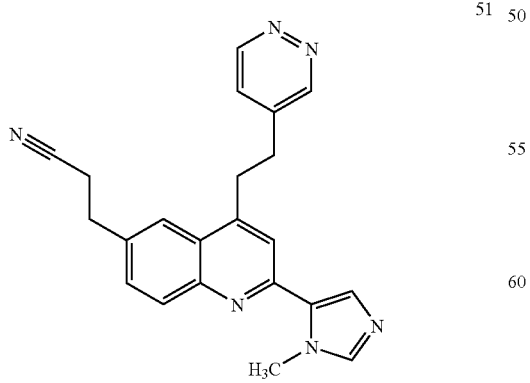

Compound 51 was prepared using Method A (Preparation of Compounds, Scheme 3). LCMS (M+H) 369.

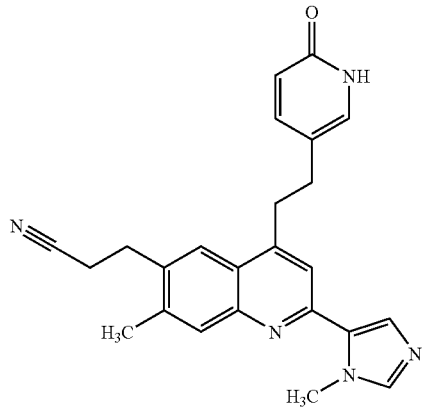

Compound 52 was prepared using Method C and B (Preparation of Compounds, Scheme 3). LCMS (M+H) 398.

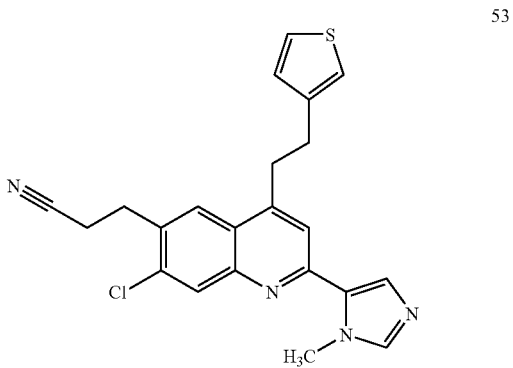

Compound 53 was prepared using Method C and B (Preparation of Compounds, Scheme 3). LCMS (M+H) 407.

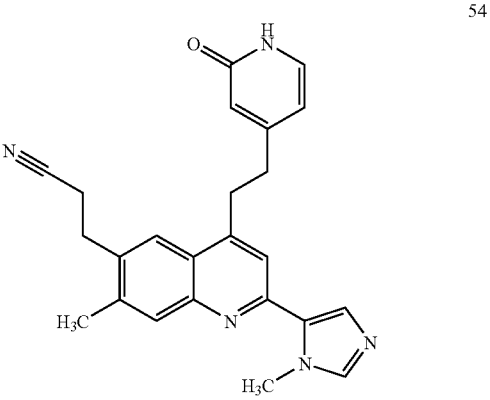

Compound 54 was prepared using Method C and B (Preparation of Compounds, Scheme 3). LCMS (M+H) 398.

55

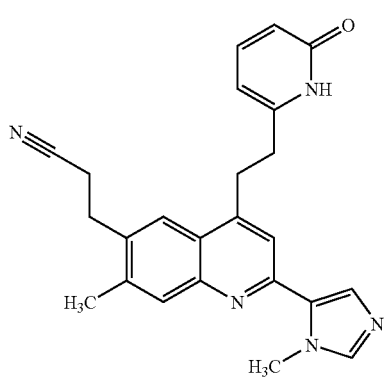

Compound 55 was prepared using Method C and B (Preparation of Compounds, Scheme 3). LCMS (M+H) 398.

56

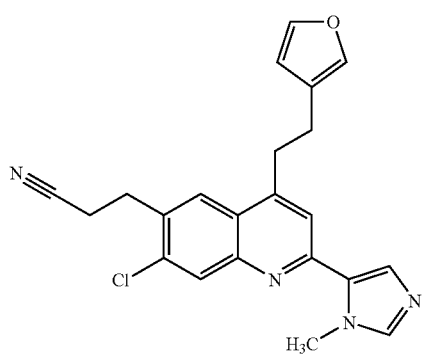

Compound 56 was prepared using Method C and B (Preparation of Compounds, Scheme 3). LCMS (M+H) 391.

57

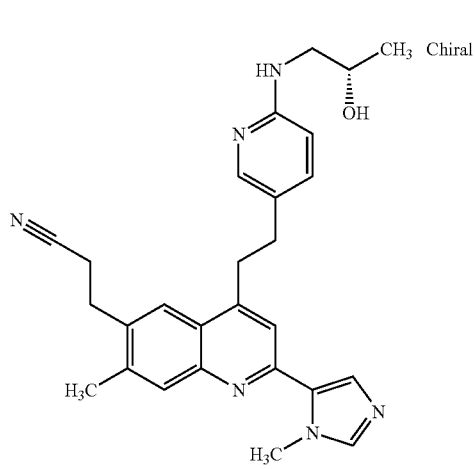

Compound 57 was prepared using Method C and B (Preparation of Compounds, Scheme 3). LCMS (M+H) 455.

58

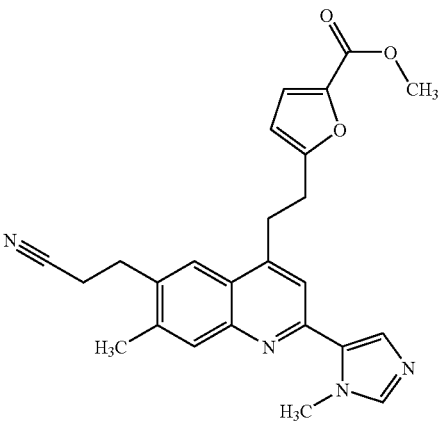

Compound 58 was prepared using Method C and B (Preparation of Compounds, Scheme 3). LCMS (M+H) 429.

59

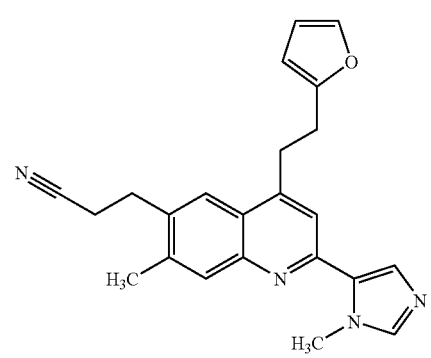

Compound 59 was prepared using Method C and B (Preparation of Compounds, Scheme 3). LCMS (M+H) 371.

60

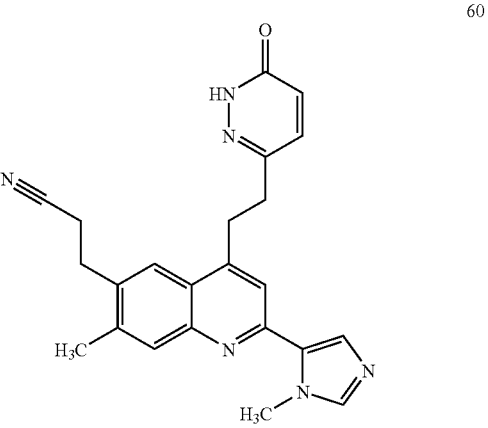

Compound 60 was prepared using Method C and B (Preparation of Compounds, Scheme 3). LCMS (M+H) 399.

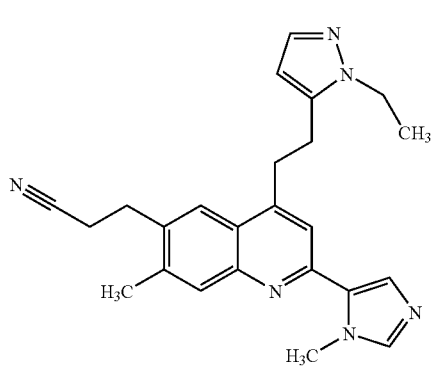

61

Compound 61 was prepared using Method C and B (Preparation of Compounds, Scheme 3). LCMS (M+H) 339.

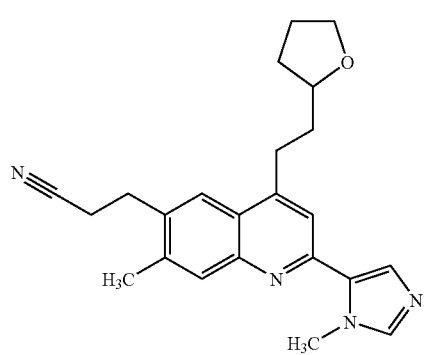

64

Compound 64 was prepared using Method C and B (Preparation of Compounds, Scheme 3). LCMS (M+H) 375.

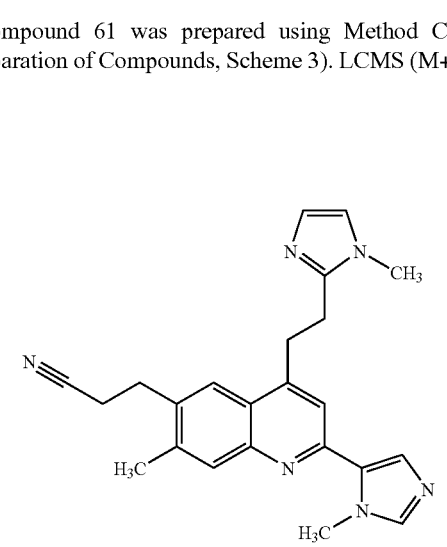

62

Compound 62 was prepared using Method C and B (Preparation of Compounds, Scheme 3). LCMS (M+H) 385.

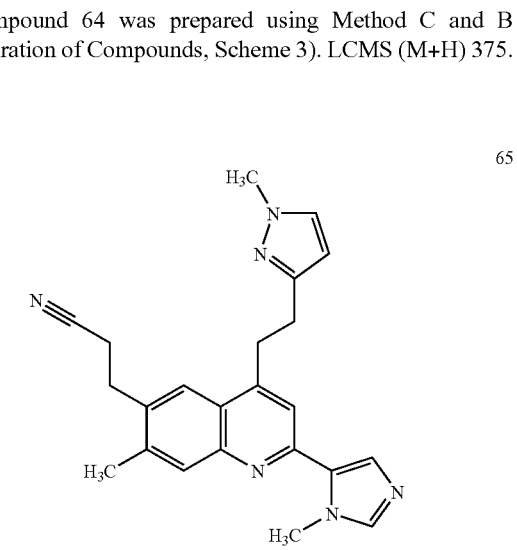

65

Compound 65 was prepared using Method C and B (Preparation of Compounds, Scheme 3). LCMS (M+H) 385.

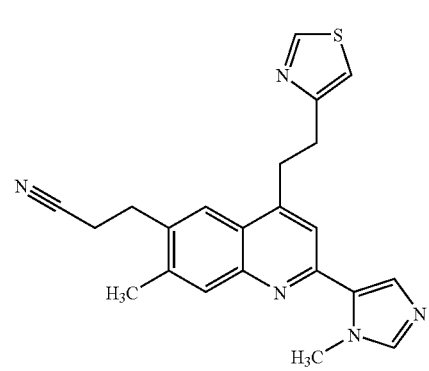

63

Compound 63 was prepared using Method C and B (Preparation of Compounds, Scheme 3). LCMS (M+H) 388.

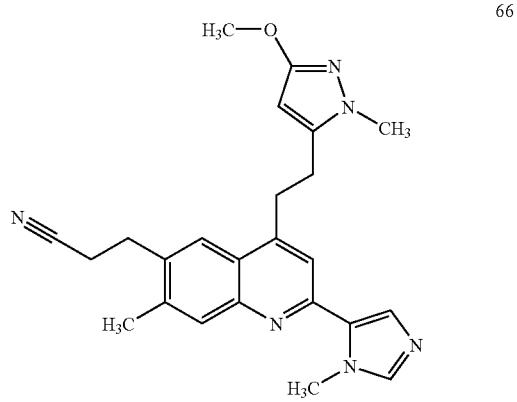

66

Compound 66 was prepared using Method C and B (Preparation of Compounds, Scheme 3). LCMS (M+H) 414.

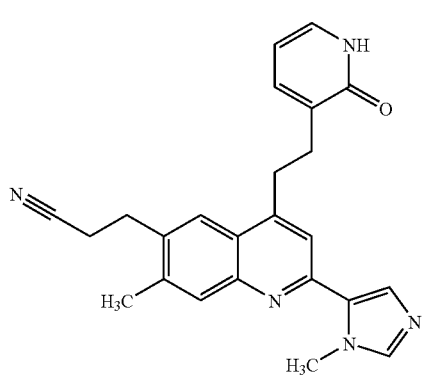

Compound 67 was prepared using Method C and B (Preparation of Compounds, Scheme 3). LCMS (M+H) 398.

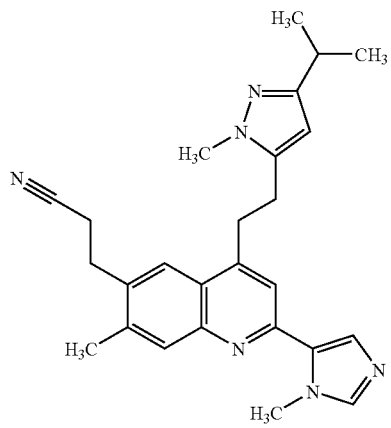

Compound 70 was prepared using Method C and B (Preparation of Compounds, Scheme 3). LCMS (M+H) 427.

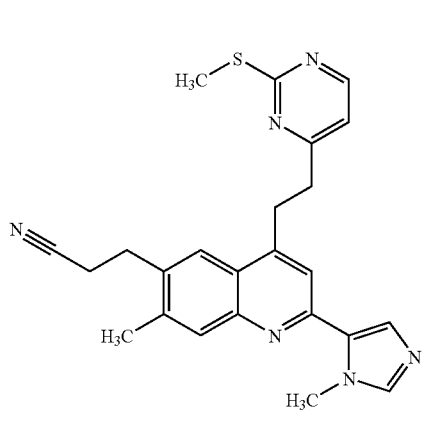

Compound 68 was prepared using Method C and B (Preparation of Compounds, Scheme 3). LCMS (M+H) 429.

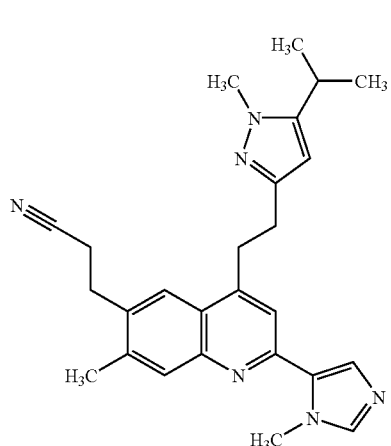

Compound 71 was prepared using Method C and B (Preparation of Compounds, Scheme 3). LCMS (M+H) 427.

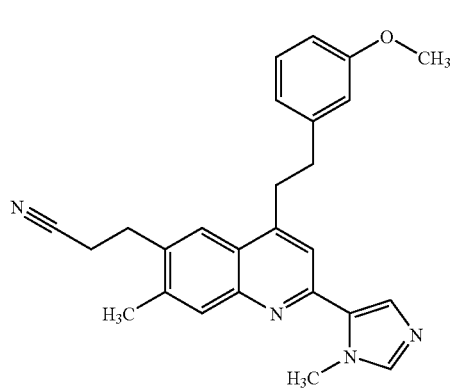

Compound 69 was prepared using Method C and B (Preparation of Compounds, Scheme 3). LCMS (M+H) 411.

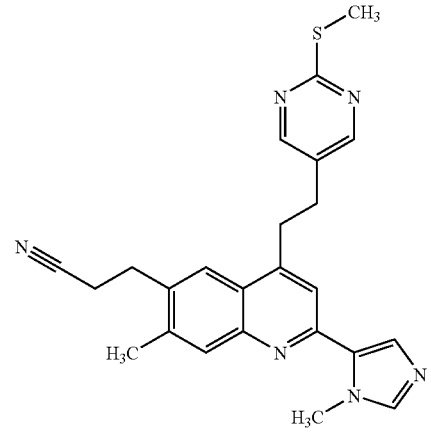

Compound 72 was prepared using Method C and B (Preparation of Compounds, Scheme 3). LCMS (M+H) 429.

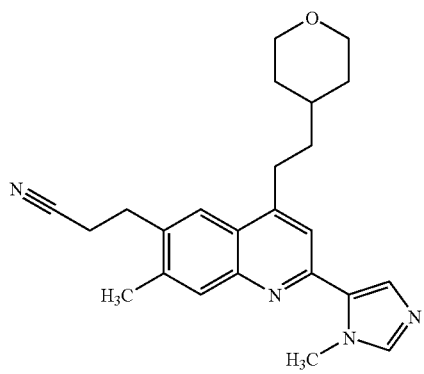

Compound 73 was prepared using Method C and B (Preparation of Compounds, Scheme 3). LCMS (M+H) 389.

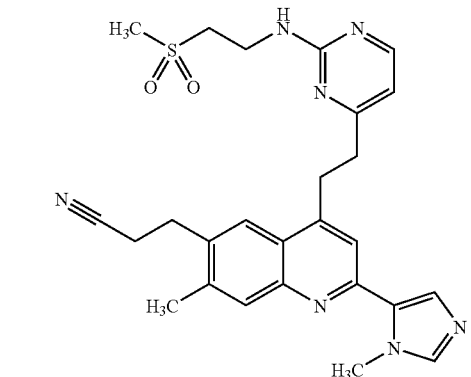

Compound 76 as prepared using Method C and B (Preparation of Compounds, Scheme 3). LCMS (M+H) 504.

Compound 74 was prepared using Method C and B (Preparation of Compounds, Scheme 3). LCMS (M+H) 426.

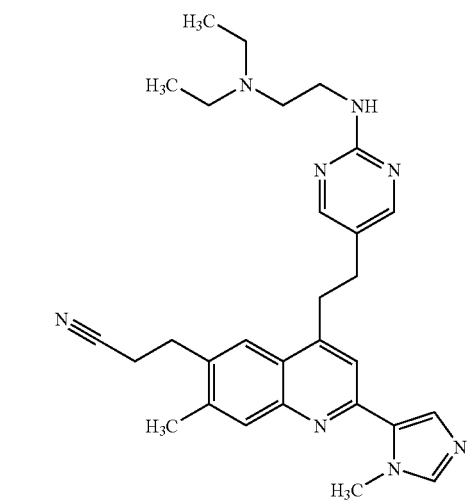

Compound 77 was prepared using Method C and B (Preparation of Compounds, Scheme 3). LCMS (M+H) 497.

Compound 75 was prepared using Method C and B (Preparation of Compounds, Scheme 3). LCMS (M+H) 497.

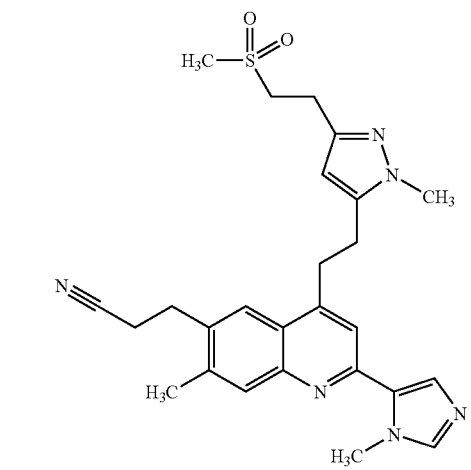

Compound 78 was prepared using Method C and B (Preparation of Compounds, Scheme 3). LCMS (M+H) 491.

Example 79

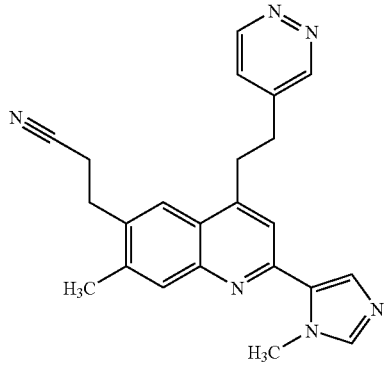

Compound 79 was prepared using Method B, see Example 3.

Example 80

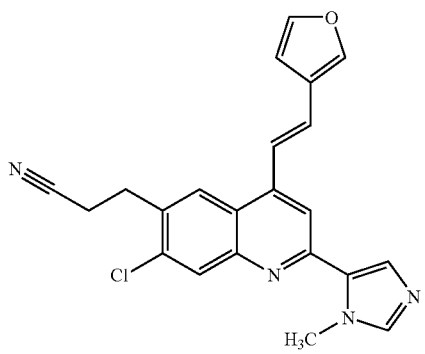

Compound 80 was prepared using Method C (Preparation of Compounds, Scheme 3).

Example 81

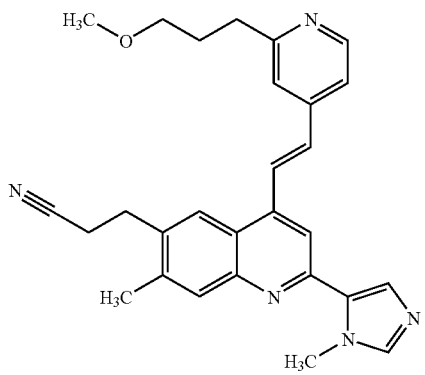

Compound 81 was prepared using Method C (Preparation of Compounds, Scheme 3).

Example 82

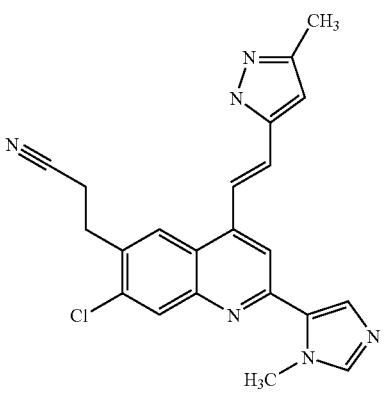

Compound 82 was prepared using Method C (Preparation of Compounds, Scheme 3).

Example 83

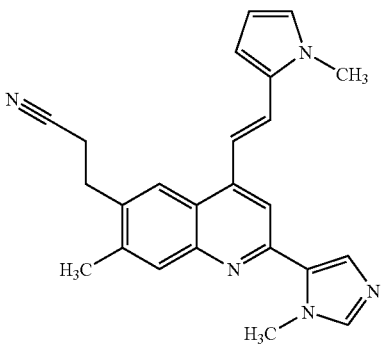

Compound 83 was prepared using Method C (Preparation of Compounds, Scheme 3).

Example 84

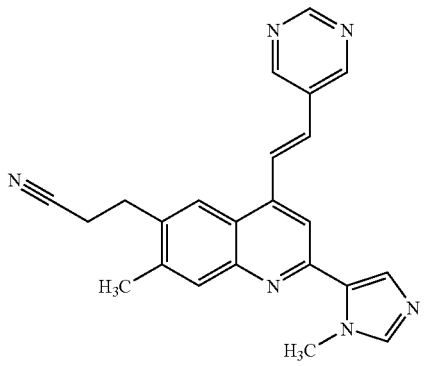

Compound 84 was prepared using Method C (Preparation of Compounds, Scheme 3).

Example 27

This example provides an assay that is useful in evaluating and selecting a compound that modulates IKK.

Assay Protocol for Measuring IKKβ Enzyme Inhibition 96 well polystyrene microtiter plates were coated with Neutravidin (10 μg/mL in PBS, overnight at 4° C.). The coating solution was removed and in 80 μL/well a kinase reaction mixture was added (20 mM Tris-HCl, pH 7.5, 10 mM MgCl$_2$, 2 mM EGTA, 1 mM NaF, 0.5 mM benzamidine, 1 mM DTT, 0.1% NP-40, 10 μM ATP, 1 μM of biotinylated substrate peptide KKERLLDDRHDSGLDSMKDEEYEQ GK-bio, sequence derived from IκBα). In 10 μL/well in DMSO test compounds were added covering a final concentration range from 1 nM to 30 μM. Recombinant full-length IKKβ enzyme produced in a baculovirus system in insect cells was added in 10 μL buffer containing Tris-HCl pH 7.5 20 mM, EGTA 2 mM, benzamidine 0.5 mM, DTT 1 mM, NP-40 0.1%, MgCl$_2$ 10 mM to initiate the kinase reaction. The reaction mixture was incubated at room temperature for 45 min. During this incubation the substrate peptide gets phosphorylated by IKKβ and gets captured onto the well's surface by Neutravidin. The plate was washed 3× with 150 μL distilled water to terminate the reaction and remove components of the reaction mixture.

A conventional chemiluminescent ELISA detection technique was initiated by adding 100 μL/well primary antibody (custom-made monoclonal antibody generated to recognize the phosphorylated epitope in the substrate peptide; used at 1:10,000 dilution) premixed with horseradish peroxidase (HRP) conjugated anti-mouse secondary antibody (commercially available from several sources; used at 1:10,000 dilution) in PBS containing 2% BSA. The solution was incubated at room temperature for 40 min on a shaker, then washed 3× with 150 μL of water. 100 μL/well 10× diluted SuperSignal HRP substrate (from Pierce) was added and after 5 min incubation the chemiluminescent signal was captured by a Labsystems LuminoSkan luminometer. The point of 50% inhibition of IKKβ enzyme activity (IC$_{50}$) was determined by curve fitting with the LSW data analysis software (MDL, San Leandro, Calif.).

The compounds provided in Examples 1–25 all displayed IC$_{50}$ values of less than or equal to about 30 μM in the above assay.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (I):

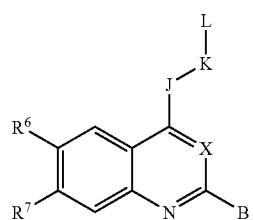

or a pharmaceutically acceptable salt or prodrug thereof, wherein

X is N or CR$^5$;

J is selected from the group consisting of (C$_1$–C$_4$)alkylene, (C$_2$–C$_4$)alkenylene, (C$_2$–C$_4$)alkynylene, C(=Y), NR$^1$, O, S(O)$_m$, C(=Y)NR$^1$, (C$_1$–C$_4$)alkylene-NR$^1$, (C$_1$–C$_4$)alkylene-O and C(R$^2$)=N;

K is selected from the group consisting of a bond, (C$_1$–C$_4$)alkylene, C(=Y), NR$^1$, O and S(O)$_m$;

L is selected from the group consisting of H, (C$_1$–C$_6$)alkyl, OR$^1$, hetero(C$_1$–C$_6$)alkyl, aryl, heteroaryl, NR$^2$R$^3$, C(=Y)R$^2$, C(=Y)NR$^2$R$^3$, C(=Y)OR$^2$, (C$_1$–C$_4$)alkyl-C(=Y)R$^2$, (C$_1$–C$_4$)alkyl-C(=Y)NR$^2$R$^3$, and (C$_1$–C$_4$)alkyl-C(=Y)OR$^2$;

optionally, J may be combined with K or L to form a 5-, 6-, 7- or 8-membered ring containing from 0 to 3 heteratoms selected from the group consisting of N, O and S;

optionally, K may be combined with L to form 5-, 6-, 7- or 8-membered ring containing from 0 to 3 heteratoms selected from the group consisting of N, O and S;

B is a five- or six-membered aromatic ring system containing at least one heteroatom selected from the group consisisting of N, O and S;

Y is selected from the group consisting of O, S, NR$^1$, N(CN) and NOR$^1$;

R$^1$, R$^2$ and R$^3$ are independently selected from the group consisting of H, (C$_1$–C$_{10}$)alkyl, (C$_3$–C$_{10}$)alkenyl, (C$_2$–C$_{10}$)alkynyl, (C$_1$–C$_{10}$)heteroalkyl, (C$_3$–C$_{10}$)cycloalkyl, (C$_3$–C$_{10}$)cycloalkyl-alkyl, (C$_3$–C$_{10}$)cycloheteroalkyl-alkyl, (C$_3$–C$_{10}$)cycloheteroalkyl, aryl, aryl (C$_1$–C$_4$)alkyl, aryl(C$_1$–C$_4$)heteroalkyl, heteroaryl (C$_1$–C$_4$)alkyl, heteroaryl(C$_1$–C$_4$)heteroalkyl and fluoro (C$_1$–C$_6$)alkyl;

optionally, when R$^2$ and R$^3$ are attached to the same nitrogen atom, R$^2$ and R$^3$ may be combined with the nitrogen atom to form a 5-, 6- or 7-membered ring containing from 1 to 3 heteratoms selected from the group consisting of N, O and S;

R$^5$, R$^6$ and R$^7$ are independently selected from the group consisting of H, halogen, (C$_1$–C$_4$)fluoroalkyl, (C$_1$–C$_6$) alkyl, (C$_2$–C$_6$)alkenyl, (C$_2$–C$_6$)alkynyl, (C$_1$–C$_6$)heteroalkyl, (C$_1$–C$_6$)alkoxy, (C$_1$–C$_6$)thioalkoxy, amino, (C$_1$–C$_6$)alkylamino, di(C$_1$–C$_6$)alkylamino, (C$_3$–C$_{10}$) cycloalkyl, (C$_3$–C$_{10}$)cycloalkyl-alkyl, (C$_3$–C$_{10}$)cycloheteroalkyl, (C$_3$–C$_{10}$)cycloheteroalkyl-alkyl, cyano, cyano-(C$_1$–C$_6$)alkyl, cyano-(C$_2$–C$_6$)alkenyl, nitro, (C$_1$–C$_6$)acyl, (C$_1$–C$_6$)acylamino, (C$_1$–C$_6$)alkoxycarbonyl, (C$_1$–C$_6$)alkoxycarbonyl (C$_1$–C$_6$)alkyl, CONH$_2$, CO—NH—(C$_1$–C$_6$)alkyl, CO—N[(C$_1$–C$_6$)alkyl]$_2$, SO$_2$NH$_2$, SO$_2$NH—(C$_1$–C$_6$)alkyl, SO$_2$N—[(C$_1$–C$_6$) alkyl]$_2$ and (C$_1$–C$_6$)heteroalkoxy;

optionally, R$^6$ and R$^7$ may be combined to form a new 5- or 6-membered ring containing from 0 to 3 heteratoms selected from the group consisting of N, O and S;

the subscript m is an integer of from 0 to 2;

with the proviso that the compound is not

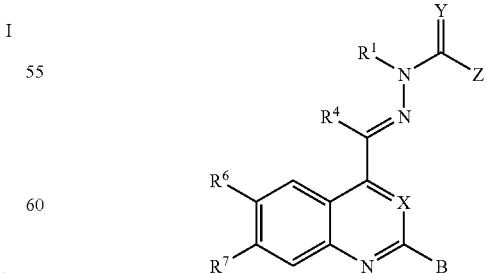

wherein

Z is selected from the group consisting of H, (C$_1$–C$_{10}$) alkyl, (C$_3$–C$_{10}$)cycloalkyl, (C$_3$–C$_{10}$)cycloalkyl-alkyl, (C$_2$–C$_{10}$)alkenyl, (C$_2$–C$_{10}$)alkynyl and NR$^2$R$^3$; and $R^4$ is selected from the group consisting of H, $(C_1-C_{10})$alkyl, $(C_3-C_6)$cycloalkyl, $(C_4-C_7)$cycloalkyl-alkyl, $(C_2-C_6)$alkenyl and $(C_2-C_6)$alkynyl.

2. A compound having the formula (I):

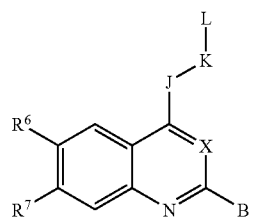

I or a pharmaceutically acceptable salt or prodrug thereof, wherein

X is N or $CR^5$;

J is selected from the group consisting of $(C_1-C_4)$alkylene, $(C_2-C_4)$alkenylene, $(C_2-C_4)$alkynylene, C(=Y), $NR^1$, O, $S(O)_m$, C(=Y)$NR^1$, $(C_1-C_4)$alkylene-$NR^1$, $(C_1-C_4)$alkylene-O and $C(R^2)$=N;

K is selected from the group consisting of a bond, $(C_1-C_4)$alkylene, C(=Y), O and $S(O)_m$;

L is selected from the group consisting of H, $(C_1-C_6)$alkyl, $OR^1$, hetero$(C_1-C_6)$alkyl, aryl, heteroaryl, $NR^2R^3$, C(=Y)$R^2$, C(=Y)$NR^2R^3$, C(=Y)$OR^2$, $(C_1-C_4)$alkyl-C(=Y)$R^2$, $(C_1-C_4)$alkyl-C(=Y)$NR^2R^3$ and $(C_1-C_4)$alkyl-C(=Y)$OR^2$;

optionally, J may be combined with K or L to form a 5-, 6-, 7- or 8-membered ring containing from 0 to 3 heteroatoms selected from the group consisting of N, O and S;

B is a five- or six-membered aromatic ring system containing at least one heteroatom selected from the group consisisting of N, O and S;

Y is selected from the group consisting of O, S, $NR^1$, N(CN) and $NOR^1$;

$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_1-C_{10})$heteroalkyl, $(C_3-C_{10})$cycloalkyl, $(C_3-C_{10})$cycloalkyl-alkyl, $(C_3-C_{10})$cycloheteroalkyl-alkyl, $(C_3-C_{10})$cycloheteroalkyl, aryl, aryl$(C_1-C_4)$alkyl, aryl$(C_1-C_4)$heteroalkyl, heteroaryl$(C_1-C_4)$alkyl, heteroaryl$(C_1-C_4)$heteroalkyl and fluoro$(C_1-C_6)$alkyl;

optionally, when $R^2$ and $R^3$ are attached to the same nitrogen atom, $R^2$ and $R^3$ may be combined with the nitrogen atom to form a 5-, 6- or 7-membered ring containing from 1 to 3 heteroatoms selected from the group consisting of N, O and S;

$R^5$, $R^6$ and $R^7$ are independently selected from the group consisting of H, halogen, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N[$(C_1-C_6)$alkyl]$_2$, $SO_2NH_2$, $SO_2$NH—$(C_1-C_6)$alkyl, $SO_2$N—[$(C_1-C_6)$alkyl]$_2$ and $(C_1-C_6)$heteroalkoxy;

$R^6$ is $(C_1-C_4)$alkyl or $(C_1-C_6)$heteroalkoxy;

optionally, $R^6$ and $R^7$ may be combined to form a new 5- or 6-membered ring containing from 0 to 3 heteroatoms selected from the group consisting of N, O and S; and the subscript m is an integer of from 0 to 2.

3. A compound having the formula (I):

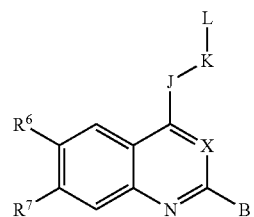

I or a pharmaceutically acceptable salt or prodrug thereof, wherein

X is N or $CR^5$;

J is selected from the group consisting of $(C_1-C_4)$alkylene, $(C_2-C_4)$alkenylene, $(C_2-C_4)$alkynylene, C(=Y), $NR^1$, O, $S(O)_m$, C(=Y)$NR^1$, $(C_1-C_4)$alkylene-$NR^1$, $(C_1-C_4)$alkylene-O and $C(R^2)$=N;

K is selected from the group consisting of a bond, $(C_1-C_4)$alkylene, C(=Y), $NR^1$, O and $S(O)_m$;

L is selected from the group consisting of H, $(C_1-C_6)$alkyl, $OR^1$, hetero$(C_1-C_6)$alkyl, aryl, heteroaryl, $NR^2R^3$, C(=Y)$OR^2$, $(C_1-C_4)$alkyl-C(=Y)$NR^2R^3$, $(C_1-C_4)$alkyl-C(=Y)$R^2$ and $(C_1-C_4)$alkyl-C(=Y)$OR^2$;

optionally, J may be combined with K or L to form a 5-, 6-, 7- or 8-membered ring containing from 0 to 3 heteroatoms selected from the group consisting of N, O and S;

B is a five- or six-membered aromatic ring system containing at least one heteroatom selected from the group consisisting of N, O and S;

Y is selected from the group consisting of O, S, $NR^1$, N(CN) and $NOR^1$;

$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_1-C_{10})$heteroalkyl, $(C_3-C_{10})$cycloalkyl, $(C_3-C_{10})$cycloalkyl-alkyl, $(C_3-C_{10})$cycloheteroalkyl-alkyl, $(C_3-C_{10})$cycloheteroalkyl, aryl, aryl$(C_1-C_4)$alkyl, aryl$(C_1-C_4)$heteroalkyl, heteroaryl$(C_1-C_4)$alkyl, heteroaryl$(C_1-C_4)$heteroalkyl and fluoro$(C_1-C_6)$alkyl;

optionally, when $R^2$ and $R^3$ are attached to the same nitrogen atom, $R^2$ and $R^3$ may be combined with the nitrogen atom to form a 5-, 6- or 7-membered ring containing from 1 to 3 heteroatoms selected from the group consisting of N, O and S;

$R^5$, and $R^7$ are independently selected from the group consisting of H, halogen, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N[$(C_1-C_6)$alkyl]$_2$, $SO_2NH_2$, $SO_2$NH—$(C_1-C_6)$alkyl, $SO_2$N—[$(C_1-C_6)$alkyl]$_2$ and $(C_1-C_6)$heteroalkoxy;

$R^6$ is $(C_1-C_4)$alkyl or $(C_2-C_4)$alkenyl;

optionally, $R^6$ and $R^7$ may be combined to form a new 5- or 6-membered ring containing from 0 to 3 heteratoms selected from the group consisting of N, O and S; and the subscript m is an integer of from 0 to 2.

4. A compound having the formula (I):

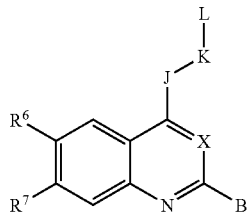

or a pharmaceutically acceptable salt or prodrug thereof, wherein

X is N or $CR^5$;

J is selected from the group consisting of $(C_1-C_4)$alkylene, $(C_2-C_4)$alkenylene, $(C_2-C_4)$alkynylene, C(=Y), $NR^1$, O, $S(O)_m$, C(=Y)$NR^1$, $(C_1-C_4)$alkylene-$NR^1$ and $(C_1-C_4)$alkylene-O;

K is selected from the group consisting of a bond, $(C_1-C_4)$alkylene, C(=Y), $NR^1$, O and $S(O)_m$;

L is selected from the group consisting of H, $(C_1-C_6)$alkyl, $OR^1$, hetero$(C_1-C_6)$alkyl, aryl, heteroaryl, $NR^2R^3$, C(=Y)$R^2$, C(=Y)$NR^2R^3$, C(=Y)$OR^2$, $(C_1-C_4)$alkyl-C(=Y)$R^2$, $(C_1-C_4)$alkyl-C(=Y)$NR^2R^3$, and $(C_1-C_4)$alkyl-C(=Y)$OR^2$;

optionally, J may be combined with K or L to form a 5-, 6-, 7- or 8-membered ring containing from 0 to 3 heteratoms selected from the group consisting of N, O and S;

B is a five- or six-membered aromatic ring system containing at least one heteroatom selected from the group consisisting of N, O and S;

Y is selected from the group consisting of O, S, $NR^1$, N(CN) and $NOR^1$;

$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_1-C_{10})$heteroalkyl, $(C_3-C_{10})$cycloalkyl, $(C_3-C_{10})$cycloalkyl-alkyl, $(C_3-C_{10})$cycloheteroalkyl-alkyl, $(C_3-C_{10})$cycloheteroalkyl, aryl, aryl$(C_1-C_4)$alkyl, aryl$(C_1-C_4)$heteroalkyl, heteroaryl$(C_1-C_4)$alkyl, heteroaryl$(C_1-C_4)$heteroalkyl and fluoro$(C_1-C_6)$alkyl;

optionally, when $R^2$ and $R^3$ are attached to the same nitrogen atom, $R^2$ and $R^3$ may be combined with the nitrogen atom to form a 5-, 6- or 7-membered ring containing from 1 to 3 heteratoms selected from the group consisting of N, O and S;

$R^5$, and $R^7$ are independently selected from the group consisting of H, halogen, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N[$(C_1-C_6)$alkyl]$_2$, $SO_2NH_2$, $SO_2NH$—$(C_1-C_6)$alkyl, $SO_2N$—[$(C_1-C_6)$alkyl]$_2$ and $(C_1-C_6)$heteroalkoxy;

optionally, $R^6$ and $R^7$ may be combined to form a new 5- or 6-membered ring containing from 0 to 3 heteratoms selected from the group consisting of N, O and S; and the subscript m is an integer of from 0 to 2.

5. The compound of claim 1, wherein $R^7$ is selected from the group consisting of H, halogen, $(C_1-C_4)$fluoroalkyl, $CF_3O$, $(C_1-C_4)$alkyl, $(C_2-C_4)$alkenyl, $(C_2-C_4)$alkynyl, $(C_1-C_4)$heteroalkyl, $(C_3-C_{10})$cycloheteroalkyl-alkyl, cyano, cyano-$(C_1-C_6)$alkyl and cyano-$(C_2-C_6)$alkenyl.

6. The compound of claim 5, wherein $R^6$ is substituted with CN, $S(O)_m(C_1-C_6)$alkyl or $(C_1-C_6)$alkoxy.

7. The compound of claim 5, wherein $R^7$ is H, $(C_1-C_4)$alkyl or halogen.

8. The compound of claim 5, wherein $R^6$ is $(C_1-C_4)$alkyl or $(C_2-C_4)$alkenyl substituted with CN, $S(O)_m(C_1-C_6)$alkyl or $(C_1-C_6)$alkoxy and $R^7$ is H, $(C_1-C_4)$alkyl or halogen.

9. The compound of claim 8, having the formula:

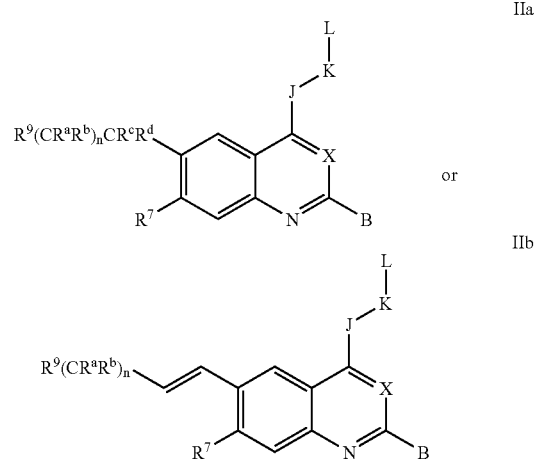

wherein $R^9$ is selected from the group consisting of CN, $S(O)_p(C_1-C_6)$alkyl and $(C_1-C_6)$alkoxy, wherein the subscript p is an integer of from 0 to 2;

$R^a$, $R^b$, $R^c$ and $R^d$ are independently selected from the group consisting of H, halogen, $(C_1-C_6)$alkyl, $(C_1-C_4)$fluoroalkyl, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_3-C_{10})$cycloalkyl-alkyl, $(C_3-C_{10})$cycloheteroalkyl, $(C_3-C_{10})$cycloheteroalkyl-alkyl, cyano, cyano-$(C_1-C_6)$alkyl, cyano-$(C_2-C_6)$alkenyl, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, CO—NH—$(C_1-C_6)$alkyl, CO—N[$(C_1-C_6)$alkyl]$_2$, $SO_2NH_2$, $SO_2NH$—$(C_1-C_6)$alkyl, $SO_2N$—[$(C_1-C_6)$alkyl]$_2$ and $(C_1-C_6)$heteroalkoxy; and the subscript n is an integer of from 0 to 3.

10. The compound of claim 9, wherein $R^a$, $R^b$, $R^c$ and $R^d$ are H.

11. The compound of claim 9, having the formula:

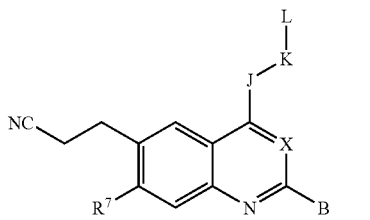
IIIa or

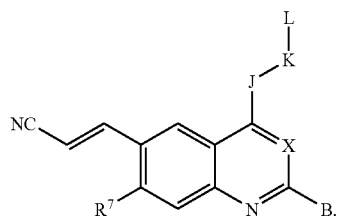
IIIb

12. The compound of claim 9, having the formula:

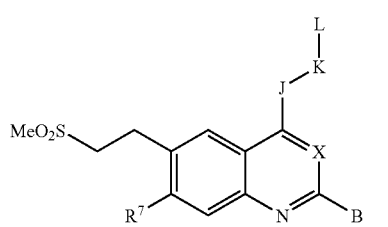
IVa or

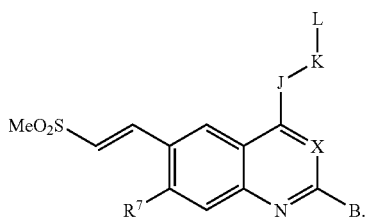
IVb

13. The compound of claim 9, having the formula:

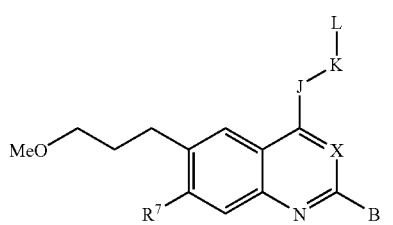
Va or

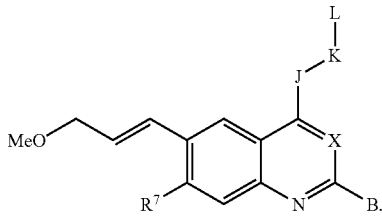
Vb

14. The compound of claim 5, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1,3,4-triazol-1-yl, 1,2,4-triazol-4-yl, thiophenyl, furanyl and pyridyl.

15. The compound of claim 5, wherein B is selected from the group consisting of 1-methylimidazol-5-yl, 5-methylimidazol-1-yl, thiazol-5-yl, imidazol-1-yl and 1,3,4-triazol-1-yl.

16. The compound of claim 5, wherein $R^6$ is $(C_1-C_4)$alkyl or $(C_2-C_4)$alkenyl substituted with CN, $S(O)_m$ or $(C_1-C_6)$alkoxy, $R^7$ is $(C_1-C_4)$alkyl or halogen and B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1,3,4-triazol-1-yl, 1,2,4-triazol-4-yl, thiophenyl, furanyl and pyridyl.

17. The compound of claim 5, wherein $R^6$ is $(C_1-C_4)$alkyl or $(C_2-C_4)$alkenyl substituted with CN, $S(O)_m(C_1-C_6)$alkyl or $(C_1-C_6)$alkoxy, $R^7$ is $(C_1-C_4)$alkyl or halogen and B is selected from the group consisting of 1-methylimidazol-5-yl, 5-methylimidazol-1-yl, thiazol-5-yl, imidazol-1-yl and 1,3,4-triazol-1-yl.

18. The compound of claim 9, having the formula:

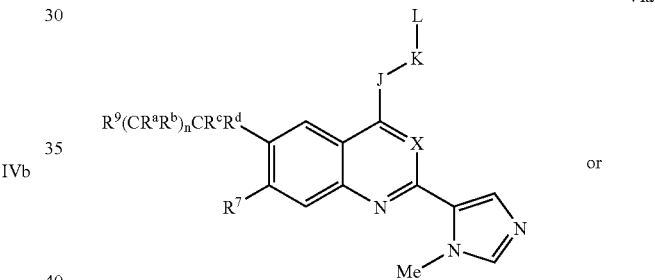
VIa or

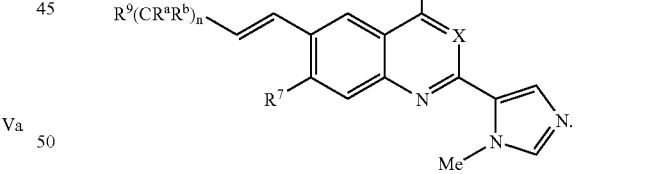
VIb

19. The compound of claim 9, having the formula:

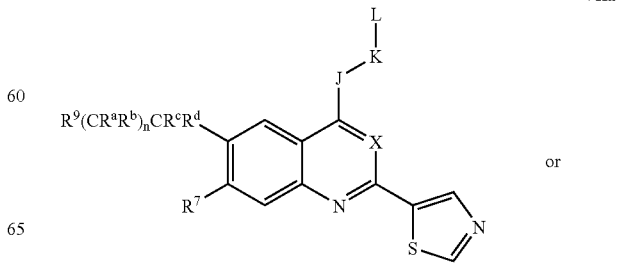
VIIa or

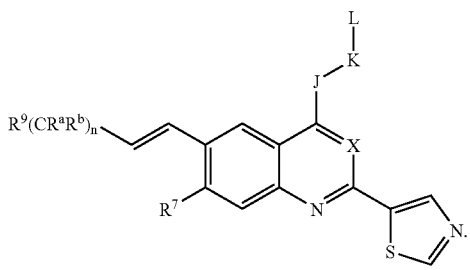

20. The compound of claim 9, having the formula:

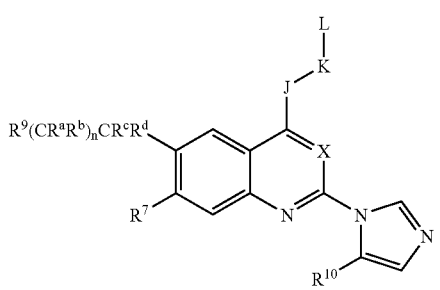

or

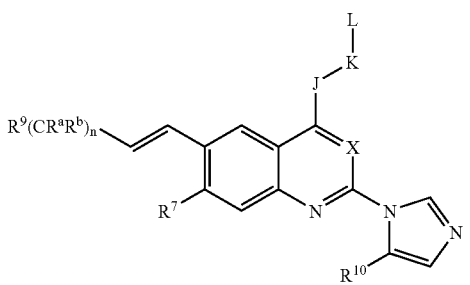

wherein $R^{10}$ is selected from the group consisting of H, $(C_1-C_4)$alkyl, $(C_1-C_4)$fluoroalkyl, and halogen.

21. The compound of claim 9, having the formula:

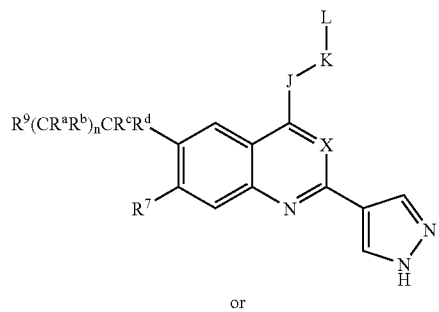

or

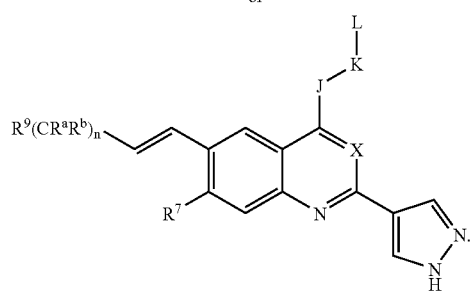

22. The compound of claim 5, wherein L is aryl or heteroaryl.

23. The compound of claim 5, wherein L is selected from the group consisting of phenyl, naphthyl, pyrrolyl, pyrazolyl, imidazolyl, pyrazinyl, oxazolyl, isoxazolyl, thiazolyl, furyl, thienyl, pyridyl, pyrimidyl, pyrimidinyl, pyridazinyl, benzothiazolyl, purinyl, benzimidazolyl, indolyl, isoquinolyl, quinoxalinyl and quinolyl.

24. The compound of claim 5, wherein L is selected from the group consisting of $C(=Y)R^2$, $C(=Y)NR^2R^3$ and $CO_2R^2$.

25. The compound of claim 5, wherein L is $C(O)NR^2R^3$.

26. The compound of claim 5, wherein J is $(C_1-C_4)$ alkylene.

27. The compound of claim 5, wherein J is $(C_2-C_4)$ alkenylene.

28. The compound of claim 5, wherein J is $(C_2-C_4)$ alkynylene.

29. The compound of claim 5, wherein J is $C(=Y)$.

30. The compound of claim 5, wherein J is $NR^1$.

31. The compound of claim 5, wherein J is O.

32. The compound of claim 5, wherein J is $S(O)_m$.

33. The compound of claim 5, wherein J is $C(=Y)NR^1$.

34. The compound of claim 5, wherein J is $(C_1-C_4)$ alkylene-$NR^1$.

35. The compound of claim 5, wherein J is $(C_1-C_4)$ alkylene-$OR^1$.

36. The compound of claim 5, wherein J is $C(R^2)=N$.

37. The compound of claim 5, wherein K is a bond.

38. The compound of claim 5, wherein K is $(C_1-C_4)$ alkylene.

39. The compound of claim 5, wherein K is $C(=Y)$.

40. The compound of claim 5, wherein K is $NR^1$.

41. The compound of claim 5, wherein K is O.

42. The compound of claim 5, wherein K is $S(O)_m$.

43. The compound of claim 5, having a formula selected from the group consisting of X, XI, XII, XIII, XIVa, XIVb, XV, XVI, XVII, XVIIIa, XVIIIb, XIX, XX, XXIa, XXIb, XXII, XXIIIa, XXIIIb and XXIV:

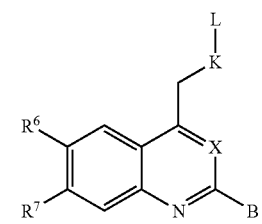

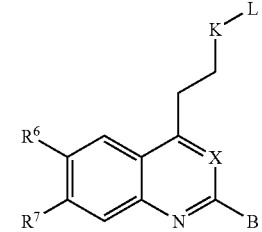

-continued
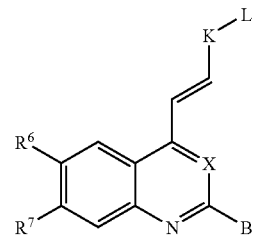
XII
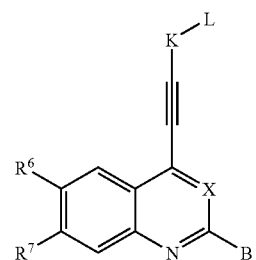
XIII
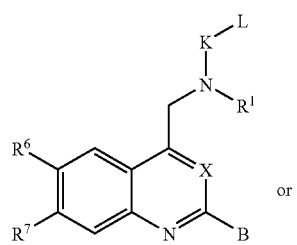
XIVa
or
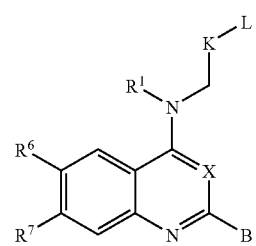
XIVb
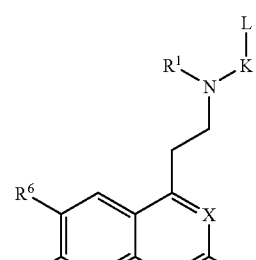
XV
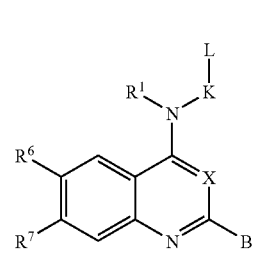
XVI
-continued
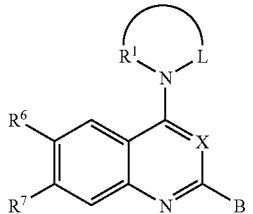
XVII
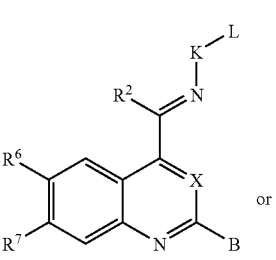
XVIIIa
or
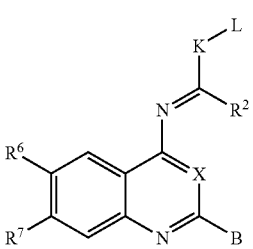
XVIIIb
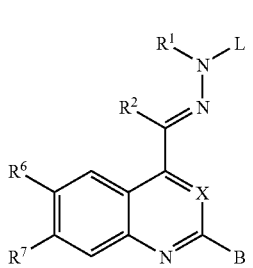
XIX
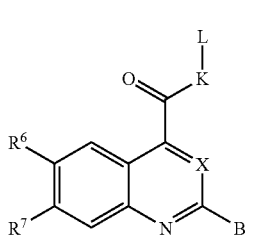
XX
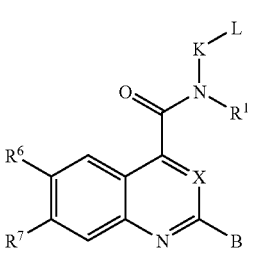
XXIa

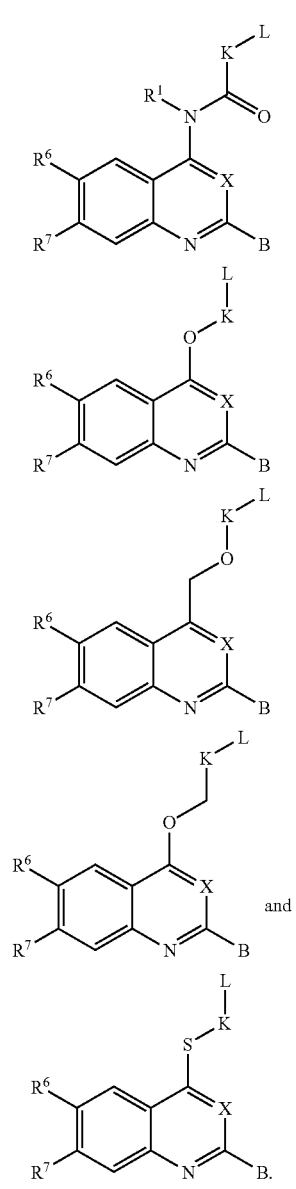
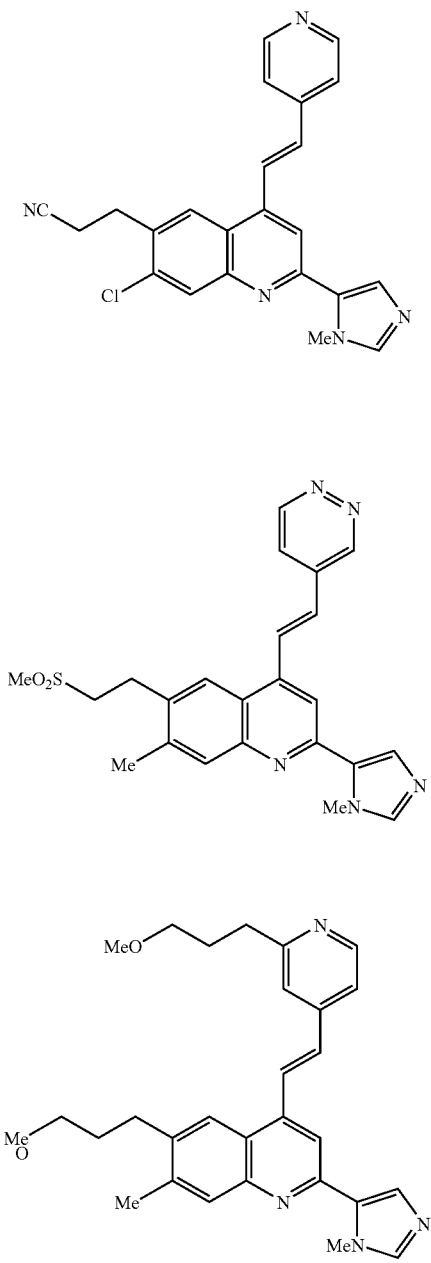
44. A pharmaceutical composition comprising a pharmaceutically acceptable carrier or excipient and a compound of claim 1.
45. A compound of claim 1 having a formula selected from the group consisting of:
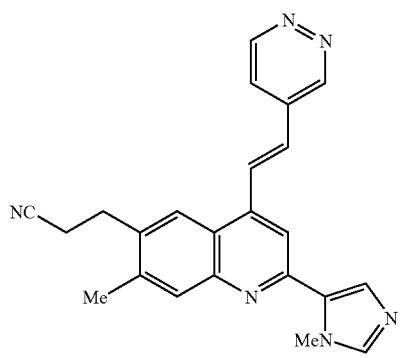
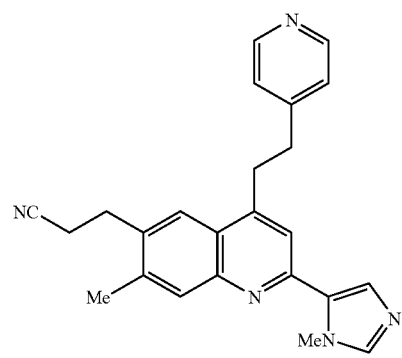

91

-continued

92

-continued

-continued
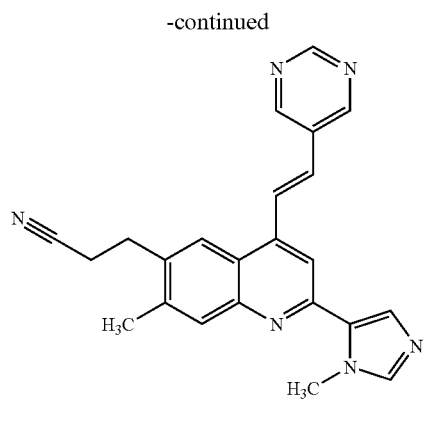
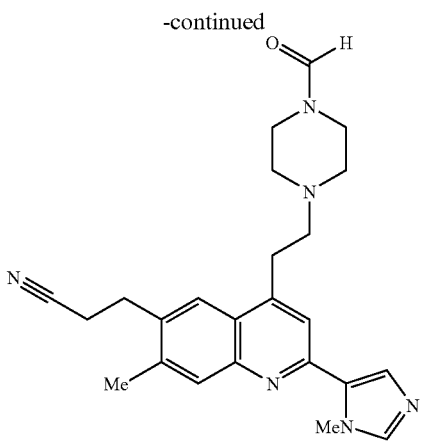
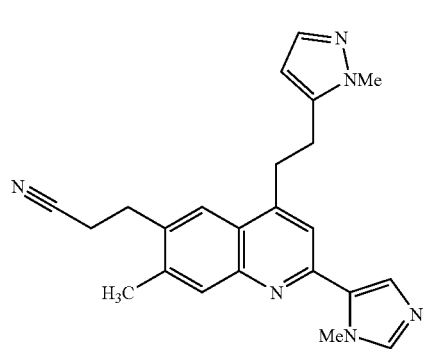
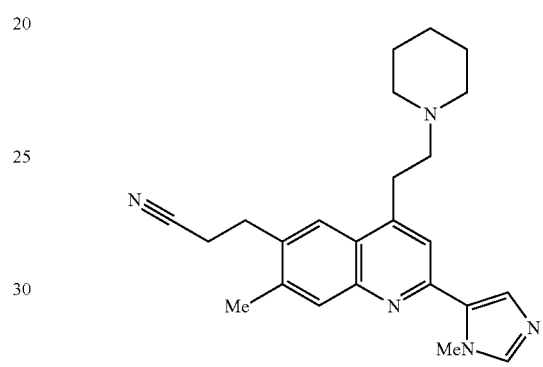
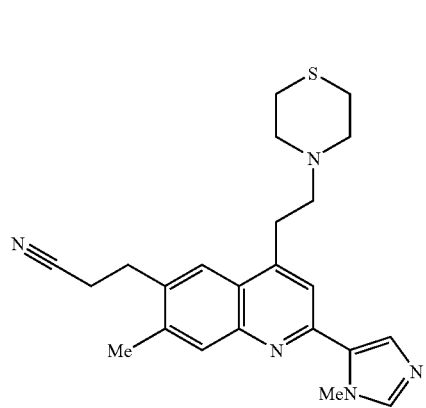
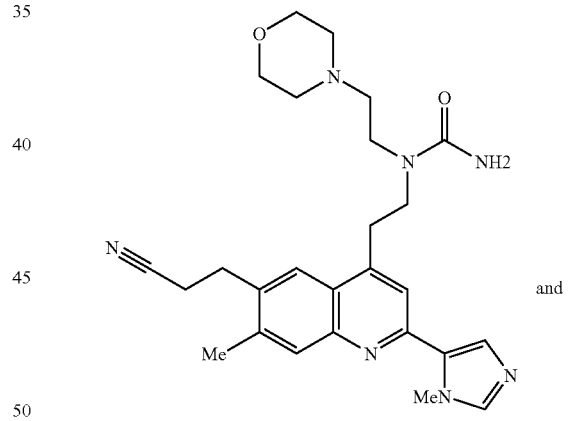
and
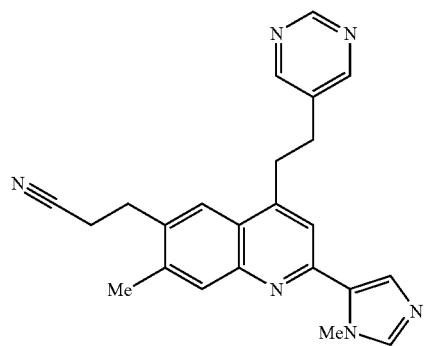
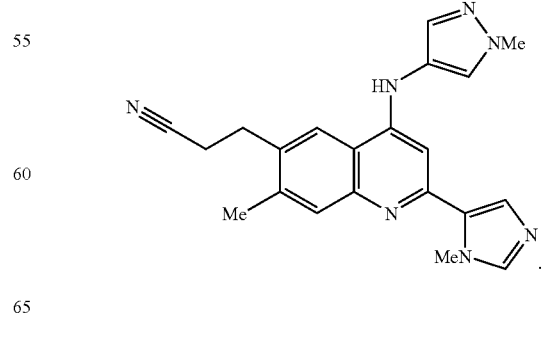
* * * * *

UNITED STATES PATENT AND TRADEMARK OFFICE
CERTIFICATE OF CORRECTION

PATENT NO.         : 7,176,314 B2                                          Page 1 of 1
APPLICATION NO. : 10/314428
DATED              : February 13, 2007
INVENTOR(S)        : Clark et al.

It is certified that error appears in the above-identified patent and that said Letters Patent is hereby corrected as shown below:

On the Title Page, the assignee information should read as follows:

Item (73)    Assignee: Amgen Inc. and Rohche Palo Alto LLC.

Signed and Sealed this

Twenty-first Day of August, 2007

JON W. DUDAS
*Director of the United States Patent and Trademark Office*